United States Patent
Kolkman

(10) Patent No.: US 10,214,588 B2
(45) Date of Patent: Feb. 26, 2019

(54) PROVIDING IMPROVED IMMUNOGLOBULIN SEQUENCES BY MUTATING CDR AND/OR FR POSITIONS

(75) Inventor: Joost Alexander Kolkman, Sint-Martens-Latem (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 1222 days.

(21) Appl. No.: 12/667,075

(22) PCT Filed: Jul. 3, 2008

(86) PCT No.: PCT/EP2008/058617
§ 371 (c)(1),
(2), (4) Date: Jun. 10, 2010

(87) PCT Pub. No.: WO2009/004065
PCT Pub. Date: Jan. 8, 2009

(65) Prior Publication Data
US 2010/0292083 A1    Nov. 18, 2010

Related U.S. Application Data

(60) Provisional application No. 60/958,164, filed on Jul. 3, 2007.

(51) Int. Cl.
*C07K 16/28* (2006.01)
*C40B 50/06* (2006.01)

(52) U.S. Cl.
CPC ...... *C07K 16/2866* (2013.01); *C07K 2317/22* (2013.01); *C07K 2317/24* (2013.01);
(Continued)

(58) Field of Classification Search
None
See application file for complete search history.

(56) References Cited

U.S. PATENT DOCUMENTS

2005/0234225 A1* 10/2005 Zhu ........................... 530/388.22
2009/0087478 A1*  4/2009 Hansen et al. ................ 424/450

FOREIGN PATENT DOCUMENTS

EP    0368684 A1    5/1990
EP    0368684 B1    3/1994
(Continued)

OTHER PUBLICATIONS

Tanaka et al., 2003, Nucleic Acids Research 31: e23.*
(Continued)

*Primary Examiner* — Christian C Boesen
(74) *Attorney, Agent, or Firm* — Wolf, Greenfield & Sacks, P.C.

(57) ABSTRACT

The present invention relates to methods and techniques for providing improved amino acid sequences that can be used as single antigen-binding domains. In particular, the invention relates to methods and techniques for providing improved amino acid sequences that can be used as single antigen-binding domains that comprise or essentially consist of at least one immunoglobulin sequence. More in particular, the amino acid sequences provided herein may comprise or essentially consist of at least one variable domain sequence or a suitable fragment thereof such as at least one light chain variable domain sequence (e.g. a $V_L$-sequence) or a suitable fragment thereof or at least one heavy chain variable domain sequence (e.g. a $V_H$-sequence or $V_{HH}$ sequence) or a suitable fragment thereof.

5 Claims, 9 Drawing Sheets

Figure 5:
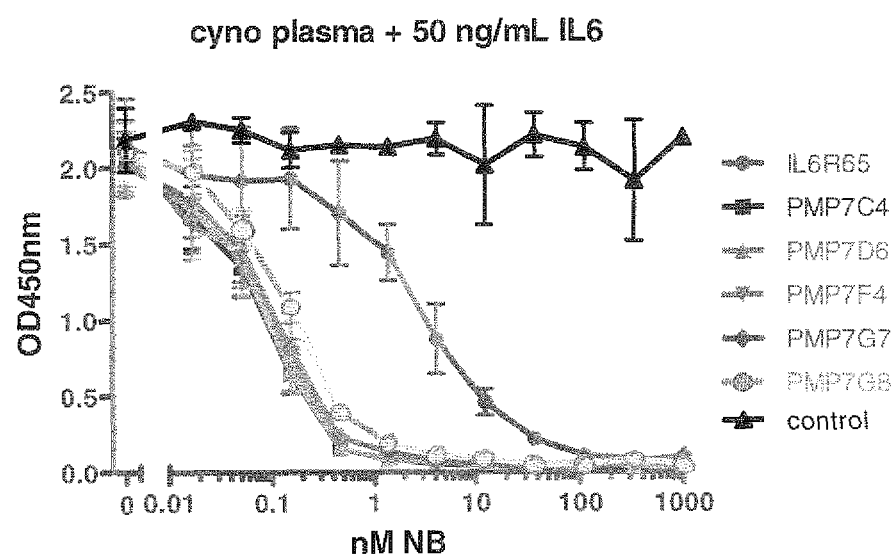

Specification includes a Sequence Listing.

PCR-assembly

(52) U.S. Cl.
CPC .... *C07K 2317/569* (2013.01); *C07K 2317/73* (2013.01); *C07K 2317/92* (2013.01); *C40B 50/06* (2013.01)

(56) References Cited

FOREIGN PATENT DOCUMENTS

| | | |
|---|---|---|
| EP | 1134231 A1 | 9/2001 |
| EP | 1433793 A1 | 6/2004 |
| EP | 0368684 B2 | 9/2004 |
| EP | 1134231 B1 | 4/2009 |
| WO | WO 94/04678 A1 | 3/1994 |
| WO | WO 94/25591 A1 | 11/1994 |
| WO | WO 95/04079 A1 | 2/1995 |
| WO | WO 96/34103 A1 | 10/1996 |
| WO | WO 97/49805 A2 | 12/1997 |
| WO | WO 99/37681 A2 | 7/1999 |
| WO | WO 00/40968 A1 | 7/2000 |
| WO | WO 00/43507 A1 | 7/2000 |
| WO | WO 00/65057 A1 | 11/2000 |
| WO | WO 01/21817 A1 | 3/2001 |
| WO | WO 01/40310 A2 | 6/2001 |
| WO | WO 01/44301 A1 | 6/2001 |
| WO | WO 01/90190 A2 | 11/2001 |
| WO | WO 02/48193 A2 | 6/2002 |
| WO | WO 03/025020 A1 | 3/2003 |
| WO | WO 03/035694 A2 | 5/2003 |
| WO | WO 03/050531 A2 | 6/2003 |
| WO | WO 03/054016 A2 | 7/2003 |
| WO | WO 03/055527 A2 | 7/2003 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/062551 A2 | 7/2004 |
| WO | WO 2005/044858 A1 | 5/2005 |
| WO | WO 2005/118629 A1 | 12/2005 |
| WO | WO 2006/003388 A2 | 1/2006 |
| WO | WO 2006/008548 A2 | 1/2006 |
| WO | WO 2006/014498 A2 | 2/2006 |
| WO | WO 2006/030220 A1 | 3/2006 |
| WO | WO 2006/040153 A2 | 4/2006 |
| WO | WO 2006/079372 A1 | 8/2006 |
| WO | WO 2006/122786 A2 | 11/2006 |
| WO | WO 2006/122787 A2 | 11/2006 |
| WO | WO 2006/122825 A2 | 11/2006 |
| WO | WO 2009/004065 A2 | 1/2009 |
| WO | WO 2009/004066 A2 | 1/2009 |

OTHER PUBLICATIONS

Azriel-Rosenfeld, Ronit, et al., "A Human Synthetic Combinatorial Library of Arrayable Single-chain Antibodies based on Shuffling in Vivo formed CDRs into General Framework Regions," 2004, J. Mol. Biol., vol. 335, pp. 177-192.*
Edelman et al 1969 PNAS 63: 78-85.*
Ward et al 1989 Nature 341: 544-546.*
Pons et al. (May 1999) Protein Science vol. 8 pp. 958 to 968.*
Tanaka et al. (Mar. 1, 2003) Nucleic Acids Research vol. 31 article e23 pp. 1 to 10.*
Benhar. Design of synthetic antibody libraries. Expert Opin Biol Ther. May 2007;7(5):763-79.
Conrath et al., Antigen binding and solubility effects upon the veneering of a camel VHH in framework-2 to mimic a VH. J Mol Biol. Jul. 1, 2005;350(1):112-25.
Goldman et al., Facile generation of heat-stable antiviral and antitoxin single domain antibodies from a semisynthetic llama library. Anal Chem. Dec. 15, 2006;78(24):8245-55.
Holt et al., Domain antibodies: proteins for therapy. Trends Biotechnol. Nov. 2003;21(11):484-90.
Hoogenboom. Selecting and screening recombinant antibody libraries. Nat Biotechnol. Sep. 2005;23(9):1105-16.
Muyldermans et al., Unique single-domain antigen binding fragments derived from naturally occurring camel heavy-chain antibodies. J Mol Recognit. Mar.-Apr. 1999;12(2):131-40.
Ohtomo et al., Humanization of mouse ONS-M21 antibody with the aid of hybrid variable regions. Mol Immunol. Apr. 1995;32(6):407-16.
Riechmann et al., Single domain antibodies: comparison of camel VH and camelised human VH domains. J Immunol Methods. Dec. 10, 1999;231(1-2):25-38.
Sato et al., Humanization of a mouse anti-human interleukin-6 receptor antibody comparing two methods for selecting human framework regions. Mol Immunol. Apr. 1994;31(5):371-81.
Sneeden et al., Random oligonucleotide mutagenesis. Methods Mol Biol. 2003;231:65-73.
Söderlind et al., Domain libraries: synthetic diversity for de novo design of antibody V-regions. Gene. Jul. 28, 1995;160(2):269-72.
Wu et al., Humanization of a murine monoclonal antibody by simultaneous optimization of framework and CDR residues. J Mol Biol. Nov. 19, 1999;294(1):151-62.
Deng et al., Recombinant single-chain variable fragment antibodies directed against Clostridium difficile toxin B produced by use of an optimized phage display system. Clin Diagn Lab Immunol. Jul. 2003;10(4):587-95.
Hamers-Casterman et al., Naturally occurring antibodies devoid of light chains. Nature. Jun. 3, 1993;363(6428):446-8.
Holliger et al., Engineered antibody fragments and the rise of single domains. Nat Biotechnol. Sep. 2005;23(9):1126-36.
Hust et al., Mating antibody phage display with proteomics. Trends Biotechnol. Jan. 2004;22(1):8-14.
Lauwereys et al., Potent enzyme inhibitors derived from dromedary heavy-chain antibodies. Embo J. Jul. 1, 1998;17(13):3512-20.
Martin, Protein sequence and structure analysis of antibody variable domains; Antibody engineering. Chapter 3. 2010; Antibody Engineering vol. 2:33-51, R. Kontermann and S. Dubel.
Muyldermans, Single domain camel antibodies: current status. Rev Mol Biotechnol. Jun. 2001;74(4):277-302.
Stemmer et al., Single-step assembly of a gene and entire plasmid from large numbers of oligodeoxyribonucleotides. Gene. Oct. 16, 1995;164(1):49-53.
Transue et al., Camel single-domain antibody inhibits enzyme by mimicking carbohydrate substrate. Proteins. Sep. 1, 1998;32(4):515-22.
Ward et al., Binding activities of a repertoire of single immunoglobulin variable domains secreted from *Escherichia coli*. Nature. Oct. 12, 1989;341(6242):544-6.
Roitt et al. Molecules which Recognize Antigen. Immunology. 1989:5.1-5.11.
Sidhu et al., Phage-displayed antibody libraries of synthetic heavy chain complementarity determining regions. J Mol Biol. Apr. 23, 2004;338(2):299-310.
Davies et al., Antibody VH domains as small recognition units. Biotechnology (N Y). May 1995; 13(5):475-9.
Riechmann, Rearrangement of the former VL interface in the solution structure of a camelised, single antibody VH domain. J Mol Biol. Jun. 28, 1996;259(5):957-69.
Wesolowski et al., Single domain antibodies: promising experimental and therapeutic tools in infection and immunity. Med Microbiol Immunol. Aug. 2009;198(3):157-74. doi: 10.1007/s00430-009-0116-7. Epub Jun. 16, 2009.
PCT/EP2008/058618, May 20, 2009, International Search Report and Written Opinion.
PCT/EP2008/058618, Jan. 5, 2010, International Preliminary Report on Patentability.

* cited by examiner

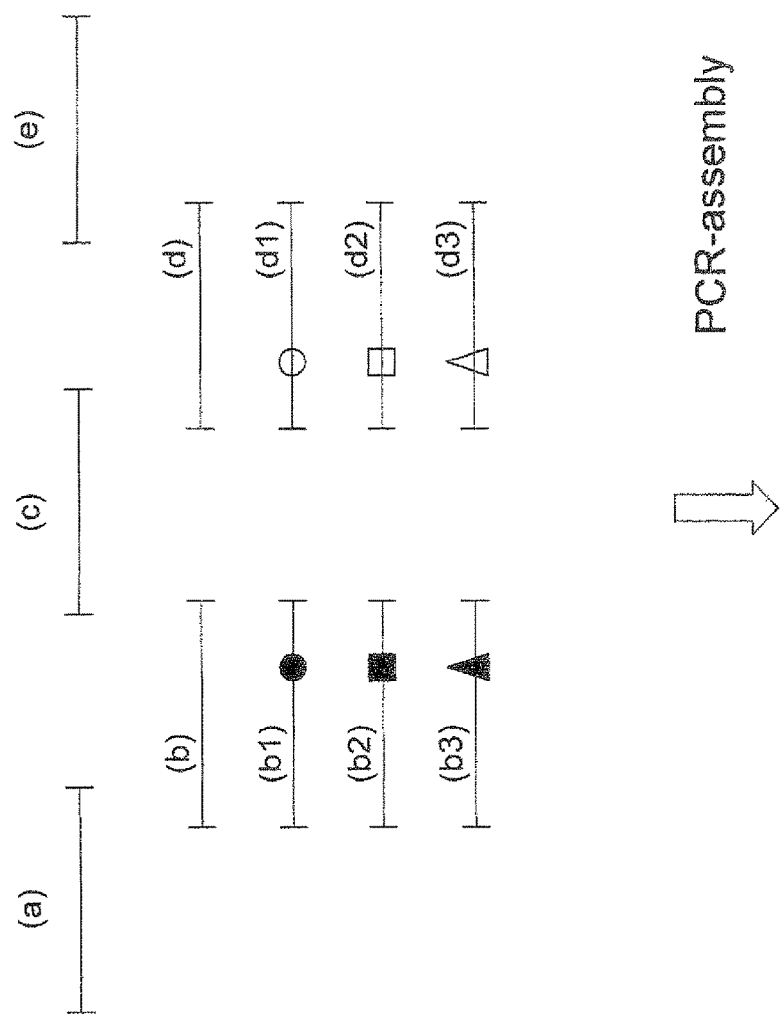
Figure 1-A

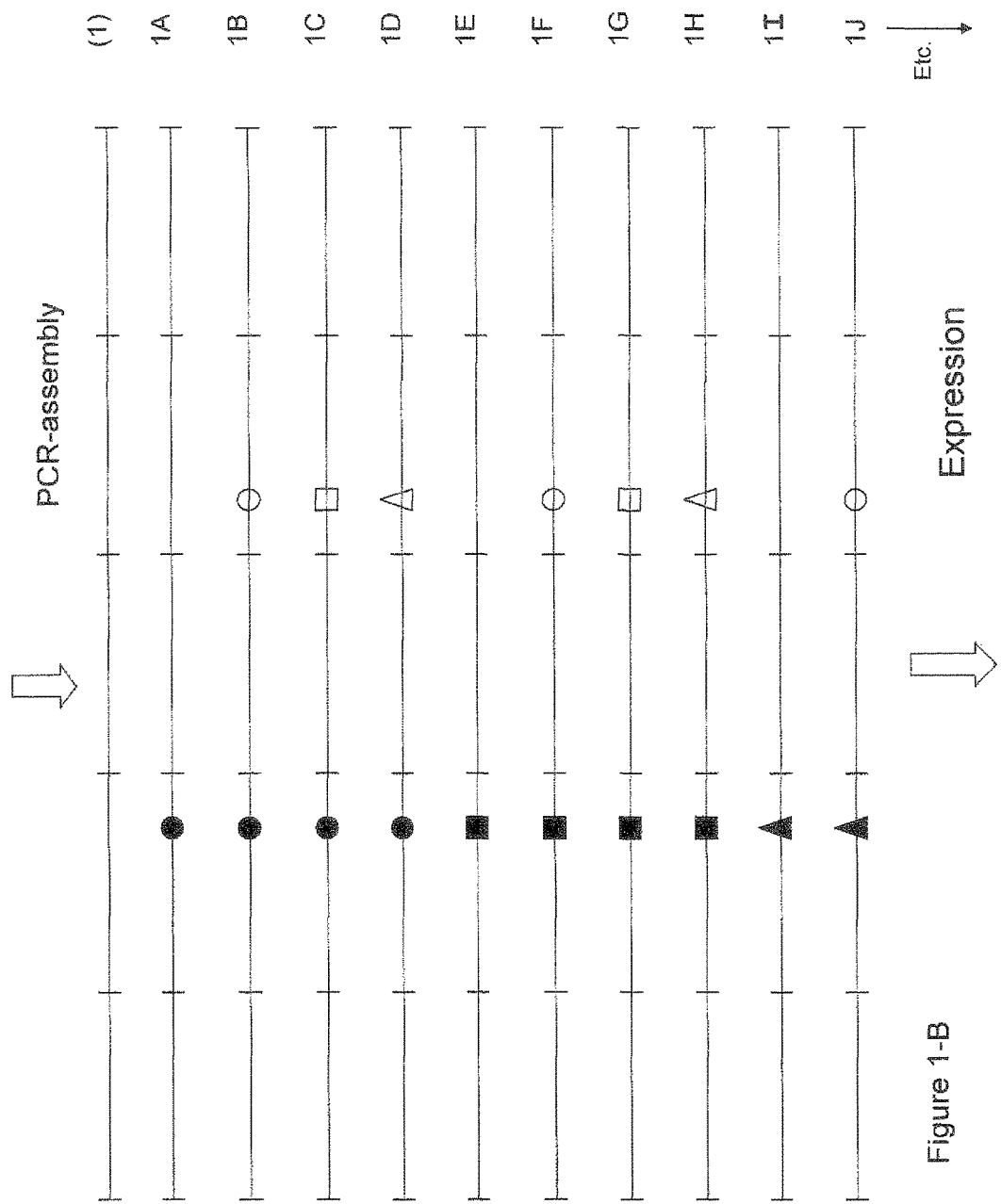
Figure 1-B

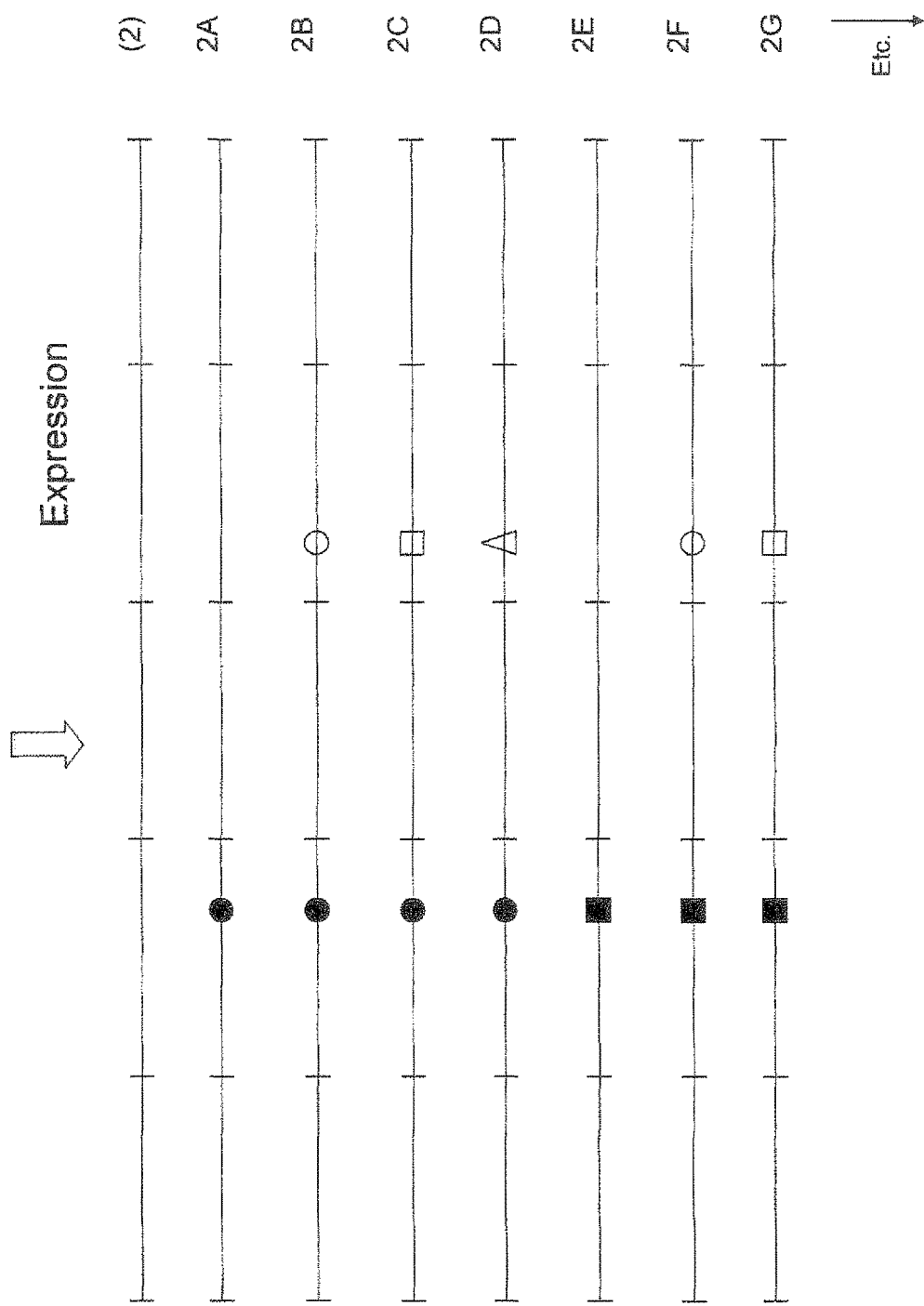
Figure 1-C

Figure 2: Overlapping oligo's used for Nanobody assembly

```
>For_IL6R04/1    gggaggttactgaGGCCCAGCCGGCCATGGCCgaggtgcagctggtg
>Rev_IL6R04/1    TTGAACCAGACCTCCGCCAGACTCCACCAGCTGCACCTC
>For_IL6R04/2a   ggaggtctggttcaagcaggcggagctTgcgtctgagttgcgctgcg
>For_IL6R04/2b   ggaggtctggttcaaccggcgggagcttgcgtctgagttgcgctgcg
>Rev_IL6R04/2a   TCCGATGTCGTAGTCATCAAATGTGAAACCGTCGCAGCGCAACTCAG
>Rev_IL6R04/2b   TCCGATGTCGTAGTCGCTAAATGTGAAACCGTCGCAGCGCAACTCAG
>For_IL6R04/3a   gactacgacatcggatggtttcgtcaggctccgggcaaa
>For_IL6R04/3b   gactacgacatcggatgggttcgtcaggctccgggcaaa
>Rev_IL6R04/3a   AGAACTTGAAATGCCGGACACACCTTCGCGACCTTTGCCCGGAGCCTG
>Rev_IL6R04/3b   AGAACTTGAAATGCCGGACACACCTTCGAGTTCTTTGCCCGGAGCCTG
>Rev_IL6R04/3c   AGAACTTGAAATGCCGGACACCCATTCGCGTTCTTTGCCCGGAGCCTG
>For_IL6R04/4    ggcatttcaagttctgacggcaacacttattac
>Rev_IL6R04/4    ACCTTTAACGTGTCTGCGTAATAAGTGTTGCC
>For_IL6R04/5a   gacagcgttaaaggtcgtttcaccatttcgtccgataacgcaaagaat
>For_IL6R04/5b   gacagcgttaaaggtcgtttcaccatttcgcgtgataacgcaaagaat
>Rev_IL6R04/5a   TAAGCTATTCATTTGAAGGTATACGGTATTCTTTGCGTTATC
>Rev_IL6R04/5b   TAAGCTATTCATTTGAAGGTACAGGTATTCTTTGCGTTATC
>For_IL6R04/6a   caaatgaatagcttacgccggaagataccgcgtttactattgtgcc
>For_IL6R04/6b   caaatgaatagcttaaaagctgaagataccgcgtttactattgtgcc
>Rev_IL6R04/6a   CAGATACCACGAGCTATCTGGCGGTTCCGCGGCACAATAGTAAAC
>Rev_IL6R04/6b   CAGATACCACGAGCTATCTGGCGGTTCGCGGGCACAATAGTAAAC
>For_IL6R04/7    agctcgtggtatctggatggctctcctgaattctttaaatattggggt
>Rev_IL6R04/7a   GTTGTGAGGAGACGGTGACCTGCGTACCCTGACCCCAATATTTAAAGA
>Rev_IL6R04/7b   GTTGTGAGGAGACGGTGACCAGCGTACCCTGACCCCAATATTTAAAGA
>For_IL6R04/r    ggaggttactgaGGC
>Rev_IL6R04/r    GTTGTGAGGAGACGGTG
```

Figure 3-A. Protein sequence alignment of Nanobody 32C9 wildtype and humanized variants.

Figure 3-B Protein sequence alignment of Nanobody 32C9 wildtype and humanized variants (cont.).

Figure 4.

Library a
EVQLVESGGGLVQPGGSLRLSCAASG SIFKVNAMG WYRQAPGKGRELVA GIISGGSTN YADSVKGRFTISRDNAKNTLYLQMNSLRPEDTAVYYCAF VTTNSDYDLGRDY WGQGTLVTVSS
                           TLYRLDS A                AVVAA ASD
                           AV   I T                 LLT  TA Library b
EVQLVESGGGLVQPGGSLRLSCAASG SIFKVNAMG WYRQAPGKGRELVA GIISGGSTN YADSVKGRFTISRDNAKNTLYLQMNSLRPEDTAVYYCAF VTTNSDYDLGRDY WGQGTLVTVSS
                           TT RLDV A                AVTNS N T
                              SIYT                  STN  T S
                              NF I                       N Library c
EVQLVESGGGLVQPGGSLRLSCAASG SIFKVNAMG WYRQAPGKGRELVA GIISGGSTN YADSVKGRFTISRDNAKNTLYLQMNSLRPEDTAVYYCAF VTTNSDYDLGRDY WGQGTLVTVSS
                                                                                                    IAADAEFEIAKEF
                                                                                                    LSS TNSNV  NS
                                                                                                         K K    K

SEQUENCE LISTING

```
<160> NUMBER OF SEQ ID NOS: 210

<210> SEQ ID NO 1
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Pro Phe Ser Xaa Xaa
                20                  25                  30

Xaa Xaa Xaa Trp Phe Arg Gln Ala Pro Gly Lys Gln Arg Asp Ser Val
            35                  40                  45

Ala Xaa Xaa Xaa Xaa Xaa Arg Phe Thr Ile Ser Arg Asp Asn Ala Lys
    50                  55                  60
```

```
Asn Thr Val Tyr Leu Gln Met Asn Ser Leu Lys Pro Glu Asp Thr Ala
 65                  70                  75                  80

Val Tyr Arg Cys Tyr Phe Xaa Xaa Xaa Xaa Xaa Trp Gly Gln Gly Thr
                 85                  90                  95

Gln Val Thr Val Ser Ser
            100
```

```
<210> SEQ ID NO 2
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 2

Gln Val Lys Leu Glu Glu Ser Gly Gly Gly Leu Val Gln Ala Gly Gly
 1               5                  10                  15

Ser Leu Arg Leu Ser Cys Val Gly Ser Gly Arg Thr Phe Ser Xaa Xaa
                 20                  25                  30

Xaa Xaa Xaa Trp Phe Arg Leu Ala Pro Gly Lys Glu Arg Glu Phe Val
            35                  40                  45

Ala Xaa Xaa Xaa Xaa Xaa Arg Phe Thr Ile Ser Arg Asp Thr Ala Ser
     50                  55                  60

Asn Arg Gly Tyr Leu His Met Asn Asn Leu Thr Pro Glu Asp Thr Ala
 65                  70                  75                  80

Val Tyr Tyr Cys Ala Ala Xaa Xaa Xaa Xaa Xaa Trp Gly Gln Gly Thr
                 85                  90                  95

Gln Val Thr Val Ser Ser
            100
```

```
<210> SEQ ID NO 3
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 3

Ala Val Gln Leu Val Asp Ser Gly Gly Gly Leu Val Gln Ala Gly Asp
 1               5                  10                  15

Ser Leu Lys Leu Ser Cys Ala Leu Thr Gly Gly Ala Phe Thr Xaa Xaa
```

```
                        20                  25                  30

Xaa Xaa Xaa Trp Phe Arg Gln Thr Pro Gly Arg Glu Arg Glu Phe Val
        35                  40                  45

Ala Xaa Xaa Xaa Xaa Xaa Arg Phe Thr Ile Ser Arg Asp Asn Ala Lys
50                  55                  60

Asn Met Val Tyr Leu Arg Met Asn Ser Leu Ile Pro Glu Asp Ala Ala
65                  70                  75                  80

Val Tyr Ser Cys Ala Ala Xaa Xaa Xaa Xaa Xaa Trp Gly Gln Gly Thr
                85                  90                  95

Leu Val Thr Val Ser Ser
            100

<210> SEQ ID NO 4
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 4

Gln Val Gln Leu Val Glu Ser Gly Gly Gly Leu Val Glu Ala Gly Gly
1               5                   10                  15

Ser Leu Arg Leu Ser Cys Thr Ala Ser Glu Ser Pro Phe Arg Xaa Xaa
                20                  25                  30

Xaa Xaa Xaa Trp Phe Arg Gln Ser Gly Gln Glu Arg Glu Phe Val
        35                  40                  45

Ala Xaa Xaa Xaa Xaa Xaa Arg Phe Thr Ile Ser Arg Asp Asp Ala Lys
50                  55                  60

Asn Thr Val Trp Leu His Gly Ser Thr Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 5
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid
```

<400> SEQUENCE: 5

```
Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Xaa Xaa
            20                  25                  30

Xaa Xaa Xaa Trp Tyr Arg Gln Gly Pro Gly Asn Glu Arg Glu Leu Val
        35                  40                  45

Ala Xaa Xaa Xaa Xaa Arg Phe Thr Ile Ser Met Asp Tyr Thr Lys
    50                  55                  60

Gln Thr Val Tyr Leu His Met Asn Ser Leu Arg Pro Glu Asp Thr Gly
65                  70                  75                  80

Leu Tyr Tyr Cys Lys Ile Xaa Xaa Xaa Xaa Xaa Trp Gly Gln Gly Thr
                85                  90                  95

Gln Val Thr Val Ser Ser
            100
```

<210> SEQ ID NO 6
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 6

```
Asp Val Lys Phe Val Glu Ser Gly Gly Gly Leu Val Gln Ala Gly Gly
1               5                   10                  15

Ser Leu Arg Leu Ser Cys Val Ala Ser Gly Phe Asn Phe Asp Xaa Xaa
            20                  25                  30

Xaa Xaa Xaa Trp Phe Arg Gln Ala Pro Gly Lys Glu Arg Glu Val
        35                  40                  45

Ala Xaa Xaa Xaa Xaa Xaa Arg Phe Thr Ile Ser Ser Glu Lys Asp Lys
    50                  55                  60

Asn Ser Val Tyr Leu Gln Met Asn Ser Leu Lys Pro Glu Asp Thr Ala
65                  70                  75                  80

Leu Tyr Ile Cys Ala Gly Xaa Xaa Xaa Xaa Xaa Trp Gly Arg Gly Thr
                85                  90                  95

Gln Val Thr Val Ser Ser
            100
```

<210> SEQ ID NO 7
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:

<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 7

```
Gln Val Arg Leu Ala Glu Ser Gly Gly Gly Leu Val Gln Ser Gly Gly
1               5                   10                  15

Ser Leu Arg Leu Ser Cys Val Ala Ser Gly Ser Thr Tyr Thr Xaa Xaa
            20                  25                  30

Xaa Xaa Xaa Trp Tyr Arg Gln Tyr Pro Gly Lys Gln Arg Ala Leu Val
        35                  40                  45

Ala Xaa Xaa Xaa Xaa Xaa Arg Phe Thr Ile Ala Arg Asp Ser Thr Lys
    50                  55                  60

Asp Thr Phe Cys Leu Gln Met Asn Asn Leu Lys Pro Glu Asp Thr Ala
65                  70                  75                  80

Val Tyr Tyr Cys Tyr Ala Xaa Xaa Xaa Xaa Trp Gly Gln Gly Thr
                85                  90                  95

Gln Val Thr Val Ser Ser
            100
```

<210> SEQ ID NO 8
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 8

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Ser Asp Xaa Xaa
            20                  25                  30

Xaa Xaa Xaa Trp Phe Arg Gln Ala Pro Gly Lys Pro Arg Glu Gly Val
        35                  40                  45

Ser Xaa Xaa Xaa Xaa Xaa Arg Phe Thr Ile Ser Thr Asp Asn Ala Lys
    50                  55                  60

Asn Thr Val His Leu Leu Met Asn Arg Val Asn Ala Glu Asp Thr Ala
65                  70                  75                  80

Leu Tyr Tyr Cys Ala Val Xaa Xaa Xaa Xaa Xaa Trp Gly Arg Gly Thr
                85                  90                  95

Arg Val Thr Val Ser Ser
            100
```

<210> SEQ ID NO 9
<211> LENGTH: 102
<212> TYPE: PRT
<213> ORGANISM: Artificial

```
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
        35                  40                  45

Ala Xaa Xaa Xaa Xaa Xaa Arg Phe Thr Ile Ser Gly Asp Asn Ala Lys
    50                  55                  60

Arg Ala Ile Tyr Leu Gln Met Asn Asn Leu Lys Pro Asp Asp Thr Ala
65                  70                  75                  80

Val Tyr Tyr Cys Asn Arg Xaa Xaa Xaa Xaa Xaa Trp Gly Gln Gly Thr
                85                  90                  95

Gln Val Thr Val Ser Pro
            100

<210> SEQ ID NO 10
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 10

Gln Val Pro Val Val Glu Ser Gly Gly Gly Leu Val Gln Ala Gly Asp
1               5                   10                  15

Ser Leu Arg Leu Phe Cys Ala Val Pro Ser Phe Thr Ser Thr Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asn Ala Thr Lys
    50                  55                  60

Asn Thr Leu Thr Leu Arg Met Asp Ser Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
```

-continued

```
<210> SEQ ID NO 11
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 11

Glu Val Gln Leu Val Glu Ser Gly Gly Gly Leu Val Gln Ala Gly Asp
1               5                   10                  15

Ser Leu Arg Leu Phe Cys Thr Val Ser Gly Gly Thr Ala Ser Xaa Xaa
            20                  25                  30

Xaa Xaa Xaa Trp Phe Arg Gln Ala Pro Gly Glu Lys Arg Glu Phe Val
        35                  40                  45

Ala Xaa Xaa Xaa Xaa Xaa Arg Phe Thr Ile Ala Arg Glu Asn Ala Gly
    50                  55                  60

Asn Met Val Tyr Leu Gln Met Asn Asn Leu Lys Pro Asp Asp Thr Ala
65                  70                  75                  80

Leu Tyr Thr Cys Ala Ala Xaa Xaa Xaa Xaa Xaa Trp Gly Arg Gly Thr
                85                  90                  95

Gln Val Thr Val Ser Ser
            100

<210> SEQ ID NO 12
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 12

Ala Val Gln Leu Val Glu Ser Gly Gly Asp Ser Val Gln Pro Gly Asp
1               5                   10                  15

Ser Gln Thr Leu Ser Cys Ala Ala Ser Gly Arg Thr Asn Ser Xaa Xaa
            20                  25                  30

Xaa Xaa Xaa Trp Phe Arg Gln Ala Pro Gly Lys Glu Arg Val Phe Leu
        35                  40                  45

Ala Xaa Xaa Xaa Xaa Xaa Arg Phe Thr Ile Ser Arg Asp Ser Ala Lys
    50                  55                  60
```

```
Asn Met Met Tyr Leu Gln Met Asn Asn Leu Lys Pro Gln Asp Thr Ala
 65                  70                  75                  80

Val Tyr Tyr Cys Ala Ala Xaa Xaa Xaa Xaa Xaa Trp Gly Gln Gly Thr
                 85                  90                  95

Gln Val Thr Val Ser Ser
            100

<210> SEQ ID NO 13
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 13

Ala Val Gln Leu Val Glu Ser Gly Gly Gly Leu Val Gln Ala Gly Gly
 1               5                  10                  15

Ser Leu Arg Leu Ser Cys Val Val Ser Gly Leu Thr Ser Ser Xaa Xaa
                20                  25                  30

Xaa Xaa Xaa Trp Phe Arg Gln Thr Pro Trp Gln Glu Arg Asp Phe Val
                35                  40                  45

Ala Xaa Xaa Xaa Xaa Xaa Arg Phe Thr Ile Ser Arg Asp Asn Tyr Lys
 50                  55                  60

Asp Thr Val Leu Leu Glu Met Asn Phe Leu Lys Pro Glu Asp Thr Ala
 65                  70                  75                  80

Ile Tyr Tyr Cys Ala Ala Xaa Xaa Xaa Xaa Xaa Trp Gly Gln Gly Thr
                 85                  90                  95

Gln Val Thr Val Ser Ser
            100

<210> SEQ ID NO 14
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 14

Ala Val Gln Leu Val Glu Ser Gly Gly Gly Leu Val Gln Ala Gly Ala
 1               5                  10                  15

Ser Leu Arg Leu Ser Cys Ala Thr Ser Thr Arg Thr Leu Asp Xaa Xaa
                20                  25                  30
```

Xaa Xaa Xaa Trp Phe Arg Gln Ala Pro Gly Arg Asp Arg Glu Phe Val
         35                  40                  45

Ala Xaa Xaa Xaa Xaa Xaa Arg Phe Thr Val Ser Arg Asp Ser Ala Glu
        50                  55                  60

Asn Thr Val Ala Leu Gln Met Asn Ser Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Arg Val Thr Val Ser Ser
            100

<210> SEQ ID NO 15
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Thr Val Ser Arg Leu Thr Ala His Xaa Xaa
            20                  25                  30

Xaa Xaa Xaa Trp Phe Arg Gln Ala Pro Gly Lys Glu Arg Glu Ala Val
         35                  40                  45

Ser Xaa Xaa Xaa Xaa Xaa Arg Phe Thr Ile Ser Arg Asp Tyr Ala Gly
        50                  55                  60

Asn Thr Ala Phe Leu Gln Met Asp Ser Leu Lys Pro Glu Asp Thr Gly
65                  70                  75                  80

Val Tyr Tyr Cys Ala Thr Xaa Xaa Xaa Xaa Xaa Trp Gly Gln Gly Thr
                85                  90                  95

Gln Val Thr Val Ser Ser
            100

<210> SEQ ID NO 16
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 16

Glu Val Gln Leu Val Glu Ser Gly Gly Glu Leu Val Gln Ala Gly Gly
1               5                   10                  15

Ser Leu Lys Leu Ser Cys Thr Ala Ser Gly Arg Asn Phe Val Xaa Xaa
            20                  25                  30

Xaa Xaa Xaa Trp Phe Arg Arg Ala Pro Gly Lys Glu Arg Glu Phe Val
        35                  40                  45

Ala Xaa Xaa Xaa Xaa Xaa Arg Phe Thr Val Ser Arg Asp Asn Gly Lys
    50                  55                  60

Asn Thr Ala Tyr Leu Arg Met Asn Ser Leu Lys Pro Glu Asp Thr Ala
65                  70                  75                  80

Asp Tyr Tyr Cys Ala Val Xaa Xaa Xaa Xaa Xaa Leu Gly Ser Gly Thr
                85                  90                  95

Gln Val Thr Val Ser Ser
            100

<210> SEQ ID NO 17
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 17

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Gln Met Asn Ser Leu Lys Pro Glu Asp Thr Ala
65                  70                  75                  80

Val Tyr Tyr Cys Val Lys Xaa Xaa Xaa Xaa Xaa Gly Ser Gln Gly Thr
                85                  90                  95

Gln Val Thr Val Ser Ser
            100

<210> SEQ ID NO 18
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature

```
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 18

Glu Val Gln Leu Val Glu Ser Gly Gly Gly Leu Val Gln Pro Gly Gly
 1               5                  10                  15

Ser Leu Arg Leu Ser Cys Val Cys Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65              70                  75                  80

Met Tyr Tyr Cys Gln Arg Xaa Xaa Xaa Xaa Arg Gly Gln Gly Thr
                85                  90                  95

Gln Val Thr Val Ser Ser
            100

<210> SEQ ID NO 19
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 19

Glu Val Gln Leu Val Glu Ser Gly Gly Gly Leu Ala Leu Pro Gly Gly
 1               5                  10                  15

Ser Leu Thr Leu Ser Cys Val Phe Ser Gly Ser Thr Phe Ser Xaa Xaa
            20                  25                  30

Xaa Xaa Xaa Trp Val Arg His Thr Pro Gly Lys Ala Glu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Glu Met Asn Ser Leu Ser Pro Glu Asp Thr Ala
65              70                  75                  80

Met Tyr Tyr Cys Gly Arg Xaa Xaa Xaa Xaa Xaa Arg Ser Lys Gly Ile
                85                  90                  95

Gln Val Thr Val Ser Ser
            100

<210> SEQ ID NO 20
<211> LENGTH: 102
<212> TYPE: PRT
<213> ORGANISM: Artificial
<220> FEATURE:
```

```
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 20

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Tyr Cys Ala Ala Xaa Xaa Xaa Xaa Xaa Arg Gly Gln Gly Thr
                85                  90                  95

Gln Val Thr Val Ser Ser
            100

<210> SEQ ID NO 21
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 21

Asp Val Gln Leu Val Glu Ser Gly Gly Asp Leu Val Gln Pro Gly Gly
1               5                   10                  15

Ser Leu Arg Leu Ser Cys Ala Ala Ser Gly Phe Ser Phe Asp Xaa Xaa
            20                  25                  30

Xaa Xaa Xaa Trp Leu Arg Gln Thr Pro Gly Lys Gly Leu Glu Trp Val
        35                  40                  45

Gly Xaa Xaa Xaa Xaa Xaa Arg Phe Thr Ile Ser Arg Asp Asn Ala Lys
    50                  55                  60

Asn Met Leu Tyr Leu His Leu Asn Asn Leu Lys Ser Glu Asp Thr Ala
65                  70                  75                  80

Val Tyr Tyr Cys Arg Arg Xaa Xaa Xaa Xaa Xaa Leu Gly Gln Gly Thr
                85                  90                  95

Gln Val Thr Val Ser Ser
            100
```

<210> SEQ ID NO 22
<211> LENGTH: 102
<212> TYPE: PRT
<213> ORGANISM: Artificial
<220> FEATURE:
<223> OTHER INFORMATION: Nanobody or Nanobody Fragment
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 23
<211> LENGTH: 47
<212> TYPE: DNA
<213> ORGANISM: Artificial
<220> FEATURE:
<223> OTHER INFORMATION: Nanobody or Nanobody Fragment

<400> SEQUENCE: 23
gggaggttac tgaggcccag ccggccatgg ccgaggtgca gctggtg        47

<210> SEQ ID NO 24
<211> LENGTH: 39
<212> TYPE: DNA
<213> ORGANISM: Artificial
<220> FEATURE:
<223> OTHER INFORMATION: Nanobody or Nanobody Fragment

<400> SEQUENCE: 24
ttgaaccaga cctccgccag actccaccag ctgcacctc        39

<210> SEQ ID NO 25
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 25
ggaggtctgg ttcaagcagg cgggagcttg cgtctgagtt gcgctgcg        48

<210> SEQ ID NO 26
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 26
ggaggtctgg ttcaaccggg cgggagcttg cgtctgagtt gcgctgcg                48

<210> SEQ ID NO 27
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 27
tccgatgtcg tagtcatcaa atgtgaaacc gctcgcagcg caactcag                48

<210> SEQ ID NO 28
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 28
tccgatgtcg tagtcgctaa atgtgaaacc gctcgcagcg caactcag                48

<210> SEQ ID NO 29
<211> LENGTH: 39
<212> TYPE: DNA
<213> ORGANISM: Artificial
<220> FEATURE:
<223> OTHER INFORMATION: Nanobody or Nanobody Fragment

<400> SEQUENCE: 29
gactacgaca tcggatggtt tcgtcaggct ccgggcaaa                39

<210> SEQ ID NO 30
<211> LENGTH: 39
<212> TYPE: DNA
<213> ORGANISM: Artificial
<220> FEATURE:
<223> OTHER INFORMATION: Nanobody or Nanobody Fragment

<400> SEQUENCE: 30
gactacgaca tcggatgggt tcgtcaggct ccgggcaaa                39

<210> SEQ ID NO 31
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 31
agaacttgaa atgccggaca caccttcgcg acctttgccc ggagcctg                48

<210> SEQ ID NO 32
<211> LENGTH: 48
<212> TYPE: DNA
<213> ORGANISM: Artificial
<220> FEATURE:

```
<223> OTHER INFORMATION: Nanobody or Nanobody Fragment

<400> SEQUENCE: 32
agaacttgaa atgccggaca caccttcgag ttctttgccc ggagcctg         48

<210> SEQ ID NO 33
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 33
agaacttgaa atgccggaca cccattcgcg ttctttgccc ggagcctg         48

<210> SEQ ID NO 34
<211> LENGTH: 33
<212> TYPE: DNA
<213> ORGANISM: Artificial
<220> FEATURE:
<223> OTHER INFORMATION: Nanobody or Nanobody Fragment

<400> SEQUENCE: 34
ggcatttcaa gttctgacgg caacacttat tac                         33

<210> SEQ ID NO 35
<211> LENGTH: 33
<212> TYPE: DNA
<213> ORGANISM: Artificial
<220> FEATURE:
<223> OTHER INFORMATION: Nanobody or Nanobody Fragment

<400> SEQUENCE: 35
acctttaacg ctgtctgcgt aataagtgtt gcc                         33

<210> SEQ ID NO 36
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 36
gacagcgtta aggtcgtttc accatttcg tccgataacg caaagaat          48

<210> SEQ ID NO 37
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 37
gacagcgtta aggtcgtttc accatttcg cgtgataacg caaagaat          48

<210> SEQ ID NO 38
<211> LENGTH: 42
<212> TYPE: DNA
<213> ORGANISM: Artificial
<220> FEATURE:
<223> OTHER INFORMATION: Nanobody or Nanobody Fragment

<400> SEQUENCE: 38
taagctattc atttgaaggt atacggtatt ctttgcgtta tc               42
```

<210> SEQ ID NO 39
<211> LENGTH: 42
<212> TYPE: DNA
<213> ORGANISM: Artificial
<220> FEATURE:
<223> OTHER INFORMATION: Nanobody or Nanobody Fragment

<400> SEQUENCE: 39
taagctattc atttgaaggt acagggtatt ctttgcgtta tc          42

<210> SEQ ID NO 40
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 40
caaatgaata gcttacgccc ggaagatacc gccgtttact attgtgcc    48

<210> SEQ ID NO 41
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 41
caaatgaata gcttaaaagc tgaagatacc gccgtttact attgtgcc    48

<210> SEQ ID NO 42
<211> LENGTH: 45
<212> TYPE: DNA
<213> ORGANISM: Artificial
<220> FEATURE:
<223> OTHER INFORMATION: Nanobody or Nanobody Fragment

<400> SEQUENCE: 42
cagataccac gagctatctg gcggttccgc ggcacaatag taaac       45

<210> SEQ ID NO 43
<211> LENGTH: 45
<212> TYPE: DNA
<213> ORGANISM: Artificial
<220> FEATURE:
<223> OTHER INFORMATION: Nanobody or Nanobody Fragment

<400> SEQUENCE: 43
cagataccac gagctatctg gcggttcgcg ggcacaatag taaac       45

<210> SEQ ID NO 44
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 44
agctcgtggt atctggatgg ctctcctgaa ttctttaaat attggggt    48

<210> SEQ ID NO 45
<211> LENGTH: 48
<212> TYPE: DNA
<213> ORGANISM: Artificial
<220> FEATURE:
<223> OTHER INFORMATION: Nanobody or Nanobody Fragment

```
<400> SEQUENCE: 45
gttgtgagga gacggtgacc tgcgtaccct gaccccaata tttaaaga        48

<210> SEQ ID NO 46
<211> LENGTH: 48
<212> TYPE: DNA
<213> ORGANISM: Artificial
<220> FEATURE:
<223> OTHER INFORMATION: Nanobody or Nanobody Fragment

<400> SEQUENCE: 46
gttgtgagga gacggtgacc agcgtaccct gaccccaata tttaaaga        48

<210> SEQ ID NO 47
<211> LENGTH: 16
<212> TYPE: DNA
<213> ORGANISM: Artificial
<220> FEATURE:
<223> OTHER INFORMATION: Nanobody or Nanobody Fragment

<400> SEQUENCE: 47
gggaggttac tgaggc                                           16

<210> SEQ ID NO 48
<211> LENGTH: 17
<212> TYPE: DNA
<213> ORGANISM: Artificial
<220> FEATURE:
<223> OTHER INFORMATION: Nanobody or Nanobody Fragment

<400> SEQUENCE: 48
gttgtgagga gacggtg                                          17

<210> SEQ ID NO 49
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 49

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 50
<211> LENGTH: 127
<212> TYPE: PRT
<213> ORGANISM: Artificial
```

-continued

```
<220> FEATURE:
<223> OTHER INFORMATION: Nanobody or Nanobody Fragment

<400> SEQUENCE: 50
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

```
<210> SEQ ID NO 51
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 51
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

```
<210> SEQ ID NO 52
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 52
```

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Asp Tyr
            20                  25                  30

```
Asp Ile Gly Trp Val Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125
```

<210> SEQ ID NO 53
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125
```

<210> SEQ ID NO 54
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 54

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95
```

-continued

Ala Ala Glu Pro Pro Asp Ser Ser Trp Tyr Leu Asp Gly Ser Pro Glu
        100                 105                 110

Phe Phe Lys Tyr Trp Gly Gln Gly Thr Gln Val Thr Val Ser Ser
        115                 120                 125

<210> SEQ ID NO 55
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 55

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
        100                 105                 110

Phe Phe Lys Tyr Trp Gly Gln Gly Thr Gln Val Thr Val Ser Ser
        115                 120                 125

<210> SEQ ID NO 56
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
        100                 105                 110

Phe Phe Lys Tyr Trp Gly Gln Gly Thr Gln Val Thr Val Ser Ser
        115                 120                 125

<210> SEQ ID NO 57
<211> LENGTH: 127
<212> TYPE: PRT

<213> ORGANISM: Artificial
<220> FEATURE:
<223> OTHER INFORMATION: Nanobody or Nanobody Fragment

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 58
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 59
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

```
Asp Ile Gly Trp Val Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 60
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 60

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 61
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 61

Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Ser Asp Asn Ala Lys Asn Thr Val Tyr
 65                  70                  75                  80

Leu Gln Met Asn Ser Leu Lys Ala Glu Asp Thr Ala Val Tyr Tyr Cys
```

85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 62
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 62

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 63
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 63

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 64
<211> LENGTH: 127

<212> TYPE: PRT
<213> ORGANISM: Artificial
<220> FEATURE:
<223> OTHER INFORMATION: Nanobody or Nanobody Fragment

<400> SEQUENCE: 64

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Glu Leu Glu Trp Val
        35                  40                  45

Ser Gly Ile Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 65
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 65

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Trp Val
        35                  40                  45

Ser Gly Ile Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 66
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr

```
            20                  25                  30
Asp Ile Gly Trp Val Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 67
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 68
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 69
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 70
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 71
```

```
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 72
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 73
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 73

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Gly Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 74
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 74

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Gly Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 75
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 75

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Ser Asp Asn Ala Lys Asn Thr Leu Tyr
65                  70                  75                  80
```

```
Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 76
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 76

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 77
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 77

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
            35                  40                  45

Ser Gly Ile Ser Ser Ser Asp Gly Asn Thr Tyr Tyr Ala Asp Ser Val
50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125
```

-continued

<210> SEQ ID NO 78
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 78

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 79
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 80
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 80

Glu Val Gln Leu Val Glu Ser Gly Gly Gly Leu Val Gln Ala Gly Gly
1               5                   10                  15

-continued

```
Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 81
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 82
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
```

```
                 65                  70                  75                  80
Leu Gln Met Asn Ser Leu Arg Pro Glu Asp Thr Ala Val Tyr Tyr Cys
                 85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 83
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 83

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Gly Arg Glu Gly Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 84
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 84

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Gly Arg Glu Gly Val
            35                  40                  45

Ser Gly Ile Ser Ser Ser Asp Gly Asn Thr Tyr Tyr Ala Asp Ser Val
        50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125
```

```
<210> SEQ ID NO 85
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 86
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Leu Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 87
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 87

Glu Val Gln Leu Val Glu Ser Gly Gly Gly Leu Val Gln Ala Gly Gly
```

```
           1               5                  10                 15
Ser Leu Arg Leu Ser Cys Ala Ala Ser Gly Phe Thr Phe Asp Asp Tyr
                20                  25                 30

Asp Ile Gly Trp Val Arg Gln Ala Pro Gly Lys Glu Leu Glu Gly Val
            35                  40                 45

Ser Gly Ile Ser Ser Ser Asp Gly Asn Thr Tyr Tyr Ala Asp Ser Val
        50                  55                 60

Lys Gly Arg Phe Thr Ile Ser Ser Asp Asn Ala Lys Asn Thr Val Tyr
65                      70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                110

Phe Phe Lys Tyr Trp Gly Gln Gly Thr Leu Val Thr Val Ser Ser
            115                 120                 125
```

<210> SEQ ID NO 88
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 88

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Ser Asp Tyr
                20                  25                 30

Asp Ile Gly Trp Val Arg Gln Ala Pro Gly Lys Glu Leu Glu Gly Val
            35                  40                 45

Ser Gly Ile Ser Ser Ser Asp Gly Asn Thr Tyr Tyr Ala Asp Ser Val
        50                  55                 60

Lys Gly Arg Phe Thr Ile Ser Ser Asp Asn Ala Lys Asn Thr Val Tyr
65                      70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                110

Phe Phe Lys Tyr Trp Gly Gln Gly Thr Leu Val Thr Val Ser Ser
            115                 120                 125
```

<210> SEQ ID NO 89
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 89

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Asp Asp Tyr
                20                  25                 30

Asp Ile Gly Trp Phe Arg Gln Ala Pro Gly Lys Glu Leu Glu Gly Val
            35                  40                 45

Ser Gly Ile Ser Ser Ser Asp Gly Asn Thr Tyr Tyr Ala Asp Ser Val
        50                  55                 60
```

```
Lys Gly Arg Phe Thr Ile Ser Ser Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 90
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 90

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Asp Asp Tyr
                 20                  25                  30

Asp Ile Gly Trp Phe Arg Gln Ala Pro Gly Lys Glu Leu Glu Gly Val
             35                  40                  45

Ser Gly Ile Ser Ser Ser Asp Gly Asn Thr Tyr Tyr Ala Asp Ser Val
 50                  55                  60

Lys Gly Arg Phe Thr Ile Ser Ser Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 91
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 91

Glu Val Gln Leu Val Glu Ser Gly Gly Gly Leu Val Gln Ala Gly Gly
  1               5                  10                  15

Ser Leu Arg Leu Ser Cys Ala Ala Ser Gly Phe Thr Phe Asp Asp Tyr
                 20                  25                  30

Asp Ile Gly Trp Phe Arg Gln Ala Pro Gly Lys Glu Leu Glu Trp Val
             35                  40                  45

Ser Gly Ile Ser Ser Ser Asp Gly Asn Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125
```

<210> SEQ ID NO 92
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 92

Glu Val Gln Leu Val Glu Ser Gly Gly Gly Leu Val Gln Ala Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 93
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 93

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 94
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 94

-continued

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
50                  55                  60

Lys Gly Arg Phe Thr Ile Ser Ser Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125
```

<210> SEQ ID NO 95
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 95

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
50                  55                  60

Lys Gly Arg Phe Thr Ile Ser Ser Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125
```

<210> SEQ ID NO 96
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 96

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
50                  55                  60
```

Lys Gly Arg Phe Thr Ile Ser Ser Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 97
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 98
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser

<210> SEQ ID NO 99
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 99

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Glu Arg Glu Trp Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 100
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 101
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 101

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Gly Val
            35                  40                  45

Ser Gly Ile Ser Ser Ser Asp Gly Asn Thr Tyr Tyr Ala Asp Ser Val
50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 102
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 102

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Gly Arg Glu Gly Val
            35                  40                  45

Ser Gly Ile Ser Ser Ser Asp Gly Asn Thr Tyr Tyr Ala Asp Ser Val
50                  55                  60

Lys Gly Arg Phe Thr Ile Ser Ser Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 103
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
            35                  40                  45

Ser Gly Ile Ser Ser Ser Asp Gly Asn Thr Tyr Tyr Ala Asp Ser Val

```
                   50                    55                      60
Lys Gly Arg Phe Thr Ile Ser Ser Asp Asn Ala Lys Asn Thr Val Tyr
 65                    70                      75                    80

Leu Gln Met Asn Ser Leu Lys Ala Glu Asp Thr Ala Val Tyr Tyr Cys
                    85                      90                      95

Ala Arg Glu Pro Pro Asp Ser Ser Trp Tyr Leu Asp Gly Ser Pro Glu
                   100                     105                     110

Phe Phe Lys Tyr Trp Gly Gln Gly Thr Leu Val Thr Val Ser Ser
                   115                     120                     125

<210> SEQ ID NO 104
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 104

Glu Val Gln Leu Val Glu Ser Gly Gly Gly Leu Val Gln Pro Gly Gly
 1                   5                      10                      15

Ser Leu Arg Leu Ser Cys Ala Ala Ser Gly Phe Thr Phe Ser Asp Tyr
                    20                      25                      30

Asp Ile Gly Trp Phe Arg Gln Ala Pro Gly Lys Gly Arg Glu Gly Val
                    35                      40                      45

Ser Gly Ile Ser Ser Ser Asp Gly Asn Thr Tyr Tyr Ala Asp Ser Val
                    50                      55                      60

Lys Gly Arg Phe Thr Ile Ser Ser Asp Asn Ala Lys Asn Thr Val Tyr
 65                    70                      75                    80

Leu Gln Met Asn Ser Leu Lys Ala Glu Asp Thr Ala Val Tyr Tyr Cys
                    85                      90                      95

Ala Ala Glu Pro Pro Asp Ser Ser Trp Tyr Leu Asp Gly Ser Pro Glu
                   100                     105                     110

Phe Phe Lys Tyr Trp Gly Gln Gly Thr Leu Val Thr Val Ser Ser
                   115                     120                     125

<210> SEQ ID NO 105
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 105

Glu Val Gln Leu Val Glu Ser Gly Gly Gly Leu Val Gln Ala Gly Gly
 1                   5                      10                      15

Ser Leu Arg Leu Ser Cys Ala Ala Ser Gly Phe Thr Phe Asp Asp Tyr
                    20                      25                      30

Asp Ile Gly Trp Phe Arg Gln Ala Pro Gly Lys Gly Arg Glu Gly Val
                    35                      40                      45

Ser Gly Ile Ser Ser Ser Asp Gly Asn Thr Tyr Tyr Ala Asp Ser Val
                    50                      55                      60

Lys Gly Arg Phe Thr Ile Ser Ser Asp Asn Ala Lys Asn Thr Leu Tyr
 65                    70                      75                    80

Leu Gln Met Asn Ser Leu Lys Ala Glu Asp Thr Ala Val Tyr Tyr Cys
                    85                      90                      95

Ala Ala Glu Pro Pro Asp Ser Ser Trp Tyr Leu Asp Gly Ser Pro Glu
                   100                     105                     110
```

Phe Phe Lys Tyr Trp Gly Gln Gly Thr Leu Val Thr Val Ser Ser
            115                 120                 125

<210> SEQ ID NO 106
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 106

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 107
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 108
<211> LENGTH: 127
<212> TYPE: PRT
<213> ORGANISM: Artificial
<220> FEATURE:
<223> OTHER INFORMATION: Nanobody or Nanobody Fragment

```
<400> SEQUENCE: 108

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 109
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
        115                 120                 125

<210> SEQ ID NO 110
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 110

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45
```

```
Ser Gly Ile Ser Ser Ser Asp Gly Asn Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Ala Glu Asp Thr Ala Val Tyr Tyr Cys
                 85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
115                 120                 125

<210> SEQ ID NO 111
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 111

Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Gly Val
             35                  40                  45

Ser Gly Ile Ser Ser Ser Asp Gly Asn Thr Tyr Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ala Glu Asp Thr Ala Val Tyr Tyr Cys
                 85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
                115                 120                 125

<210> SEQ ID NO 112
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 112

Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Gly Val
             35                  40                  45

Ser Gly Ile Ser Ser Ser Asp Gly Asn Thr Tyr Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ala Glu Asp Thr Ala Val Tyr Tyr Cys
                 85                  90                  95

Ala Arg Glu Pro Pro Asp Ser Ser Trp Tyr Leu Asp Gly Ser Pro Glu
            100                 105                 110
```

Phe Phe Lys Tyr Trp Gly Gln Gly Thr Gln Val Thr Val Ser Ser
            115                 120                 125

<210> SEQ ID NO 113
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 113

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 114
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 114

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Val Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 115
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 116
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 117
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
            50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 118
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 118

Glu Val Gln Leu Val Glu Ser Gly Gly Gly Leu Val Gln Ala Gly Gly
 1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
            35                  40                  45

Ser Gly Ile Ser Ser Ser Asp Gly Asn Thr Tyr Tyr Ala Asp Ser Val
            50                  55                  60

Lys Gly Arg Phe Thr Ile Ser Asp Asn Ala Lys Asn Thr Leu Tyr
 65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125

<210> SEQ ID NO 119
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 119

Glu Val Gln Leu Val Glu Ser Gly Gly Gly Leu Val Gln Ala Gly Gly
 1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
            35                  40                  45

Ser Gly Ile Ser Ser Ser Asp Gly Asn Thr Tyr Tyr Ala Asp Ser Val
            50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu

```
                100             105             110
Phe Phe Lys Tyr Trp Gly Gln Gly Thr Gln Val Thr Val Ser Ser
            115             120             125

<210> SEQ ID NO 120
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 120

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Glu Pro Pro Asp Ser Ser Trp Tyr Leu Asp Gly Ser Pro Glu
            100             105             110

Phe Phe Lys Tyr Trp Gly Gln Gly Thr Leu Val Thr Val Ser Ser
            115             120             125

<210> SEQ ID NO 121
<211> LENGTH: 127
<212> TYPE: PRT
<213> ORGANISM: Artificial
<220> FEATURE:
<223> OTHER INFORMATION: Nanobody or Nanobody Fragment

<400> SEQUENCE: 121

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Glu Pro Pro Asp Ser Ser Trp Tyr Leu Asp Gly Ser Pro Glu
            100             105             110

Phe Phe Lys Tyr Trp Gly Gln Gly Thr Leu Val Thr Val Ser Ser
            115             120             125

<210> SEQ ID NO 122
<211> LENGTH: 121
<212> TYPE: PRT
<213> ORGANISM: Artificial
<220> FEATURE:
```

<223> OTHER INFORMATION: Nanobody or Nanobody Fragment

<400> SEQUENCE: 122

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120
```

<210> SEQ ID NO 123
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 123

```
Glu Val Gln Leu Val Glu Ser Gly Gly Gly Leu Val Gln Pro Gly Gly
1               5                   10                  15

Ser Leu Arg Leu Thr Cys Ala Ala Ser Gly Thr Ile Phe Lys Val Asn
            20                  25                  30

Val Met Ala Trp Tyr Arg Gln Ala Pro Gly Lys Gly Arg Glu Leu Val
        35                  40                  45

Ala Ala Ile Ile Thr Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120
```

<210> SEQ ID NO 124
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 124

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Val Asn
            20                  25                  30

Val Met Ala Trp Tyr Arg Gln Ala Pro Gly Lys Gly Arg Glu Leu Val
```

```
                35                  40                  45
Ala Gly Ile Ile Asn Gly Gly Ser Thr Thr Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 125
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 125

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Lys Ile Asn
                20                  25                  30

Val Met Ala Trp Tyr Arg Gln Ala Pro Gly Lys Gly Arg Glu Leu Val
                35                  40                  45

Ala Ala Ile Ile Asn Gly Gly Thr Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 126
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 126

Glu Val Gln Leu Val Glu Ser Gly Gly Gly Leu Val Gln Pro Gly Gly
 1               5                  10                  15

Ser Leu Arg Leu Ser Cys Ala Ala Ser Gly Thr Ile Phe Lys Leu Asn
                20                  25                  30

Val Met Ala Trp Tyr Arg Gln Ala Pro Gly Lys Gly Arg Glu Leu Val
                35                  40                  45

Ala Ala Ile Ile Thr Gly Gly Thr Thr Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95
```

Phe Val Thr Thr Asn Ser Asp Tyr Asp Leu Gly Arg Asp Tyr Trp Gly
              100                 105                 110

Gln Gly Thr Leu Val Thr Val Ser Ser
        115                 120

<210> SEQ ID NO 127
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg Val Asn
            20                  25                  30

Val Met Ala Trp Tyr Arg Gln Ala Pro Gly Lys Gly Arg Glu Leu Val
        35                  40                  45

Ala Ala Ile Ile Ser Gly Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
              100                 105                 110

Gln Gly Thr Leu Val Thr Val Ser Ser
        115                 120

<210> SEQ ID NO 128
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Lys Ile Asn
            20                  25                  30

Ile Met Ala Trp Tyr Arg Gln Ala Pro Gly Lys Gly Arg Glu Leu Val
        35                  40                  45

Ala Ala Ile Ile Asn Ser Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
              100                 105                 110

Gln Gly Thr Leu Val Thr Val Ser Ser
        115                 120

<210> SEQ ID NO 129
<211> LENGTH: 121
<212> TYPE: PRT
<213> ORGANISM: Artificial

```
<220> FEATURE:
<223> OTHER INFORMATION: Nanobody or Nanobody Fragment

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ala Phe Lys Val Asn
            20                  25                  30

Val Met Ala Trp Tyr Arg Gln Ala Pro Gly Lys Gly Arg Glu Leu Val
        35                  40                  45

Ala Gly Val Ile Thr Asp Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 130
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Val Met Ala Trp Tyr Arg Gln Ala Pro Gly Lys Gly Arg Glu Leu Val
        35                  40                  45

Ala Ala Ile Ile Thr Ser Gly Thr Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 131
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ser Gly Thr Thr Phe Lys Ile Asn
            20                  25                  30
```

```
Val Met Ala Trp Tyr Arg Gln Ala Pro Gly Lys Gly Arg Glu Leu Val
            35                  40                  45

Ala Ala Ile Ile Thr Gly Thr Thr Thr Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
            115                 120

<210> SEQ ID NO 132
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 132

Glu Val Gln Leu Val Glu Ser Gly Gly Gly Leu Val Gln Pro Gly Gly
 1               5                  10                  15

Ser Leu Arg Leu Ser Cys Ala Ala Ser Gly Thr Thr Phe Arg Ile Asn
            20                  25                  30

Val Met Ala Trp Tyr Arg Gln Ala Pro Gly Lys Gly Arg Glu Leu Val
            35                  40                  45

Ala Gly Ile Ile Thr Asn Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
            115                 120

<210> SEQ ID NO 133
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 133

Glu Val Gln Leu Val Glu Ser Gly Gly Gly Leu Val Gln Pro Gly Gly
 1               5                  10                  15

Ser Leu Arg Leu Ser Cys Ala Ala Asn Gly Thr Thr Phe Lys Val Asn
            20                  25                  30

Val Met Ala Trp Tyr Arg Gln Ala Pro Gly Lys Gly Arg Glu Leu Val
            35                  40                  45

Ala Gly Val Ile Thr Gly Gly Thr Thr Asn Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95
```

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 134
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Val Asn
            20                  25                  30

Ile Met Ala Trp Tyr Arg Gln Ala Pro Gly Lys Gly Arg Glu Leu Val
        35                  40                  45

Ala Ala Ile Ile Thr Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 135
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg Leu Asn
            20                  25                  30

Val Met Ala Trp Tyr Arg Gln Ala Pro Gly Lys Gly Arg Glu Leu Val
        35                  40                  45

Ala Ala Ile Ile Thr Asn Gly Thr Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 136
<211> LENGTH: 121
<212> TYPE: PRT

```
<213> ORGANISM: Artificial
<220> FEATURE:
<223> OTHER INFORMATION: Nanobody or Nanobody Fragment

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Val Met Ala Trp Tyr Arg Gln Ala Pro Gly Lys Gly Arg Glu Leu Val
        35                  40                  45

Ala Ala Ile Ile Ser Gly Gly Ser Thr Pro Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 137
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Val Met Ala Trp Tyr Arg Gln Ala Pro Gly Lys Gly Arg Glu Leu Val
        35                  40                  45

Ala Ala Ile Ile Thr Gly Gly Thr Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 138
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 138

Glu Val Gln Leu Val Glu Ser Gly Gly Gly Leu Val Gln Pro Gly Gly
1               5                   10                  15

Ser Leu Arg Leu Thr Cys Ala Ala Ser Gly Thr Thr Phe Lys Val Asn
            20                  25                  30
```

```
Val Met Ala Trp Tyr Arg Gln Ala Pro Gly Lys Gly Arg Glu Leu Val
        35                  40                  45

Ala Ala Val Ile Asn Gly Gly Thr Thr Ser Tyr Ala Asp Ser Val Lys
50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 139
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Arg Ile Asn
            20                  25                  30

Val Met Ala Trp Tyr Arg Gln Ala Pro Gly Lys Gly Arg Glu Leu Val
        35                  40                  45

Ala Ala Ile Ile Ser Gly Gly Ser Thr Thr Tyr Ala Asp Ser Val Lys
50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 140
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Val Met Ala Trp Tyr Arg Gln Ala Pro Gly Lys Gly Arg Lys Leu Val
        35                  40                  45

Ala Ala Ile Ile Asn Asn Gly Asn Thr Thr Tyr Ala Asp Ser Val Lys
50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
```

```
                     85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 141
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Val Phe Lys Val Asn
            20                  25                  30

Ala Met Ala Trp Tyr Arg Gln Ala Pro Gly Lys Gly Arg Glu Leu Val
        35                  40                  45

Ala Gly Val Ile Ser Ala Gly Ser Ala Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 142
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Tyr Arg Ile Asn
            20                  25                  30

Ala Met Gly Trp Tyr Arg Gln Ala Pro Gly Lys Gly Arg Glu Leu Val
        35                  40                  45

Ala Gly Leu Ile Ser Ala Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 143
<211> LENGTH: 121
```

<212> TYPE: PRT
<213> ORGANISM: Artificial
<220> FEATURE:
<223> OTHER INFORMATION: Nanobody or Nanobody Fragment

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg Ile Asn
            20                  25                  30

Ile Met Ala Trp Tyr Arg Gln Ala Pro Gly Lys Gly Arg Glu Leu Val
        35                  40                  45

Ala Gly Val Ile Thr Ser Gly Asn Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 144
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Arg Val Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 145
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Lys Val Asn

```
            20                  25                  30
Ile Met Ala Trp Tyr Arg Gln Ala Pro Gly Lys Gly Arg Glu Leu Val
            35                  40                  45

Ala Ala Ile Ile Thr Ser Gly Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
            115                 120
```

<210> SEQ ID NO 146
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 146

```
Glu Val Gln Leu Val Glu Ser Gly Gly Gly Leu Val Gln Pro Gly Gly
1               5                   10                  15

Thr Leu Arg Leu Ser Cys Ala Ala Ser Gly Ser Thr Phe Lys Ile Asn
            20                  25                  30

Val Met Ala Trp Tyr Arg Gln Ala Pro Gly Lys Gly Arg Glu Leu Val
            35                  40                  45

Ala Gly Val Ile Thr Asn Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
            115                 120
```

<210> SEQ ID NO 147
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 147

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Leu Asn
            20                  25                  30

Ile Met Ala Trp Tyr Arg Gln Ala Pro Gly Lys Gly Arg Glu Leu Val
            35                  40                  45

Ala Ala Val Ile Asn Gly Gly Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80
```

Gln Met Asn Ser Leu Arg Pro Glu Asp Thr Ala Val Tyr Tyr Cys Ala
            85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 148
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
            85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 149
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg Ile Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
            85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 150

<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg Ile Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Thr Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 151
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Ile Asn
            20                  25                  30

Val Met Ala Trp Tyr Arg Gln Ala Pro Gly Lys Gly Arg Glu Leu Val
        35                  40                  45

Ala Ala Ile Ile Asn Gly Gly Thr Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 152
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg Ile Asn
            20                  25                  30

Val Met Ala Trp Tyr Arg Gln Ala Pro Gly Lys Gly Arg Glu Leu Val
        35                  40                  45

Ala Gly Val Ile Asn Asp Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 153
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Ile Met Ala Trp Tyr Arg Gln Ala Pro Gly Lys Gly Arg Glu Leu Val
        35                  40                  45

Ala Gly Val Ile Asn Ser Gly Thr Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 154
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Lys Ile Asn
            20                  25                  30

Ile Met Ala Trp Tyr Arg Gln Ala Pro Gly Lys Gly Arg Glu Leu Val
        35                  40                  45

Ala Gly Val Ile Thr Gly Gly Asn Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
               100                 105                 110

Gln Gly Thr Leu Val Thr Val Ser Ser
        115                 120

<210> SEQ ID NO 155
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Lys Ile Asn
            20                  25                  30

Ile Met Ala Trp Tyr Arg Gln Ala Pro Gly Lys Gly Arg Glu Leu Val
        35                  40                  45

Ala Ala Ile Ile Asn Ser Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
               100                 105                 110

Gln Gly Thr Leu Val Thr Val Ser Ser
        115                 120

<210> SEQ ID NO 156
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Val Asn
            20                  25                  30

Val Met Ala Trp Tyr Arg Gln Ala Pro Gly Lys Gly Arg Glu Leu Val
        35                  40                  45

Ala Ala Val Ile Asn Gly Gly Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
               100                 105                 110

Gln Gly Thr Leu Val Thr Val Ser Ser
        115                 120

```
<210> SEQ ID NO 157
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 157
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Ala Met Gly Trp Tyr Arg Gln Ala Pro Gly Lys Gly Arg Glu Leu Val
        35                  40                  45

Ala Gly Leu Ile Ser Ala Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

```
<210> SEQ ID NO 158
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 158
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg Ile Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

```
<210> SEQ ID NO 159
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 159
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg Leu Asn
            20                  25                  30

Val Met Ala Trp Tyr Arg Gln Ala Pro Gly Lys Gly Arg Glu Leu Val
        35                  40                  45

Ala Ala Ile Ile Thr Ser Gly Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
            115                 120

<210> SEQ ID NO 160
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Ile Asn
            20                  25                  30

Val Met Ala Trp Tyr Arg Gln Ala Pro Gly Lys Gly Arg Glu Leu Val
        35                  40                  45

Ala Ala Ile Ile Asn Gly Gly Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
            115                 120

<210> SEQ ID NO 161
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Val Asn
            20                  25                  30

Val Met Ala Trp Tyr Arg Gln Ala Pro Gly Lys Gly Arg Glu Leu Val
        35                  40                  45

Ala Ala Ile Ile Asn Asp Gly Ser Thr Tyr Ala Asp Ser Val Lys
    50                  55                  60

Gly Arg Phe Thr Ile Ser Arg Asp Asn Ala Lys Asn Thr Leu Tyr Leu

```
                65                  70                  75                  80
Gln Met Asn Ser Leu Arg Pro Glu Asp Thr Ala Val Tyr Tyr Cys Ala
                    85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
                115                 120

<210> SEQ ID NO 162
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Arg Val Asn
                20                  25                  30

Val Met Ala Trp Tyr Arg Gln Ala Pro Gly Lys Gly Arg Glu Leu Val
            35                  40                  45

Ala Ala Ile Ile Thr Asp Gly Thr Thr Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                    85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
                115                 120

<210> SEQ ID NO 163
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 163

Glu Val Gln Leu Val Glu Ser Gly Gly Gly Leu Val Gln Pro Gly Gly
1               5                   10                  15

Ser Leu His Leu Ser Cys Ala Ala Ser Gly Thr Ile Phe Lys Ile Asn
                20                  25                  30

Val Met Ala Trp Tyr Arg Gln Ala Pro Gly Lys Gly Arg Glu Leu Val
            35                  40                  45

Ala Ala Ile Ile Thr Asp Gly Ser Thr Thr Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                    85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
                115                 120
```

<210> SEQ ID NO 164
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Val Asn
            20                  25                  30

Ile Met Ala Trp Tyr Arg Gln Ala Pro Gly Lys Gly Arg Glu Leu Val
        35                  40                  45

Ala Ala Ile Ile Thr Asn Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 165
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Asn Gly Ser Val Tyr Lys Val Asn
            20                  25                  30

Ala Met Ala Trp Tyr Arg Gln Ala Pro Gly Lys Gly Arg Glu Leu Val
        35                  40                  45

Ala Gly Ile Val Thr Gly Gly Thr Ser Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 166
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 166

Glu Val Gln Leu Val Glu Ser Gly Gly Gly Leu Val Gln Pro Gly Gly

```
                1               5                  10                 15
            Ser Leu Arg Leu Ser Cys Ala Ala Ser Gly Thr Thr Phe Lys Ile Asn
                           20                  25                  30

Val Met Ala Trp Tyr Arg Gln Ala Pro Gly Lys Gly Arg Glu Leu Val
                           35                  40                  45

Ala Gly Ile Ile Thr Gly Gly Thr Thr Tyr Ala Asp Ser Val Lys
                           50                  55                  60

Gly Arg Phe Thr Ile Ser Arg Asp Asn Ala Lys Asn Thr Leu Tyr Leu
             65                 70                  75                  80

Gln Met Asn Ser Leu Arg Pro Glu Asp Thr Ala Val Tyr Tyr Cys Ala
                           85                  90                  95

Phe Val Thr Thr Asn Ser Asp Tyr Asp Leu Gly Arg Asp Tyr Trp Gly
                           100                 105                 110

Gln Gly Thr Leu Val Thr Val Ser Ser
                           115                 120

<210> SEQ ID NO 167
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 167

Glu Val Gln Leu Val Glu Ser Gly Gly Gly Leu Val Gln Pro Gly Gly
             1               5                  10                 15

Ser Leu Arg Leu Ser Cys Ala Ala Ser Gly Ser Val Phe Arg Ile Asn
                           20                  25                  30

Ala Met Ala Trp Tyr Arg Gln Ala Pro Gly Lys Gly Arg Glu Leu Val
                           35                  40                  45

Ala Gly Phe Val Thr Gly Gly Ser Asn Tyr Ala Asp Ser Val Lys
                           50                  55                  60

Gly Arg Phe Thr Ile Ser Arg Asp Asn Ala Lys Asn Thr Leu Tyr Leu
             65                 70                  75                  80

Gln Met Asn Ser Leu Arg Pro Glu Asp Thr Ala Val Tyr Tyr Cys Ala
                           85                  90                  95

Phe Val Thr Thr Asn Ser Asp Tyr Asp Leu Gly Arg Asp Tyr Trp Gly
                           100                 105                 110

Gln Gly Thr Leu Val Thr Val Ser Ser
                           115                 120

<210> SEQ ID NO 168
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 168

Glu Val Gln Leu Val Glu Ser Gly Gly Gly Leu Val Gln Pro Gly Gly
             1               5                  10                 15

Ser Leu Arg Leu Ser Cys Ala Ala Ser Gly Ser Ile Phe Lys Ile Asn
                           20                  25                  30

Val Met Ala Trp Tyr Arg Gln Ala Pro Gly Lys Gly Arg Glu Leu Val
                           35                  40                  45

Ala Ala Ile Ile Asn Ser Gly Thr Thr Ser Tyr Ala Asp Ser Val Lys
                           50                  55                  60
```

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 169
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Ile Met Ala Trp Tyr Arg Gln Ala Pro Gly Lys Gly Arg Glu Leu Val
        35                  40                  45

Ala Gly Val Ile Thr Gly Gly Asn Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 170
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Val Asn
            20                  25                  30

Val Met Ala Trp Tyr Arg Gln Ala Pro Gly Lys Gly Arg Glu Leu Val
        35                  40                  45

Ala Gly Ile Ile Thr Gly Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 171
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 171

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Val Phe Lys Ile Asn
            20                  25                  30

Ala Met Ala Trp Tyr Arg Gln Ala Pro Gly Lys Gly Arg Glu Leu Val
        35                  40                  45

Ala Gly Leu Val Ser Ala Gly Thr Ala Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120
```

<210> SEQ ID NO 172
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 172

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Ala Asp Thr Asp Tyr Asp Leu Gly Lys Arg Tyr Trp Gly
            100                 105                 110

Gln Gly Thr Leu Val Thr Val Ser Ser
        115                 120
```

<210> SEQ ID NO 173
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Ala Asp Thr Asp Tyr Asp Leu Gly Lys Arg Tyr Trp Gly
                100                 105                 110

Gln Gly Thr Leu Val Thr Val Ser Ser
        115                 120

<210> SEQ ID NO 174
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Asp Thr Asn Tyr Asp Leu Gly Lys Arg Ser Trp Gly
                100                 105                 110

Gln Gly Thr Leu Val Thr Val Ser Ser
        115                 120

<210> SEQ ID NO 175
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Ala Ser Asn Ser Glu Tyr Asp Leu Gly Arg Arg Phe Trp Gly
            100                 105                 110

Gln Gly Thr Leu Val Thr Val Ser Ser
        115                 120

<210> SEQ ID NO 176
<211> LENGTH: 121
<212> TYPE: PRT
<213> ORGANISM: Artificial
<220> FEATURE:
<223> OTHER INFORMATION: Nanobody or Nanobody Fragment

<400> SEQUENCE: 176

Glu Val Gln Leu Val Glu Ser Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Ala Asp Thr Glu Tyr Asp Leu Gly Lys Arg Phe Trp Gly
            100                 105                 110

Gln Gly Thr Leu Val Thr Val Ser Ser
        115                 120

<210> SEQ ID NO 177
<211> LENGTH: 4
<212> TYPE: PRT
<213> ORGANISM: Artificial Sequence
<220> FEATURE:
<223> OTHER INFORMATION: GLEW group sequence

<400> SEQUENCE: 177

Gly Leu Glu Trp
1

<210> SEQ ID NO 178
<211> LENGTH: 4
<212> TYPE: PRT
<213> ORGANISM: Artificial Sequence
<220> FEATURE:
<223> OTHER INFORMATION: KERE group sequence

<400> SEQUENCE: 178

Lys Glu Arg Glu
1

<210> SEQ ID NO 179
<211> LENGTH: 4
<212> TYPE: PRT
<213> ORGANISM: Artificial Sequence
<220> FEATURE:

<223> OTHER INFORMATION: KERE group sequence

<400> SEQUENCE: 179

Lys Gln Arg Glu
1

<210> SEQ ID NO 180
<211> LENGTH: 5
<212> TYPE: PRT
<213> ORGANISM: Artificial Sequence
<220> FEATURE:
<223> OTHER INFORMATION: KERE group sequence

<400> SEQUENCE: 180

Lys Glu Arg Glu Leu
1               5

<210> SEQ ID NO 181
<211> LENGTH: 5
<212> TYPE: PRT
<213> ORGANISM: Artificial Sequence
<220> FEATURE:
<223> OTHER INFORMATION: KERE group sequence

<400> SEQUENCE: 181

Lys Glu Arg Glu Phe
1               5

<210> SEQ ID NO 182
<211> LENGTH: 5
<212> TYPE: PRT
<213> ORGANISM: Artificial Sequence
<220> FEATURE:
<223> OTHER INFORMATION: KERE group sequence

<400> SEQUENCE: 182

Lys Gln Arg Glu Leu
1               5

<210> SEQ ID NO 183
<211> LENGTH: 5
<212> TYPE: PRT
<213> ORGANISM: Artificial Sequence
<220> FEATURE:
<223> OTHER INFORMATION: KERE group sequence

<400> SEQUENCE: 183

Lys Gln Arg Glu Phe
1               5

<210> SEQ ID NO 184
<211> LENGTH: 5
<212> TYPE: PRT
<213> ORGANISM: Artificial Sequence
<220> FEATURE:
<223> OTHER INFORMATION: KERE group Sequence

<400> SEQUENCE: 184

Lys Glu Arg Glu Gly
1               5

<210> SEQ ID NO 185
<211> LENGTH: 4
<212> TYPE: PRT
<213> ORGANISM: Artificial Sequence
<220> FEATURE:
<223> OTHER INFORMATION: KERE group sequence

<400> SEQUENCE: 185

Thr Glu Arg Glu
1

<210> SEQ ID NO 186
<211> LENGTH: 5
<212> TYPE: PRT
<213> ORGANISM: Artificial Sequence
<220> FEATURE:
<223> OTHER INFORMATION: KERE group sequence

<400> SEQUENCE: 186

Thr Glu Arg Glu Leu
1               5

<210> SEQ ID NO 187
<211> LENGTH: 4
<212> TYPE: PRT
<213> ORGANISM: Artificial Sequence
<220> FEATURE:
<223> OTHER INFORMATION: KERE group sequence

<400> SEQUENCE: 187

Lys Glu Cys Glu
1

<210> SEQ ID NO 188
<211> LENGTH: 5
<212> TYPE: PRT
<213> ORGANISM: Artificial Sequence
<220> FEATURE:
<223> OTHER INFORMATION: KERE group sequence

<400> SEQUENCE: 188

Lys Glu Cys Glu Leu
1               5

<210> SEQ ID NO 189
<211> LENGTH: 5
<212> TYPE: PRT
<213> ORGANISM: Artificial Sequence
<220> FEATURE:
<223> OTHER INFORMATION: KERE group sequence

<400> SEQUENCE: 189

Lys Glu Cys Glu Arg
1               5

<210> SEQ ID NO 190
<211> LENGTH: 4
<212> TYPE: PRT
<213> ORGANISM: Artificial Sequence
<220> FEATURE:
<223> OTHER INFORMATION: KERE group sequence

<400> SEQUENCE: 190

Arg Glu Arg Glu
1

<210> SEQ ID NO 191
<211> LENGTH: 5
<212> TYPE: PRT
<213> ORGANISM: Artificial Sequence
<220> FEATURE:
<223> OTHER INFORMATION: KERE group sequence

```
<400> SEQUENCE: 191

Arg Glu Arg Glu Gly
1               5

<210> SEQ ID NO 192
<211> LENGTH: 4
<212> TYPE: PRT
<213> ORGANISM: Artificial Sequence
<220> FEATURE:
<223> OTHER INFORMATION: KERE group sequence

<400> SEQUENCE: 192

Gln Glu Arg Glu
1

<210> SEQ ID NO 193
<211> LENGTH: 5
<212> TYPE: PRT
<213> ORGANISM: Artificial Sequence
<220> FEATURE:
<223> OTHER INFORMATION: KERE group sequence

<400> SEQUENCE: 193

Gln Glu Arg Glu Gly
1               5

<210> SEQ ID NO 194
<211> LENGTH: 4
<212> TYPE: PRT
<213> ORGANISM: Artificial Sequence
<220> FEATURE:
<223> OTHER INFORMATION: KERE group sequence

<400> SEQUENCE: 194

Lys Gly Arg Glu
1

<210> SEQ ID NO 195
<211> LENGTH: 5
<212> TYPE: PRT
<213> ORGANISM: Artificial Sequence
<220> FEATURE:
<223> OTHER INFORMATION: KERE group sequence

<400> SEQUENCE: 195

Lys Gly Arg Glu Gly
1               5

<210> SEQ ID NO 196
<211> LENGTH: 4
<212> TYPE: PRT
<213> ORGANISM: Artificial Sequence
<220> FEATURE:
<223> OTHER INFORMATION: KERE group sequence

<400> SEQUENCE: 196

Lys Asp Arg Glu
1

<210> SEQ ID NO 197
<211> LENGTH: 5
<212> TYPE: PRT
<213> ORGANISM: Artificial Sequence
<220> FEATURE:
<223> OTHER INFORMATION: KERE group sequence

<400> SEQUENCE: 197
```

Lys Asp Arg Glu Val
1               5

<210> SEQ ID NO 198
<211> LENGTH: 5
<212> TYPE: PRT
<213> ORGANISM: Artificial Sequence
<220> FEATURE:
<223> OTHER INFORMATION: KERE group sequence

<400> SEQUENCE: 198

Asp Glu Cys Lys Leu
1               5

<210> SEQ ID NO 199
<211> LENGTH: 5
<212> TYPE: PRT
<213> ORGANISM: Artificial Sequence
<220> FEATURE:
<223> OTHER INFORMATION: KERE group sequence

<400> SEQUENCE: 199

Asn Val Cys Glu Leu
1               5

<210> SEQ ID NO 200
<211> LENGTH: 4
<212> TYPE: PRT
<213> ORGANISM: Artificial Sequence
<220> FEATURE:
<223> OTHER INFORMATION: GLEW group sequence

<400> SEQUENCE: 200

Gly Val Glu Trp
1

<210> SEQ ID NO 201
<211> LENGTH: 4
<212> TYPE: PRT
<213> ORGANISM: Artificial Sequence
<220> FEATURE:
<223> OTHER INFORMATION: GLEW group sequence

<400> SEQUENCE: 201

Glu Pro Glu Trp
1

<210> SEQ ID NO 202
<211> LENGTH: 4
<212> TYPE: PRT
<213> ORGANISM: Artificial Sequence
<220> FEATURE:
<223> OTHER INFORMATION: GLEW group sequence

<400> SEQUENCE: 202

Gly Leu Glu Arg
1

<210> SEQ ID NO 203
<211> LENGTH: 4
<212> TYPE: PRT
<213> ORGANISM: Artificial Sequence
<220> FEATURE:
<223> OTHER INFORMATION: GLEW group sequence

<400> SEQUENCE: 203

Asp Gln Glu Trp
1

<210> SEQ ID NO 204
<211> LENGTH: 4
<212> TYPE: PRT
<213> ORGANISM: Artificial Sequence
<220> FEATURE:
<223> OTHER INFORMATION: GLEW group sequence

<400> SEQUENCE: 204

Asp Leu Glu Trp
1

<210> SEQ ID NO 205
<211> LENGTH: 4
<212> TYPE: PRT
<213> ORGANISM: Artificial Sequence
<220> FEATURE:
<223> OTHER INFORMATION: GLEW group sequence

<400> SEQUENCE: 205

Gly Ile Glu Trp
1

<210> SEQ ID NO 206
<211> LENGTH: 4
<212> TYPE: PRT
<213> ORGANISM: Artificial Sequence
<220> FEATURE:
<223> OTHER INFORMATION: GLEW group sequence

<400> SEQUENCE: 206

Glu Leu Glu Trp
1

<210> SEQ ID NO 207
<211> LENGTH: 4
<212> TYPE: PRT
<213> ORGANISM: Artificial Sequence
<220> FEATURE:
<223> OTHER INFORMATION: GLEW group sequence

<400> SEQUENCE: 207

Gly Pro Glu Trp
1

<210> SEQ ID NO 208
<211> LENGTH: 4
<212> TYPE: PRT
<213> ORGANISM: Artificial Sequence
<220> FEATURE:
<223> OTHER INFORMATION: GLEW group sequence

<400> SEQUENCE: 208

Glu Trp Leu Pro
1

<210> SEQ ID NO 209
<211> LENGTH: 4
<212> TYPE: PRT
<213> ORGANISM: Artificial Sequence
<220> FEATURE:
<223> OTHER INFORMATION: GLEW group sequence

<400> SEQUENCE: 209

Gly Pro Glu Arg

```
1

<210> SEQ ID NO 210
<211> LENGTH: 4
<212> TYPE: PRT
<213> ORGANISM: Artificial Sequence
<220> FEATURE:
<223> OTHER INFORMATION: GLEW group sequence

<400> SEQUENCE: 210

Lys Leu Glu Trp
1
```

PROVIDING IMPROVED IMMUNOGLOBULIN SEQUENCES BY MUTATING CDR AND/OR FR POSITIONS

RELATED APPLICATIONS

This application is a national stage filing under 35 U.S.C. § 371 of international application PCT/EP2008/058617, filed Jul. 3, 2008, which was published under PCT Article 21(2) in English, and claims the benefit under 35 U.S.C. § 119(e) of U.S. provisional application Ser. No. 60/958,164, filed Jul. 3, 2007, the disclosures of which are incorporated by reference herein in their entireties.

The present invention relates to methods and techniques for providing improved amino acid sequences that can be used as single antigen-binding domains.

In particular, the invention relates to methods and techniques for providing improved amino acid sequences that can be used as single antigen-binding domains that comprise or essentially consist of at least one immunoglobulin sequence. More in particular, the amino acid sequences provided herein may comprise or essentially consist of at least one variable domain sequence or a suitable fragment thereof, such as at least one light chain variable domain sequence (e.g. a $V_L$-sequence) or a suitable fragment thereof, or at least one heavy chain variable domain sequence (e.g. a $V_H$-sequence or $V_{HH}$ sequence) or a suitable fragment thereof.

The methods of the invention are particularly suited for providing improved domain antibodies (or amino acid sequences that are suitable for use as a domain antibody), single domain antibodies (or amino acid sequences that is suitable for use as a single domain antibody), "dAb's" (or amino acid sequences that are suitable for use as a dAb) or Nanobodies™ (as defined herein, and including but not limited to a $V_{HH}$ sequence). [Note: Nanobody™, Nanobodies™ and Nanoclone™ are trademarks of Ablynx N. V.].

The invention also relates to the improved amino acid sequences that can be generated using the methods of invention, as well as to nucleotide sequences or nucleic acids encoding the same (accordingly, the term "sequence" as used herein can refer to an amino acid sequence, to the corresponding nucleotide sequence/nucleic acid, or to both, as the context requires. Also, the terms "nucleotide sequence" as used herein also encompasses a nucleic acid molecule with said nucleotide sequence, so that the terms "nucleotide sequence" and "nucleic acid" should be considered equivalent and are used interchangeably herein).

The invention also relates to proteins or polypeptides that comprise or essentially consist of one or more of immunoglobulin sequences of the invention.

Other aspects, embodiments, advantages and applications of the invention will become clear from the further description herein.

Assembly PCR is a well-known technique for generating nucleotide sequences that encode large proteins or polypeptides (Stemmer et al., Gene, 1995, 164(1), 49-53). Generally, assembly PCR involves the single-step synthesis of a gene encoding a desired protein or polypeptide by performing a PCR reaction using a set of overlapping oligonucleotides (i.e. primers with short overlapping segments). The oligonucleotides used as primers for the assembly are a mixture of partly overlapping sense and antisense primers, in which the overlapping segments serve to order the PCR fragments so that they selectively assemble into the complete nucleotide sequence, which can then be expressed to provide the desired protein or polypeptide.

Assembly PCR is now routinely used for the preparation of desired proteins and polypeptides (also on a commercial basis), and has for example been used for the preparation of so-called ScFv's (see for example Deng et al., Clinical and Diagnostic Laboratory Immunology, July 2003, 587-595).

Proteins and polypeptides that comprise one or more immunoglobulin single variable domains, in which each single variable domain forms a single functional antigen-binding unit (i.e. without the interaction with another variable domain being required, as is the case for conventional $V_H/V_L$ domains, which have to interact to form a single antigen binding site), are known in the art. Examples of single variable domains that can be used in such proteins or polypeptides include domain antibodies, single domain antibodies and "dAb's", for which reference is for example made EP 0 368 684; Ward et al. (Nature 1989 Oct. 12; 341 (6242): 544-6); Holt et al., Trends Biotechnol., 2003, 21(11): 484-490; WO 06/030220; WO 06/003388 and other published patent applications of Domantis Ltd., which describe the (single) domain antibodies that are also referred to as "dAb's". Single domain antibodies that are derived from certain species of shark are also known (for example, the so-called "IgNAR domains", see for example WO 05/18629).

Nanobodies™ form a particularly preferred class of amino acid sequences that can be used as single variable domains. For a further description of Nanobodies, reference is made to the further disclosure herein, to the prior art mentioned herein, as well as to for example the review article by Muyldermans in Reviews in Molecular Biotechnology 74(2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372. WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference.

In accordance with the terminology used in the art (see the above references), the variable domains present in naturally occurring heavy chain antibodies will also be referred to as "$V_{HH}$ domains", in order to distinguish them from the heavy chain variable domains that are present in conventional 4-chain antibodies (which will be referred to hereinbelow as "$V_H$ domains") and from the light chain variable domains that are present in conventional 4-chain antibodies (which will be referred to hereinbelow as "$V_L$ domains").

As mentioned in this prior art, $V_{HH}$ domains (as well as Nanobodies based thereon, which share these structural characteristics and functional properties with the naturally occurring $V_{HH}$ domains) have a number of unique structural characteristics and functional properties which make isolated $V_{HH}$ domains. Nanobodies and proteins and polypeptides containing the same highly advantageous for use as functional antigen-binding domains or proteins. In particular, and without being limited thereto, $V_{HH}$ domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a $V_H$ domain covalently linked to a $V_L$ domain).

Because of these unique properties, the use of $V_{HH}$ domains and Nanobodies as single antigen-binding proteins or as antigen-binding domains (i.e. as part of a larger protein or polypeptide) offers a number of significant advantages over the use of conventional $V_{11}$ and $V_L$ domains, scFv's or conventional antibody fragments (such as Fab- or $F(ab')_2$-fragments):

- only a single domain is required to bind an antigen with high affinity and with high selectivity, so that there is no need to have two separate domains present, nor to assure that these two domains are present in the right spacial conformation and configuration (i.e. through the use of especially designed linkers, as with scFv's);
- $V_{HH}$ domains and Nanobodies can be expressed from a single gene and require no post-translational folding or modifications;
- $V_{HH}$ domains and Nanobodies can easily be engineered into multivalent and multispecific formats (as further discussed herein);
- $V_{HH}$ domains and Nanobodies are highly soluble and do not have a tendency to aggregate (as with the mouse-derived "dAb's" described by Ward et al., Nature. Vol. 341, 1989, p. 544);
- $V_{HH}$ domains and Nanobodies are highly stable to heat, pH, proteases and other denaturing agents or conditions (see for example Ewert et al. supra);
- $V_{HH}$ domains and Nanobodies are easy and relatively cheap to prepare, even on a scale required for production. For example, $V_{HH}$ domains, Nanobodies and proteins/polypeptides containing the same can be produced using microbial fermentation (e.g. as further described below) and do not require the use of mammalian expression systems, as with for example conventional antibody fragments;
- $V_{HH}$ domains and Nanobodies are relatively small (approximately 15 kDa, or 10 times smaller than a conventional IgG) compared to conventional 4-chain antibodies and antigen-binding fragments thereof, and therefore show high(er) penetration into tissues (including but not limited to solid tumors and other dense tissues) than such conventional 4-chain antibodies and antigen-binding fragments thereof;
- $V_{HH}$ domains and Nanobodies can show so-called cavity-binding properties (inter alia due to their extended CDR3 loop, compared to conventional V domains) and can therefore also access targets and epitopes not accessable to conventional 4-chain antibodies and antigen-binding fragments thereof. For example, it has been shown that $V_{HH}$ domains and Nanobodies can inhibit enzymes (see for example WO 97/49805; Transue et al., Proteins 1998 Sep. 1; 32(4): 515-22; Lauwereys et al., EMBO J. 1998 Jul. 1; 17(13): 3512-20).

For these and other reasons, Nanobodies as well as proteins and/or polypeptides comprising the same generally have improved therapeutic and/or pharmacological properties and/or other advantageous properties (such as, for example, improved ease of preparation and/or reduced costs of goods), compared to conventional antibodies or fragments thereof, compared to constructs that could be based on such conventional antibodies or antibody fragments (such as Fab' fragments, $F(ab')_2$ fragments, ScFv constructs, "diabodies" and other multispecific constructs (see for example the review by Holliger and Hudson, Nat Biotechnol. 2005 September; 23(9):1126-36)), and also compared to the so-called "dAb's" or similar (single) domain antibodies that may be derived from variable domains of conventional antibodies. These improved and advantageous properties will become clear from the further description herein, and for example include, without limitation, one or more of:

- increased affinity and/or avidity for the intended target or antigen, either in a monovalent format, in a multivalent format (for example in a bivalent format) and/or in a multispecific format (for example one of the multispecific formats described hereinbelow);
- better suitability for formatting in a multivalent format (for example in a bivalent format);
- better suitability for formatting in a multispecific format (for example one of the multispecific formats described hereinbelow);
- improved suitability or susceptibility for "humanizing" substitutions (as defined herein);
- less immunogenicity, either in a monovalent format, in a multivalent format (for example in a bivalent format) and/or in a multispecific format (for example one of the multispecific formats described hereinbelow);
- increased stability, either in a monovalent format, in a multivalent format (for example in a bivalent format) and/or in a multispecific format (for example one of the multispecific formats described hereinbelow);
- increased specificity towards the intended target or antigen, either in a monovalent format, in a multivalent format (for example in a bivalent format) and/or in a multispecific format (for example one of the multispecific formats described hereinbelow);
- decreased or where desired increased cross-reactivity with the intended target or antigen from different species;

and/or

- one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described hereinbelow).

Another advantage of Nanobodies compared to for example "dAbs" is that Nanobodies can be generated starting from $V_{HH}$ sequences that are obtained from an animal that has been suitably immunized with the target of interest (i.e. using the techniques mentioned herein and in the prior art cited herein). Generally, this means that Nanobodies will contain CDR's that result from a process of in vivo maturation and/or that Nanobodies can be obtained by screening an immune repertoire (compared to for example CDR's that are generated by screening a naïve library or a random or synthetic library).

Nevertheless, although native $V_{HH}$ sequences will usually have an affinity or specificity for the target as well as other properties that makes them per se suitable for use as single antigen-binding domains, in practice, when designing or generating a Nanobody based on such a $V_{HH}$ sequence, usually also efforts are made to determine whether it is possible to improve one or more desired properties of the $V_{HH}$ sequence.

Even more so, where (single) domain antibodies are derived from non-immune, synthetic and/or random libraries, because such domain antibodies are not the result of an in vivo maturation process, it is usually necessary to improve one or more properties of the domain antibody (often starting with the affinity for the desired target) to provide domain antibodies that are suitable for use in pharmaceutical practice.

For example, and without limitation, some of the properties of amino acid sequences intended for use as a single antigen-binding units that may be the subject of efforts directed to modifying them (and in particular to improving them) include the affinity or specificity for an intended antigen (i.e. affinity maturation), the potency or activity, the selectivity, the solubility, the stability, the tendency to aggregate, the "stickyness", the degree of sequence identity with the closest human germline sequence (i.e. humanization), the presence of epitopes that might be recognized by the human immune system (i.e. deimmunization), the potential immunogenicity (if any), as well as the further properties cited herein; or any desired combination of any of the foregoing and/or any other desired property or properties of the sequence. In doing so, the objective is either to improve one or more of these properties, and/or to establish a proper balance between two or more of these properties. Thus, there is a need in the art for methods that can be used to improve one or more desired properties (or any combination of desired properties) of amino acid sequences that are intended for use as a single antigen-binding domains and/or that can be used to provide such amino acid sequences that have one or more desired or improved properties (or a desired or improved combination of properties). It is an objective of the present invention to provide such methods, and also to provide such improved amino acid sequences (as well as nucleotide sequences encoding the same).

The invention solves this problem by providing a method that can be used to generate a set, collection or library of amino acid sequences (or nucleotide sequences encoding the same) that can be used as a single antigen-binding domains and that differ from each other in the presence of one or more predetermined amino acid residues on one or more predetermined positions in the amino acid sequence (herein also referred to as "specific mutations". The positions in the amino acid sequence where such specific mutations are introduced or positioned using the methods described herein are also referred to as positions that are being "varied").

The invention further solves this problem by providing a set, collection or library of amino acid sequences (or nucleotide sequences encoding the same) that can be generated by this method. This set, collection or library of amino acid sequences (and/or the individual amino acid sequences present therein) can be tested or screened for the presence of one or more desired properties (or any suitable combination of desired properties).

Conveniently, according to a preferred but non-limiting aspect of the invention (as further described herein), such a set, collection or library can be generated in a single step process, comprising PCR assembly of an appropriate series or pool oligonucleotides (optionally followed by suitable expression). Conveniently, as further described herein, this may also provide the set, collection or library in a format that is suited for screening, for example using one of the methods described herein.

Also, according to another preferred but non-limiting aspect of the invention (also as further described herein), such a set, collection or library is generated by taking the amino acid sequence or nucleotide sequence of a known or desired single antigen-binding domain (or a nucleotide sequence encoding the same) as a starting point, such as the sequence of a $V_{HH}$ or a (single) domain antibody. In this way, based on the starting sequence, the invention makes it possible to provide a series of analogs of the starting sequence, that each differ from the starting sequence (and from each other) in the presence of one or more predetermined amino acid residues on one or more predetermined positions in the amino acid sequence (i.e. in one or more "specific mutations"). This set, collection or library of analogs (and/or the individual analogs) can be screened for analogs having one or more desired and/or improved properties (i.e. compared to the starting sequence), and/or the individual analogs can be tested for the influence of one or more specific mutations (as defined herein) on these properties.

For example, as further described herein, these specific mutations can be one or more humanizing substitutions or camelizing substitutions, one or more substitutions in the complementarity determining region (for example made for the purposes of affinity maturation), one or more substitutions that are meant to remove certain specific epitopes (for example made for the purposes of deimmunization) and/or one or more specific mutations that are meant to introduce or to remove other amino acid residues with a specific structural and/or biological function.

Thus, in a first aspect, the invention relates to a method for providing a set, collection or library of nucleotide sequences or nucleic acids that encode amino acid sequences that can be used as (and/or are intended for use as) single antigen-binding domains, which method at least comprises the steps of:

i) providing a pool of oligonucleotides that comprises (i) a series of at least two oligonucleotides that can be assembled, by means of PCR assembly, into a nucleotide sequence or nucleic acid that encodes an amino acid sequence that can be used as (and/or is intended for use as) a single antigen-binding domain, and in addition comprises (ii) at least one variant of at least one of the at least two oligonucleotides that form part of the series, in which said at least one variant differs from said oligonucleotide (and also from the other variants of said oligonucleotide present in the pool, if any) in that it encodes an amino acid sequence that differs in the presence of one or more predetermined amino acid residues on one or more predetermined positions (i.e. in the presence of one or more "specific mutations");
and
ii) subjecting the pool of oligonucleotides to PCR assembly.

The oligonucleotides and variants thereof that are provided and used in step a) (i.e. as part of the pool of oligonucleotides) will also generally and collectively be referred to herein as the "oligonucleotides used in step a)".

Generally, in the methods described herein, the PCR assembly of step b) is performed in such a way that the oligonucleotides used in step a) are assembled into a set, collection or library of (larger or full-length) nucleotide sequences or nucleic acids that encode amino acid sequences that can be used as (and/or are intended for use as) single antigen-binding domains. As will be clear to the skilled person, exactly which (larger or full-sized) nucleotide sequences or nucleic acids will be obtained as a result of the PCR assembly in step b) will mainly depend on the oligonucleotides used in step a). Thus, by suitably choosing the oligonucleotides used in step a)—as further described herein—the invention can be used to provide a set, collection or library of desired or predetermined (larger or full-sized) nucleotide sequences or nucleic acids. Also, most preferably, the oligonucleotides used in step a) are chosen such that the nucleotide sequences or nucleic acids obtained as a result of the PCR assembly step b) encode amino acid sequences that differ from each other in the presence of one or more (predetermined) specific mutations (as defined herein).

For example, the methods described herein may be used to provide a set, collection or library of synthetic or semi-synthetic sequences or variants. These may for example be a set of "randomized" sequences, i.e. sequences that have one or more random amino acid residues at one or more (predetermined) amino acid positions. Such a set, collection or library of randomized sequences may for example be provided by using primers that contain so-called degenerate codons at the one or more amino acid positions that are to be randomized (for example using NNK or NNS codons, where K=G or T and S=C or G. These codons may encode the complete set of standard amino acids).

Thus, in one aspect of the invention, the at least one of the oligonucleotides used in step a) contains at least one degenerate codon at at least one predetermined amino acid position. When, as indicated below, the amino acid sequences that are assembled using the method of the invention comprise four framework sequences and three complementarity determining sequences, the one or more degenerate codons may be in one or more of the framework sequences; may be in one or more of the complementarity determining sequences; and/or may be in one or more of the framework sequences and/or in one or more of the complementarity determining sequences.

For example, starting from a combination of known framework sequences (e.g. the framework sequences of a Nanobody as described herein), the methods of the invention may be used to provide a (synthetic or semi-synthetic) set, collection or library of amino acid sequences that comprise four framework sequences and three complementarity determining sequences, with (fully or partially) random CDR's, which may for example be screened for amino acid sequences that have affinity for a desired antigen.

Also, starting from an amino acid sequence with known affinity or specificity for a desired antigen (for example a $V_{HH}$ sequence or other Nanobody), the methods of the invention may be used to provide a (synthetic or semi-synthetic) set, collection or library of variants of this starting sequence with one or more random mutations in one or more of the CDR's or may be particular mutation or mutations (e.g. mutation of each CDR residue by amino acids with similar side-chain chemistries or e.g. mutation of each CDR residue by a set of amino acids which naturally occur on the given position). Such a set, collection or library may for example be screened for amino acid sequences that have improved affinity or specificity for the desired antigen (i.e. as part of techniques for affinity maturation of the starting sequence). Other applications and uses of methods of the invention in which one or more random mutations are introduced will be clear to the skilled person based on the disclosure herein.

In particular, as further described herein, the invention relates to a method as described above in which the set, collection or library of nucleotide sequences or nucleic acids provided is a set, collection or library of nucleotide sequences or nucleic acids that each encode an amino acid sequence that is an analog of a predetermined amino acid sequence (and in which the set, collection or library may optionally also contain a nucleotide sequence or nucleic acid that encodes the predetermined amino acid sequence). In this method, the predetermined amino acid sequence (and as a result, usually also the analogs thereof obtained as a result of the PCR assembly) is again most preferably an amino acid sequence that can be used as (and/or that is intended for use as) a single antigen-binding domain. Thus, by suitably choosing the oligonucleotides used in step a)—as further described herein—the invention can be used to provide such a set, collection or library of nucleotide sequences or nucleic acids that each encode an analog of the predetermined amino acid sequence, in which the analogs encoded by the set, collection or library differ from each other (and from the predetermined amino acid sequence) in the presence of one or more (predetermined) specific mutations (as defined herein). For example and without limitation, and as further described herein, the invention may be used to provide a set, collection or library of (nucleic acids or nucleotide sequences encoding) amino acid sequences (i.e. Nanobodies) that are variants of a wildtype $V_{HH}$ sequence; for example (and without limitation), humanized variants (e.g. for humanization) or variants with one or more predetermined (e.g. amino acid substitutions with similar side chain or amino acid which naturally occur on the given position) or random mutations in one or more of the CDR's (e.g. for affinity maturation).

Accordingly, in another aspect, the invention relates to method for providing a set, collection or library of nucleotide sequences or nucleic acids that encode amino acid sequences that are analogs of a predetermined amino acid sequence, in which at least the predetermined amino acid sequence (and preferably also the analogs) can be used as (and/or is intended for use as) a single antigen-binding domain, which method at least comprises the steps a) and b) above, and which method optionally also comprises one or more of the further steps mentioned herein. In this method, the set, collection or library of nucleotide sequences or nucleic acids that is obtained after the PCR assembly may optionally also contain a nucleotide sequence or nucleic acid that encodes the predetermined amino acid sequence.

In the methods described herein, the oligonucleotides used in step a) are preferably such that the nucleotide sequences obtained as a result of the PCR assembly in step b) encode amino acid sequences that contain an immunoglobulin fold or that are capable of forming (i.e. by folding under appropriate circumstances) an immunoglobulin fold.

More in particular, the oligonucleotides used in step a) may be such that the nucleotide sequences obtained as a result of the PCR assembly in step b) encode amino acid sequences that each comprise or essentially consist of 4 framework regions and 3 complementarity determining regions. In this aspect of the invention, the oligonucleotides used in step a) may be such that the nucleotide sequences obtained as a result of the PCR assembly in step b) encode amino acid sequences that differ from each other (and from the predetermined sequence, if any) in the presence of one or more (predetermined) specific mutations in (any of) the framework regions, in the presence of one or more (predetermined) specific mutations in (any of) the complementarity determining regions; and/or in the presence of one or more (predetermined) specific mutations in (any of) the framework regions as well as one or more (predetermined) specific mutations in (any of) the complementarity determining regions.

More in particular, the rules (partly or fully followed) for substitutions of the predetermined specific mutations as referred to above may be as follows (i.e. substitution with amino acids with similar side chain chemistries):

K is substituted by R;
R is substituted by K;
A is substituted by S or T;
S is substituted by A or T;
T is substituted by A or S;
I is substituted by L or V;
L is substituted by I or V;
V is substituted by I or L;
F is substituted by Y;
Y is substituted by F;
N is substituted by D;
D is substituted by N;
Q is substituted by E;
E is substituted by Q;
G is substituted by A;
M is substituted by L;
H, C, W and P are kept constant.

Furthermore, the rules (partly or fully followed) for substitutions of the predetermined specific mutations as referred to above may be alternatively as follows for substitutions at positions 27 to 35 and positions 50 to 58 (using Kabat numbering system), wherein for positions 27 to 35:

Original amino acid residue in position 27 (Kabat numbering used) is substituted by F; G; R; S; 2 out of F, G, R, S; 3 out of F, G, R, S; or all of them, preferably all of them; Original amino acid residue in position 28 (Kabat numbering used) is substituted by A; I; S; T; 2 out of A, I, S, T; 3 out of A, I, S, T; or all of them, preferably all of them;

Original amino acid residue in position 29 (Kabat numbering used) is substituted by F; G; L; S; 2 out of F, G, L, S; 3 out of F, G, L, S; or all of them, preferably all of them;

Original amino acid residue in position 30 (Kabat numbering used) is substituted by D; G; S; T; 2 out of D, G, S, T; 3 out of D, G, S, T; or all of them, preferably all of them;

Original amino acid residue in position 31 (Kabat numbering used) is substituted by D; I; N; S; T; 2 out of D, I, N, S, T; 3 out of D, I, N, S, T; or all of them, preferably all of them;

Original amino acid residue in position 32 (Kabat numbering used) is substituted by D; N; Y; 2 out of D, n, Y; or all of them, preferably all of them;

Original amino acid residue in position 33 (Kabat numbering used) is substituted by A; G; T; V; 2 out of A, G, T, V; 3 out of A, G, T, V; or all of them, preferably all of them;

Original amino acid residue in position 34 (Kabat numbering used) is substituted by I; M; or all of them, preferably all of them;

Original amino acid residue in position 35 (Kabat numbering used) is substituted by A; G; S; 2 out of A, G, S; or all of them, preferably all of them;

and positions 50 to 58 if original amino acid sequence has an amino acid sequence in position 52a (Kabat numbering used), Original amino acid residue in position 50 (Kabat numbering used) is substituted by A; C; G; S; T; 2 out of A, C, G, S, T; 3 out of A, C, G, S, T; 4 out of A, C, G, S, T; or all of them, preferably all of them;

Original amino acid residue in position 51 (Kabat numbering used) is substituted by I;

Original amino acid residue in position 52 (Kabat numbering used) is substituted by N; R; S; T; 2 out of N, R, S, T; 3 out of N, R, S, T; or all of them, preferably all of them;

Original amino acid residue in position 52a (Kabat numbering used) is substituted by R; S; T; W; 2 out of R, S, T, W; 3 out of R, S, T, W; or all of them, preferably all of them;

Original amino acid residue in position 53 (Kabat numbering used) is substituted by D; G; N; S; T; 2 out of D, G, N, S, T; 3 out of D, G, N, S, T; 4 out of D, G, N, S. T; or all of them, preferably all of them;

Original amino acid residue in position 54 (Kabat numbering used) is substituted by D; G; or all of them, preferably all of them;

Original amino acid residue in position 55 (Kabat numbering used) is substituted by D; G; S; 2 out of D, G, S; or all of them, preferably all of them;

Original amino acid residue in position 56 (Kabat numbering used) is substituted by I; N; R; S; T; 2 out of I, N, R, S, T; 3 out of I, N, R, S, T; 4 out of I, N, R, S, T; or all of them, preferably all of them;

Original amino acid residue in position 57 (Kabat numbering used) is substituted by T;

Original amino acid residue in position 58 (Kabat numbering used) is substituted by D; H; N; S; Y; 2 out of D, H, N, S, Y; 3 out of D, H, N, S, Y; 4 out of D, H, N, S, Y; or all of them, preferably all of them;

and wherein for positions 50 to 58 if original amino acid sequence has not an amino acid sequence in position 52a (Kabat numbering used), Original amino acid residue in position 50 (Kabat numbering used) is substituted by A; G; R; S; T; 2 out of A, G, R, S, T; 3 out of A, G, R, S, T; 4 out of A, G, R, S, T; or all of them, preferably all of them;

Original amino acid residue in position 51 (Kabat numbering used) is substituted by I;

Original amino acid residue in position 52 (Kabat numbering used) is substituted by N; S; T; 2 out of N, S, T; or all of them, preferably all of them;

Original amino acid residue in position 53 (Kabat numbering used) is substituted by N; R; S; T; Y; 2 out of N, R, S, T, Y; 3 out of N, R, S, T, Y; 4 out of N, R, S, T. Y; or all of them, preferably all of them;

Original amino acid residue in position 54 (Kabat numbering used) is substituted by D; G: R; S; 2 out of D, G, R, S; 3 out of D, G, R, S; or all of them, preferably all of them;

Original amino acid residue in position 55 (Kabat numbering used) is substituted by G;

Original amino acid residue in position 56 (Kabat numbering used) is substituted by G; N; R; S; T; 2 out of D, N, R, S, T; 3 out of D, N, R, S, T; 4 out of D, N, R, S, T; or all of them, preferably all of them;

Original amino acid residue in position 57 (Kabat numbering used) is substituted by T;

Original amino acid residue in position 58 (Kabat numbering used) is substituted by D; N; T; Y; 2 out of D, N, T, Y; 3 out of D, N, T, Y; or all of them, preferably all of them.

According to one specific, but non-limiting aspect, the oligonucleotides used in step a) are such that the nucleotide sequences obtained as a result of the PCR assembly in step b) encode amino acid sequences that comprise or essentially consist of an immunoglobulin variable domain or a suitable fragment thereof, and in particular encode amino acid sequences that comprise or essentially consist of a domain antibody or of an amino acid sequence that is suitable for use as a domain antibody, of a single domain antibody or of an amino acid sequence that is suitable for use as a single domain antibody, of a "dAb" or of an amino acid sequence that is suitable for use as a dAb, or (preferably) of a Nanobody™ (or any suitable fragment of any of the foregoing, as further defined herein).

The invention also relates to a set, collection or library of nucleotide sequences or nucleic acids that can be obtained using the above method.

The invention also relates to a method for generating a set, collection or library of amino acid sequences that can be used as (and/or are intended for use as) single antigen-binding domains, which method comprises subjecting the above set, collection or library of nucleotide sequences or nucleic acids (one or more nucleotide sequences or nucleic acids from said set, collection or library) to translation and/or expression (i.e. in a manner known per se); and to the set, collection or library of amino acid sequences that can be obtained (or has been obtained) using this method.

The invention further relates to the individual nucleotide sequences or nucleic acids that can be obtained (or have been obtained) via the above method and/or from the above set, collection or library of nucleotide sequences or nucleic acids, as well as to the individual amino acid sequences that can be obtained (or have been obtained) by expressing such a nucleotide sequence or nucleic acid.

The invention further relates to a method as described above, which further comprises the step of:

iii) screening the set, collection or library of nucleotide sequences or nucleic acids obtained through steps a) and b) for nucleotide sequences or nucleic acids that encode amino acid sequences that have one or more desired properties (or combination of desired properties), and optionally isolating one or more nucleotide sequences or nucleic acids that encode amino acid sequences that have said one or more desired properties.

Again, in this method, the set, collection or library of nucleotide sequences or nucleic acids that is screened in step c) preferably encodes a set, collection or library of amino acid sequences that are analogs of a predetermined amino acid sequence (in which said set, collection or library may optionally also include a nucleotide sequence or nucleic acid that encodes the predetermined amino acid sequence), and in particular of analogs that differ from each other (and from the predetermined sequence) in the presence of one or more (predetermined) specific mutations. In particular, in such a method, the set collection or library may be screened for nucleotide sequences or nucleic acids that encode analogs with one or more improved (desired) properties compared to the predetermined amino acid sequence.

The invention also relates to a method as described above, which further comprises the step of:

c) testing one or more nucleotide sequences or nucleic acids from the set, collection or library of nucleotide sequences or nucleic acids obtained through steps a) and b) as to whether they encode an amino acid sequence that has one or more desired properties (or combination of desired properties).

Again, in this method, the nucleotide sequences or nucleic acids that are tested in step c) preferably encode amino acid sequences that are analogs of a predetermined amino acid sequence (in which optionally, a nucleotide sequence or nucleic acid that encodes the predetermined amino acid sequence may also be tested), and in particular of analogs that differ from each other (and from the predetermined sequence) in the presence of one or more (predetermined) specific mutations. In particular, in such a method, the one or more nucleotide sequences or nucleic acids may be tested in order to identify and/or provide nucleotide sequences or nucleic acids that encode analogs that have one or more improved properties compared to the predetermined amino acid sequence.

In each of the steps c) mentioned above, the screening and/or testing of the set, collection or library of nucleotide sequences or of the individual nucleotide sequences can be performed in any suitable manner known per se, also depending upon the property or properties to be screened or tested. Generally, such methods will involve at least a step of suitably expressing or translating the nucleotide sequence(s) into the corresponding amino acid sequence(s), and then testing or screening said amino acid sequences for said one or more properties.

For example, for screening a set, collection or library of nucleotide sequences, the set, collection or library of nucleotide sequences may be displayed on a phage, phagemid, ribosome or suitable micro-organism (such as yeast), so as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

Individual nucleotide sequences or a limited set of nucleotide sequences may also be individually expressed (e.g. in a suitable host or host organism) and the individual amino acid sequences may then be tested for the one or more properties, using any suitable method, technique or assay (e.g. an in vitro, cellular or in vivo assay or model).

The invention also relates to a method for providing one or more nucleotide sequences or nucleic acids that encode amino acid sequences that can be used as (and/or are intended for use as) single antigen-binding domains and that have one or more desired properties (or a combination of desired properties), which method comprises screening (i.e. in a manner known per se) the above set, collection or library of nucleotide sequences or nucleic acids for nucleotide sequences or nucleic acids that encode amino acid sequences that have said one or more desired properties (or combination or desired properties). Optionally, this method further comprises isolating one or more nucleotide sequences or nucleic acids that encode amino acid sequences with said one or more desired properties.

The invention further relates to a method for providing one or more nucleotide sequences or nucleic acids that encode amino acid sequences that can be used as (and/or are intended for use as) single antigen-binding domains and that have one or more desired properties (or a combination of desired properties), which method comprises testing (i.e. in a manner known per se) whether one or more of the nucleotide sequences or nucleic acids from the above set, collection or library of nucleotide sequences or nucleic acids encode an amino acid sequence that has said one or more desired properties.

The invention also relates to the individual nucleotide sequences or nucleic acids that can be obtained (or have been obtained) using these methods, as well as to the individual amino acid sequences that can be obtained (or have been obtained) by expressing such a nucleotide sequence or nucleic acid.

Again, as mentioned above, the screening and/or testing of the set, collection or library of nucleotide sequences or of the individual nucleotide sequences can be performed in any suitable manner known per se.

The invention further relates to a method for providing a set, collection or library of amino acid sequences that can be used as (and/or are intended for use as) single antigen-binding domains, which method at least comprises the steps of:

a) providing a pool of oligonucleotides that comprises (i) a series of at least two oligonucleotides that can be assembled, by means of PCR assembly, into a nucleotide sequence that encodes an amino acid sequence that can be used as (and/or is intended for use as) a single antigen-binding domain, and in addition comprises (ii) at least one variant of at least one of the at least two oligonucleotides that form part of the series, in which said at least one variant differs from said oligonucleotide (and also from the other variants of said oligonucleotide present in the pool, if any) in that it encodes an amino acid sequence that differs in the presence of one or more specific mutations;
b) subjecting the pool of oligonucleotides to PCR assembly; and
c) subjecting the assembled oligonucleotide sequences thus obtained to translation and/or expression in a suitable manner known per se.

In the above method, steps a) and b) are generally as described herein, and step c) can be performed in any suitable manner known per se for expressing the set, collection or library of assembled nucleotide sequences obtained after step b) (or for expressing any one or more, and in particular any two or more, of the nucleotide sequences from said set, collection or library). Reference is again made to the further disclosure herein.

As with the other methods described herein, the set, collection or library of amino acid sequences provided after step c) is preferably a set, collection or library of analogs of a predetermined amino acid sequence (which set, collection or library may optionally also contain the predetermined amino acid sequence), and in particular of analogs that differ from each other (and from the predetermined sequence) in the presence of one or more (predetermined) specific mutations. This can again be achieved by suitably choosing the oligonucleotides used in step a). Also, again, the predetermined amino acid sequence and the analogs thereof are preferably amino acid sequences can be used as (and/or that are intended for use as) a single antigen-binding domain.

Accordingly, in another aspect, the invention relates to method for providing a set, collection or library of encode amino acid sequences that are analogs of a predetermined amino acid sequence, in which at least the predetermined amino acid sequence (and preferably also the analogs) can be used as (and/or is intended for use as) a single antigen-binding domain, which method at least comprises the above steps a) to c), and optionally also comprises one or more of the further steps mentioned herein. In this method, a set, collection or library of amino acid sequences may optionally also contain the predetermined amino acid sequence.

Also, again, in the above method, the oligonucleotides used in step a) are preferably chosen in such a way that the amino acid sequences provided after step c) contain an immunoglobulin fold or are capable of forming (i.e. by folding under appropriate circumstances) an immunoglobulin fold.

More in particular, the oligonucleotides used in step a) may be chosen in such a way that the amino acid sequences provided after step c) comprise or essentially consist of 4 framework regions and 3 complementarity determining regions. In this aspect of the invention, the oligonucleotides used in step a) may again be chosen in such a way that the amino acid sequences obtained after step a) differ from each other (and/or from the predetermined sequence, if used) in the presence of one or more (predetermined) specific mutations in (any of) the framework regions, in the presence of one or more (predetermined)specific mutations in (any of) the complementarity determining regions; and/or in the presence of both one or more (predetermined) specific mutations in (any of) the framework regions as well as one or more (predetermined) specific mutations in (any of) the complementarity determining regions.

Also, again, according to one specific, but non-limiting aspect, the oligonucleotides used in step a) are such that the amino acid sequences obtained after step c) are amino acid sequences that comprise or essentially consist of an immunoglobulin variable domain sequence or a suitable fragment thereof, and in particular amino acid sequences that comprise or essentially consist of a domain antibody or of an amino acid sequence that is suitable for use as a domain antibody, of a single domain antibody or of an amino acid sequence that is suitable for use as a single domain antibody, of a "dAb" or of an amino acid sequence that is suitable for use as a dAb, or (preferably) of a Nanobody™ (or any suitable fragment of any of the foregoing, as further defined herein).

The invention also relates to a set, collection or library of amino acid sequences that can be obtained (or has been obtained) using the above method.

The invention further relates to the individual amino acid sequences that can be obtained (or have been obtained) via the above method and/or from the above set, collection or library of amino acid sequences.

The invention further relates to a method as described above, which further comprises the step of:
iv) screening the set, collection or library of amino acid sequences obtained through steps a) to c) for amino acid sequences that have one or more desired properties (or combination of desired properties), and optionally isolating one or more amino acid sequences that have said one or more desired properties.

Again, in this method, the set, collection or library of amino acid sequences that is screened in step d) preferably is a set, collection or library of amino acid sequences that are analogs of a predetermined amino acid sequence (in which said set, collection or library may optionally also include the predetermined amino acid sequence). In particular, in such a method, the set, collection or library may be screened for analogs with one or more improved (desired) properties compared to the predetermined amino acid sequence.

The invention also relates to a method as described above, which further comprises the step of:
d) testing one or more amino acid sequences from the set, collection or library of amino acid sequences obtained through steps a) to c) as to whether they have one or more desired properties (or combination of desired properties).

Again, in this method, the amino acid sequences that are tested in step d) are preferably analogs of a predetermined amino acid sequence (in which optionally, the predetermined amino acid sequence may also be tested). In particular, in such a method, the one or more amino acid sequences may be tested in order to identify and/or provide analogs that have one or more improved properties compared to the predetermined amino acid sequence.

In the steps c) mentioned above, the screening and/or testing of the set, collection or library of amino acid sequences or of the individual amino acid sequences can be performed in any suitable manner known per se, also depending upon the property or properties to be screened or tested. This will be clear to the skilled person based on the further disclosure herein.

For example, for screening the set, collection or library of amino acid sequences, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

Individual amino acid sequences may also be tested for the one or more properties, using any suitable method, technique or assay (e.g. an in vitro, cellular or in vivo assay or model).

The invention also relates to a method for providing one or more amino acid sequences that can be used as (and/or are intended for use as) single antigen-binding domains and that have one or more desired properties (or a combination of desired properties), which method comprises screening (i.e. in a manner known per se) the above set, collection or library of amino acid sequences for amino acid sequences that have said one or more desired properties (or combination or desired properties). Optionally, this method further comprises isolating one or more amino acid sequences that have said one or more desired properties.

The invention further relates to a method for providing one or more amino acid sequences that can be used as (and/or are intended for use as) single antigen-binding domains and that have one or more desired properties (or a combination of desired properties), which method comprises testing (i.e. in a manner known per se) whether one or more of the amino acid sequences from the above set, collection or library of amino acid sequences have said one or more desired properties.

The invention also relates to the amino acid sequences that can be obtained (or have been obtained) using the above methods.

In the above methods, the screening and/or testing of the set, collection or library of amino acid sequences sequences or of the individual amino acid sequences sequences can again be performed in any suitable manner known per se.

In the methods described herein, the set, collection or library of sequences (i.e. the set, collection or library of nucleotide sequences or nucleic acids or the set, collection or library of amino acid sequences) and/or the individual sequences (i.e. the individual nucleotide or the individual amino acid sequences screened or tested) may be screened or tested, respectively, for any suitable or desired property or combination of properties.

For example, the amino acid sequences may be screened or tested for (and/or the nucleotide sequences or nucleic acids may be screened or tested for nucleotide sequences or nucleic acids that encode amino acid sequences with) one or more of the following (desired) properties: the affinity or specificity for an intended antigen (i.e. affinity maturation), the potency or activity (i.e. in a suitable in vitro, cellular or in vivo assay or model), the selectivity, the solubility, the stability (for example, thermal stability; stability under storage; stability at different pH values or temperatures; stability against proteolytic cleavage; stability in different biological fluids or conditions, such as in serum or the conditions prevalent in the stomach, intestines or any other part of the gastrointestingal tract; stability of pharmaceutical preparations comprising the amino acid sequence; resistance to (auto-)oxidation), the tendency to aggregate, the "stickyness", the folding of the amino acid sequence, the degree of sequence identity with the closest human germline sequence (i.e. humanization), the presence of epitopes that might be recognized by the human immune system (i.e. deimmunization), the potential immunogenicity (if any), the presence of one or more amino acid residues or of a stretch of amino acid residues that allow(s) the amino acid sequence to undergo one or more interactions other than the interaction with the intended antigen (such as introduction of a second binding site for interaction with another antigen), the expression levels in a desired host or host cell, the half-life, the presence or absence of sites or amino acid residues that can be modified (e.g. pegylated, glycolysated and/or that can be modified as part of post-translational modification), the presence or absence of sites or amino acid residues that are subject to oxidation (e.g. during production/expression or under storage), the presence or absence of cysteine residues that can form disulphide bridges, etc., the ability to cross biological membranes or barriers such as cell membranes, the intestinal wall or the blood brain barrier, or any desired combination of any of the foregoing and/or any other desired property or properties of the sequence. In one specific, but non-limiting aspect, the amino acid sequences may be screened or tested for (and/or the nucleotide sequences or nucleic acids may be screened or tested for nucleotide sequences or nucleic acids that encode amino acid sequences with) one or more of the following (desired) properties: the affinity or specificity for an intended antigen, the potency or activity (i.e. in a suitable cellular or in vivo assay) and/or the selectivity for the intended antigen, and in particular (at least) for the affinity or specificity for an intended antigen of the amino acid sequence(s) that are screened or tested. In particular, as further described herein, this aspect of the invention may be used in methods directed to affinity maturation of the starting sequence. According to this specific aspect, the set, collection or library of amino acid sequences (or of nucleotide sequences or nucleic acids encoding the same) that is screened is preferably a set, collection or library of amino acid sequences (or of nucleotide sequences or nucleic acids encoding the same) that each comprise or essentially consist of 4 framework regions and 3 complementarity determining regions and that differ from each other (and optionally from the predetermined sequence, if used) in the presence of one or more specific mutations in the complementarity determining regions. Similarly, when one or more individual amino acid sequences (or nucleotide sequences or nucleic acids encoding the same) are tested, they are preferably amino acid sequences (or nucleotide sequences or nucleic acids encoding the same) that each comprise or essentially consist of 4 framework regions and 3 complementarity determining regions and that differ from each other (and optionally from the predetermined sequence, if used) in the presence of one or more specific mutations in the complementarity determining regions.

In another specific, but non-limiting aspect, the amino acid sequences may be screened or tested for (and/or the nucleotide sequences or nucleic acids may be screened or tested for nucleotide sequences or nucleic acids that encode amino acid sequences with) one or more of the following (desired) properties: the stability, the tendency to aggregate, the "stickyness", the folding of the amino acid sequence and/or the expression levels in a desired host or host cell, and in particular (at least) stability, the tendency to aggregate and/or the "stickyness" of the amino acid sequence(s) that are screened or tested. For example, as further described herein, this aspect of the invention may be used to generate a set, collection or library of humanized analogs (or alternatively camelized analogs) of the starting sequence and/or to determine how humanization of the sequence may influence these properties (or alternatively, how camelization of the sequence may influence these properties). According to this specific aspect, the set, collection or library of amino acid sequences (or of nucleotide sequences or nucleic acids encoding the same) that is screened is preferably a set, collection or library of amino acid sequences (or of nucleotide sequences or nucleic acids encoding the same) that each comprise or essentially consist of 4 framework regions and 3 complementarity determining regions and that differ from each other (and optionally from the predetermined sequence, if used) in the presence of one or more specific mutations in the framework regions. Similarly, when one or more individual amino acid sequences (or of nucleotide sequences or nucleic acids encoding the same) are tested, they are preferably amino acid sequences (or nucleotide sequences or nucleic acids encoding the same) that each comprise or essentially consist of 4 framework regions and 3 complementarity determining regions and that differ from each other (and optionally from the predetermined sequence, if used) in the presence of one or more specific mutations in the framework regions.

In yet another specific, but non-limiting aspect, the amino acid sequences may be screened or tested for the influence of changing (and in particular of improving or increasing) the degree of sequence identity with the closest human germline sequence, in order to see how changing the degree of sequence identity may influence the other properties of the sequence (such as the further properties mentioned herein). In particular, as further described herein, this aspect of the invention may be used to generate a set, collection or library of humanized analogs of a starting sequence and/or to determine how (further) humanization of the sequence may influence the properties of the sequence (or alternatively, how camelization of the sequence may influence these properties).

According to this specific aspect, the set, collection or library of amino acid sequences (or of nucleotide sequences or nucleic acids encoding the same) that is screened is preferably a set, collection or library of amino acid sequences (or of nucleotide sequences or nucleic acids encoding the same) that each comprise or essentially consist of 4 framework regions and 3 complementarity determining regions and that differ from each other (and optionally from the predetermined sequence, if used) in the presence of one or more specific mutations in the framework regions. Similarly, when one or more individual amino acid sequences (or of nucleotide sequences or nucleic acids encoding the same) are tested, they are preferably amino acid sequences (or nucleotide sequences or nucleic acids encoding the same) that each comprise or essentially consist of 4 framework regions and 3 complementarity determining regions and that differ from each other (and optionally from the predetermined sequence, if used) in the presence of one or more specific mutations in the framework regions.

In yet another specific, but non-limiting aspect, the amino acid sequences may be screened or tested for the influence of modifying (and in particular of removing) one or more epitopes that might be recognized by the human immune system in order to see how mutating (or even fully or partially removing) such epitopes may influence the (potential) immunogenicity (if any) and/or any other properties of the sequence (such as the further properties mentioned herein). For example, as further described herein, this aspect of the invention may be used to generate a set, collection or library of analogs of the starting sequence without said epitopes and/or to determine how removing one or more of these epitopes (i.e. deimmunisation) may influence these properties. According to this specific aspect, the set, collection or library of amino acid sequences (or of nucleotide sequences or nucleic acids encoding the same) that is screened is preferably a set, collection or library of amino acid sequences (or of nucleotide sequences or nucleic acids encoding the same) that differ from each other in the presence of one or more specific mutations in the amino acid residues that correspond to epitopes that might be recognized by the human immune system.

It should also be noted that the invention can also be used to provide a set, collection or library of nucleic acids or nucleotide sequences that can be screened or tested for one or more nucleic acids or nucleotide sequences with one or more favourable properties, such as stability (e.g. stability of the RNA that can be obtained by transcription of a DNA that is obtained by the methods described herein) or expression levels in a desired host or host cell.

For example, and without limitation, by using the degeneracy of the genetic code, the methods of the invention may be used to provide a set, collection or library of nucleic acids or nucleotide sequences that are analogs of a starting nucleotide sequence (and that preferably encode the same amino acid sequence as the starting sequence), but that differ from the starting sequence in one or more codons. This set, collection or library (or individual nucleic acids from this set, collection or library) may then for example be screened or tested for nucleic acids that provide improved/increased levels of expression of the desired amino acid sequence in a desired host organism. This aspect of the invention may for example be used to provide nucleic acids that encode a desired amino acid sequence (i.e. the same amino acid sequence as encoded by the starting sequence), but that contains one or more codons that are optimized for expression in the desired host or host organism. Other applications and uses of this specific aspect of the invention will be clear to the skilled person based on the disclosure herein.

The invention again also relates to the nucleotide sequences and/or amino acid sequences that can be obtained (or have been obtained) by the methods described herein.

The invention further relates to nucleotide sequences and/or amino acid sequences that have the same nucleotide sequence or amino acid sequence, respectively, as a nucleotide sequence and/or amino acid sequence that has been obtained by the methods described herein.

In another aspect, the invention relates to a protein or polypeptide that comprises or essentially consists of at least one amino acid sequence that can be obtained by (or that has been obtained by) one of the methods described herein. Such proteins or polypeptides can be as further described herein, and can for example be a monovalent, multivalent or multispecific construct, as further described herein.

In yet another aspect, the invention relates to a nucleotide sequence or nucleic acid that comprises or essentially consists of at least nucleotide sequence or nucleic acid that can be obtained by (or that has been obtained by) one of the methods described herein. Such a nucleotide sequence or nucleic acid can be as further described herein, and can for example be in the form of a genetic construct.

Other aspects, embodiments, applications, uses and advantages of the invention described herein will become clear from the further description herein.

FURTHER DESCRIPTION OF THE INVENTION

In the present description, examples and claims:

a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989), F. Ausubel et al, eds., "Current protocols in molecular biology". Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10$^{th}$ Ed. Blackwell Publishing, U K (2001); and Janeway et al., "Immunobiology" (6th Ed.), Garland Science Publishing/Churchill Livingstone, N.Y. (2005), as well as to the general background art cited herein;

b) Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation;

c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

d) Amino acid residues will be indicated according to the standard three-letter or one-letter amino acid code, as mentioned in Table A-2;

TABLE A-2 one-letter and three-letter amino acid code

| | | | |
|---|---|---|---|
| Nonpolar, uncharged (at pH 6.0-7.0) [3] | Alanine | Ala | A |
| | Valine | Val | V |
| | Leucine | Leu | L |
| | Isoleucine | Ile | I |
| | Phenylalanine | Phe | F |
| | Methionine [1] | Met | M |
| | Tryptophan | Trp | W |
| | Proline | Pro | P |
| Polar, uncharged (at pH 6.0-7.0) | Glycine [2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged (at pH 6.0-7.0) | Lysine | Lys | K |
| | Arginine | Arg | R |
| | Histidine [4] | His | H |
| | Aspartate | Asp | D |
| | Glutamate | Glu | E |

Notes:
[1] Sometimes also considered to be a polar uncharged amino acid.
[2] Sometimes also considered to be a nonpolar uncharged amino acid.
[3] As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4] As is known in the art, the charge of a His residue is greatly dependant upon even small shifts in pH, but a His residu can generally be considered essentially uncharged at a pH of about 6.5.

e) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).

Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999. EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;

f) For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185. WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His. Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gin or into His; Asp into Glu; Cys into Ser; Gin into Asn; Glu into Asp; Gly into Ala or into Pro; His into Asn or into Gin; Ile into Leu or into Val; Leu into Ile or into Val; Lys into Arg, into Gin or into Glu; Met into Leu, into Tyr or into Ile; Phe into Met, into Leu or into Tyr, Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman. Biochemistry 13: 211, 1974 and Adv. Enzymol., 47: 45-149, 1978, and on the analysis of hydrophobicity patterns in proteins developed by Eisenberg et al., Proc. Nad. Acad Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure. Vol. 7, 4, 361 (1999). Further information about some of the amino acid residues that in conventional $V_{HH}$ domains form the $V_H/V_L$ interface and potential camelizing substitutions on these positions can be found in the prior art cited above.

g) Amino acid sequences and nucleic acids are said to be "exactly the same" if they have 100% sequence identity (as defined herein) over their entire length;

h) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

i) When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the firstmentioned nucleotide sequence or amino acid sequence, respectively, but more usually this generally means that the firstmentioned nucleotide sequence or amino acid sequence comprises within its sequence a stretch of nucleotides or amino acid residues, respectively, that has the same nucleotide sequence or amino acid sequence, respectively, as the latter sequence, irrespective of how the firstmentioned sequence has actually been generated or obtained (which may for example be by any suitable method described herein). By means of a non-limiting example, when a Nanobody of the invention is said to comprise a CDR sequence, this may mean that said CDR sequence has been incorporated into the Nanobody of the invention, but more usually this generally means that the Nanobody of the invention contains within its sequence a stretch of amino acid residues with the same amino acid sequence as said CDR sequence, irrespective of how said Nanobody of the invention has been generated or obtained. It should also be noted that when the latter amino acid sequence has a specific biological or structural function, it preferably has essentially the same, a similar or an equivalent biological or structural function in the firstmentioned amino acid sequence (in other words, the firstmentioned amino acid sequence is preferably such that the latter sequence is capable of performing essentially the same, a similar or an equivalent biological or structural function). For example, when a Nanobody of the invention is said to comprise a CDR sequence or framework sequence, respectively, the CDR sequence and framework are preferably capable, in said Nanobody, of functioning as a CDR sequence or framework sequence, respectively. Also, when a nucleotide sequence is said to comprise another nucleotide sequence, the firstmentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the firstmentioned, larger nucleotide sequence).

j) A nucleic acid or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid sequence is considered "essentially isolated" when it has been purified at least 2-fold, in particular at least 10-fold, more in particular at least 100-fold, and up to 1000-fold or more. A nucleic acid or amino acid sequence that is "in essentially isolated form" is preferably essentially homogeneous, as determined using a suitable technique, such as a suitable chromatographical technique, such as polyacrylamide-gel electrophoresis;

k) The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein);

l) The term "antigenic determinant" refers to the epitope on the antigen recognized by the antigen-binding molecule (such as a Nanobody or a polypeptide of the invention) and more in particular by the antigen-binding site of said molecule. The terms "antigenic determinant" and "epitope" may also be used interchangeably herein.

m) An amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

n) The term "specificity" refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences. Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably 10 to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant ($K_A$), by means of the relationship $[K_D=1/K_A]$.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT.ln($K_D$) (equivalently DG=−RT.ln($K_A$)), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units $M^{-1}$ s$^{-1}$. The on-rate may vary between $10^2$ $M^{-1}$ s$^{-1}$ to about $10^7$ $M^{-1}$ s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}$=0.69 s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of Kr may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance. Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an IC$_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref} \ll K_{D\ ref}$, $K_D \approx IC_{50}$. Provided the measurement of the IC$_{50}$ is performed in a consistent way (e.g. keeping $c_{ref}$ fixed) for the binders that are compared, the strength or stability of a molecular interaction can be assessed by the IC$_{50}$ and this measurement is judged as equivalent to $K_D$ or to apparent $K_D$ throughout this text.

o) The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomologus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

p) As further described herein, the total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein;

q) The amino acid residues of a Nanobody are numbered according to the general numbering for V$_H$ domains given by Kabat et al. ("Sequence of proteins of immunological interest", US Public Health Services, NIH Bethesda, Md. Publication No. 91), as applied to V$_{HH}$ domains from Camelids in the article of Riechmann and Muyldermans, J. Immunol. Methods 2000 Jun. 23; 240 (1-2): 185-195 (see for example FIG. 2 of this publication); or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of $V_H$ domains, which methods can also be applied in an analogous manner to $V_{HH}$ domains from Camelids and to Nanobodies, are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise;

r) For the purposes of this application, "in or close to the complementarity determining regions (CDRs)" means that CDR1 comprises the amino acid residues at positions 27 to 35 (using Kabat numbering system). CDR2 comprises the amino acid residues at positions 50 to 65 or less than 65, e.g. 58, and CDR3 comprises the amino acid residues at positions 95-102; and s) The Figures, Sequence Listing and the Experimental Part/Examples are only given to further illustrate the invention and should not be interpreted or construed as limiting the scope of the invention and/or of the appended claims in any way, unless explicitly indicated otherwise herein.

The principle underlying the invention is schematically illustrated by the non-limiting FIG. 1, which shows a pool of oligonucleotides comprising a series of oligonucleotides (a) to (e) which can be assembled, by means of PCR assembly, into a nucleotide sequence (1) that encodes the amino acid sequence (2), which is an amino acid sequence can be used as a single antigen-binding domain. In addition to the oligonucleotides (a) to (e), the pool also contains a number of variants of the oligonucleotides (b) and (d), respectively, which are indicated as FIG. 1 as $(b^1)$, $(b^2)$, $(b^3)$ and $(d^1)$, $(d^2)$ and $(d^3)$, respectively. The variants $(b^1)$, $(b^2)$, $(b^3)$ of the oligonucleotide (b) differ from the oligonucleotide (b) in that they each encode an amino acid sequence that differs from the amino acid sequence encoded by the oligonucleotide (b)—and also from the amino acid sequences that are encoded by the other variants of the oligonucleotide (b) that are used as part of the pool—by the presence of one or more specific mutations (as defined herein), which specific mutations are schematically indicated by a dot, square or triangle in FIG. 1. Similarly, the variants $(d^1)$, $(d^2)$, $(d^3)$ of the oligonucleotide (d) differ from the oligonucleotide (d) in that they each encode an amino acid sequence that differs from the amino acid sequence that is encoded by the oligonucleotide (d)—and also from the amino acid sequences that are encoded by the other variants of the oligonucleotide (d) that are used as part of the pool—by the presence of one or more specific mutations, again schematically indicated by a dot, square or triangle in FIG. 1. When the pool of oligonucleotides is subjected to PCR assembly, the result is a series of nucleotide sequences (indicated in FIG. 1 as $1^A$, $1^B$ $1^C$, $1^D$, etc., respectively) that each encode a different analog (indicated in FIG. 1 as $2^A$, $2^B$, $2^C$, $2^D$, etc., respectively) of the amino acid sequence (2), in which each analog differs from the amino acid sequence (2)—and from the other analogs obtained after PCR assembly—by the presence of one or more specific mutations. The result is a set, collection or library of amino acid sequences (2, $2^A$, $2^B$, $2^C$, $2^D$ etc.) that each are suitable or intended for use as a single antigen-binding domain and that differ from each other by the presence of the one or more specific mutations. This set, collection or library (or the individual amino acid sequences 2, $2^A$, $2^B$, $2^C$, $2^D$, etc. present therein) can then be tested or screened for the presence of one or more desired properties (or any suitable combination of desired properties).

Usually, in the practice of the invention, the specific mutation(s) (as defined herein) will comprise a substitution of the amino acid residue that is present at the position to be varied (as defined herein) by another amino acid residue. However, it should be noted that according to the invention in its broadest sense, a specific mutation (as defined herein) may also comprises a deletion of the amino acid residue that is present at the position to be varied (as defined herein), or may comprise an insertion of an amino acid residue at the position to be varied.

As also mentioned above, according to one preferred but non-limiting aspect, the invention can be used to provide a series of analogs of a known or predetermined starting sequence, which analogs differ from the starting sequence (and from each other) in the presence of one or more (predetermined) specific mutations (as defined herein), and which analogs can be tested or screened for one or more desired properties (or combination of desired properties). It will be clear to the skilled person that, depending on how the oligonucleotides used in step a) are chosen, the methods described herein will often lead to a set, collection or library of assembled nucleotide sequences in which one of the assembled nucleotide sequences will encode the predetermined amino acid sequence, and which one or more of the further nucleotide sequences each encode an analog of said predetermined amino acid sequence. This will usually be preferred in practice, since it allows the predetermined sequence to be used as a reference in subsequent testing or screening of the analogs. However, if desired, it is also possible to choose the oligonucleotides used in step a) in such a way that they can be assembled into a set, collection or library of nucleotide sequences that only encodes analogs of the predetermined sequence.

Generally, the methods described herein can be used to modify (or to try to modify), and in particular to improve (or to try to improve), any desired property or combination of properties of the starting sequence, and such properties or combination of properties will be clear to the skilled person based on the disclosure herein. Generally, such properties will be properties that are determined or influenced by the presence of absence of one or more specific amino acid residues in (the primary sequence of) the amino acid sequence of interest (which of course may also influence the secondary and/or tertiary structure of the amino acid sequence and in this way influence the properties of the amino acid sequence). These properties for example include, the affinity or specificity for an intended antigen (meaning that the methods described herein are used for affinity maturation of the starting sequence), the potency or activity (i.e. in suitable in vitro, cellular or in vivo assay or model), the selectivity, the solubility, the stability (for example, thermal stability; stability under storage, stability at different pH values, and/or stability in different biological fluids or conditions, such as serum or the gut; stability of pharmaceutical preparations comprising the amino acid sequence; resistance to (auto-)oxidation), the tendency to aggregate, the "stickyness", the folding of the amino acid sequence, the degree of sequence identity with the closest human (and/or llama or camel) germline sequence (meaning that the methods described herein may be used for humanization or camelization of the starting sequence, and to determine the influence thereof on the properties of the sequence, such as the influence thereof on one or more of the further properties mentioned herein), the presence of epitopes that might be recognized by the human immune system and the potential immunogenicity (if any) of the sequence (meaning that the methods described herein are used for deimmunization, and to determine the influence thereof on the properties of the sequence, such as the influence thereof on one or more of the further properties mentioned herein), the presence of one or more amino acid residues or of a stretch of amino acid residues that allow(s) the amino acid sequence to undergo one or more interactions other than the interaction with the intended antigen (meaning that the methods of the invention may for example be used in order to introduce a second binding site for interaction with another antigen), the expression levels in a desired host or host cell, the half-life, the presence or absence of sites or amino acid residues that can be modified (e.g. pegylated, glycolysated and/or that can be modified as part of post-translational modification), the presence or absence of sites or amino acid residues that are subject to oxidation (e.g. during production/expression or under storage), the presence or absence of cysteine residues that can form disulphide bridges, etc; or any desired combination of any of the foregoing. In doing so, the objective may either be to improve one or more of these properties, and/or to establish a proper balance between two or more of these properties.

It will also be clear to the skilled person that, where the amino acid sequences generated using the methods described herein comprise framework regions and complementarity determining regions, that the one or more specific mutations can be present in any one or more of the framework regions, in any one or more of the complementarity determining regions, or in both any of the framework regions and any of the complementarity determining regions.

In one non-limiting aspect, the one or more specific mutations are present only in the framework regions. In another non-limiting aspect, the one or more specific mutations are present only in the framework regions.

It will also be clear to the skilled person that, when it is intended to modify or improve some of the specific properties listed above, that for this purpose, specific mutations in the framework regions may be preferred (i.e. to "vary" positions in the framework regions). Similarly, for the purpose of modifying improving some of the other specific properties specific mutations in the complementarity determining regions may be preferred (i.e. to "vary" positions in the complementarity determining regions). Also, of course, for the purpose of modifying or improving a combination of two or more of such properties, it may be preferred to have specific mutations in both the framework regions as well as the complementarity determining regions (i.e. to "vary" positions in both the framework regions as well as the complementarity determining regions).

Generally, it will be clear to the skilled person, based on the disclosure and the prior art cited herein, whether amino acid positions in the framework regions or whether amino acid positions in the complementarity determining regions are associated with a specific property of the amino acid sequence, and thus whether amino acid positions in the framework regions or whether amino acid positions in the complementarity determining should chosen can potential positions that can be (or should be) varied (as defined herein) in order to try to modify or improve said property.

It will also be clear to the skilled person, based on the disclosure and the prior art cited herein, that certain positions in the amino acid sequence may be highly conserved between different representatives of the class of amino acid sequences. For example, for Nanobodies, as can be seen from Table A-5 below, the amino acid residues such as those at positions 4, 9, 22, 38 and 86 show a $V_{HH}$ entropy of essentially zero and a $V_{HH}$ variability of essentially 1, and although it is not excluded that these positions are varied (as defined herein) by the methods described herein, these positions may in specific cases not be the most preferred candidates for introducing specific mutations (as defined herein).

It may sometimes even be clear to the skilled person, based on the disclosure and the prior art cited herein, whether certain specific amino acid positions or amino acid residues (either in the framework regions and/or in the complementarity determining regions) are or may be associated with a specific property of the amino acid sequence, and thus whether said specific positions or amino acid residues should be varied (as defined herein) in order to try to modify or improve said property.

Thus, based on the disclosure herein and depending on the property or properties to be modified or improved, the skilled person will be able to choose specific amino acid positions in the amino acid sequence that are suitable candidates for the introduction of specific mutations (as defined herein), optionally after a limited degree of trial and error, i.e. by introducing a limited number of specific mutations (as defined herein) at said position and determining the effect on the property or properties of interest.

Also, as further described herein, the methods described herein may be used to provide a set, collection or library of amino acid sequences that contain one or more "random" mutations at one or more predetermined positions. It is also possible, using the methods described herein, to provide a set, collection or library of amino acid sequences that contain one or more "random" mutations at one or more predetermined positions as well as one or more predetermined specific mutations (as defined herein) at one or more other amino acid positions. Again, either set, collection or library (or individual sequences within said library) can be screened or tested for one or more desired or improved (i.e. compared to a known starting sequence) properties.

Also, as mentioned herein, the methods described herein may be used to provide a set, collection or library of nucleic acids or nucleotide sequences that have one or more desired or improved (i.e. compared to a known starting sequence)

properties compared to a starting nucleic acid or nucleotide sequence. For example, according to this aspect, the different nucleic acids or nucleotide sequences within said set, collection or library may all encode the same amino acid sequence (e.g. the same amino acid sequence as encoded by the starting sequence), but differ from each other by the codons used (i.e. due to the degeneracy of the genetic code).

The skilled person will also be able to choose suitable amino acid residues that can be introduced and tested as specific mutations (as defined herein) at the position(s) to be varied (as defined herein) using the methods described herein (or alternatively, amino acid residues to be deleted or inserted), again optionally after a limited degree of trial and error, i.e. by introducing a limited number of specific amino acid residues at the position(s) to be varied (as defined herein) and determining the effect on the property or properties of interest. For example, such amino acid residues may be chosen such that the specific mutation is a conservative amino acid substitution (as defined herein) or such that the specific mutation is not a conservative amino acid substitution.

It will also be clear to the skilled person that the methods described herein can also be used to determine which position(s) in an amino acid sequence are associated with certain properties of the amino acid sequence, and if and how deletions, insertions or substitutions of specific amino acid residues at said position(s) can influence said property or properties. By doing so, the methods described herein may even be a convenient means that can be used to derive certain "structure activity relationships" between the amino acid residues present at certain positions in the sequence and the desired properties of the sequence. As will be clear to the skilled person, this may be valuable for research purposes (e.g. for epitope mapping and/or paratope mapping), but also when the methods described herein are used to increase the affinity or specificity of a sequence for an intended target (i.e. as a means of affinity maturation of a starting sequence).

For example and without limitation, when the methods described herein are to be used for modifying or improving the affinity or specificity of a sequence for an intended antigen (i.e. for affinity maturation), specific mutations (as defined herein) will usually be introduced in one or more of the complementarity determining regions. Such positions and residues that can be introduced and tested at these positions will be clear to the skilled person based on the disclosure and prior art cited herein. It will also be clear to the skilled person that such specific mutations may also be introduced and tested in order to modify or improve the potency or activity in a suitable in vitro, cellular or in vivo assay or model.

More generally, the invention may also be used to generate a series of analogs that can each be tested for potency or activity in a suitable in vitro, cellular or in vivo assay or model.

When the methods described herein are to be used for modifying or improving the solubility, the stability, the tendency to aggregate, the "stickyness" of a sequence, specific mutations (as defined herein) will usually be introduced in one or more of the framework regions, and in particular at those positions in the framework regions that positions that are surface exposed and/or that form the contact residues or interface for interaction with other amino acid residues (for example, the amino acid residues that form the $V_H$/VL interface). Such positions and residues that can be introduced and tested at these positions will be clear to the skilled person based on the disclosure and prior art cited herein (for example, for $V_{HH}$ sequences or Nanobodies, specific mutations may be introduced and tested at one or more of the Hallmark residues and/or at one or more other positions). It will also be clear that, according to this non-limiting aspect, the methods of the invention can be used to introduce and test so-called "camelizing" substitutions (as further described herein). It will also be clear to the skilled person that such specific mutations may be introduced and tested in order to modify or improve the expression levels in a desired host or host cell.

When the methods described herein are to be used for modifying or improving the folding of the amino acid sequence (such as formation of an alpha-helix, beta-sheet, immunoglobulin fold or "loops-and-barrel structure), specific mutations (as defined herein) will usually be introduced at positions that are involved in the folding of the amino acid sequence. Such positions and residues that can be introduced and tested at these positions will be clear to the skilled person based on the disclosure and prior art cited herein, and will often be present in the framework regions. It will also be clear to the skilled person that such specific mutations may be introduced and tested in order to modify or improve the expression levels in a desired host or host cell. The methods described herein may also be used to introduce and test specific mutations that are intended to modify the flexibility or rigidity of the CDR's. Usually such specific mutations will be introduced at positions in the sequence that are either in the CDR's or close to the CDR's, and such positions and residues to be introduced will be clear to the skilled person based on the disclosure and prior art cited herein.

When the methods described herein are to be used for modifying or improving the degree of sequence identity with the closest human germline sequence (i.e. for humanization), specific mutations (as defined herein) will usually be introduced in one or more of the framework regions (although the invention is not limited thereto, and may also comprise one or more specific mutations in the CDR's, in particular at amino acid positions that have a low sequence entropy (e.g. $V_{HH}$ entropy, as described herein) and/or low sequence variability (e.g. $V_{HH}$ variability, as described herein)). Such positions and residues that can be introduced and tested at these positions will be clear to the skilled person based on the disclosure and prior art cited herein.

For example, suitable positions to be varied (as defined herein) and suitable humanizing amino acid residues to be introduced at said position may also be determined by comparing the starting amino acid sequence with one or more of the closest human germline sequences. For example, for $V_{HH}$ sequences (and more generally for providing Nanobodies), one or more suitable humanizing specific mutations (or any suitable combination thereof) that can be introduced and tested using the methods described herein will be clear to the skilled person based on the further disclosure herein, and include the potential humanizing substitutions indicated for $V_{HH}$ sequences and Nanobodies in the further disclosure herein (i.e. at one or more of the Hallmark residues and/or at one or more other positions).

When the methods described herein are to be used for modifying (and in particular removing) epitopes that might be recognized by the human immune system, specific mutations (as defined herein) will usually be introduced at positions that (potentially) correspond to such epitopes. Such positions and residues that can be introduced and tested at these positions will be clear to the skilled person based on the disclosure and prior art cited herein. For example, various in silico and in vitro techniques for mapping epitopes that might potentially be recognized by the human immune system (i.e. by T-cells) are becoming available, such as the EpiBase™ technology of Algonomics (Ghent, Belgium) or the EpiScreen™ technology of Antitope (Cambridge, UK). These and similar techniques can be used to map potential T-cell epitopes in the amino acid sequence, at which specific mutations (as defined herein) may then be introduced and tested using the methods described herein, which specific mutations are preferably such that they remove the T-cell epitopes. It will also be clear to the skilled person that such specific mutations may be introduced and tested in order to modify or improve the potential immunogenicity (if any) of the amino acid sequence.

The methods described herein may also be used to introduce and test specific mutations that are intended to introduce or to remove one or more amino acid residues (or of a stretch of amino acid residues) that will allow(s) the amino acid sequence to undergo one or more interactions other than the interaction with the intended antigen. Such positions and residues that can be introduced and tested at these positions will be clear to the skilled person based on the disclosure and prior art cited herein. It will also be clear to the skilled person that such specific mutations may be introduced and tested in order to modify or improve the solubility, the stability, the tendency to aggregate, the "stickyness" and/or the expression levels in a desired host or host cell.

For example, the methods described herein may be used to introduce and test specific mutations that are intended to introduce a second binding site in the amino acid residues for interaction with an antigen other than the antigen to which the CDR's are directed. For such positions, which are usually positions in the framework regions such as positions in the "bottom loops", reference is for example made to Keck and Huston, Biophysical Journal 71, October 1996, 2002-2011; EP 0 640 130 and WO 06/072620, as well as the U.S. provisional application 60/861,182 by Ablynx N.V. entitled "Immunoglobulin domains with multiple binding sites", filed on Nov. 27, 2006. As described herein, such second binding sites may for example be introduced in order to modify or improve the half-life of the amino acid sequence, for example by introducing a second binding site for binding to a serum protein such as serum albumin.

The methods described herein may also be used to introduce and test specific mutations that are intended to introduce or to remove sites can be subjected to post-translational modification (for example the formation of a disulphide bridge or glycolysation, depending on the host or host cell used for expression) or that can otherwise be modified (for example by pegylation). Such positions and residues that can be introduced and tested at these positions will be clear to the skilled person based on the disclosure and prior art cited herein, and may for example involve suitably introducing or removing one or more cysteine residues that can be glycosylated, pegylated or form a disulphide bridge. It will also be clear to the skilled person that such specific mutations may be introduced and tested in order to modify or improve the solubility, the stability, the tendency to aggregate, the "stickyness" and/or the expression levels in a desired host or host cell.

Although the invention is not particularly limited as to the size of the amino acid sequence (2) and analogs that are prepared using the methods described herein (any such limitations will mainly be of a practical nature, such as the size of the nucleotide sequences that can be efficiently assembled by PCR using the envisaged primers), the invention may for example be used to prepare amino acid sequences or variants (and/or nucleotide sequences or nucleic acids encoding the same) that comprise between about 10 and about 1000, such as between about 20 and about 500 amino acid residues, and in particular between 50 and 200 amino acid residues, such as about 75 to 150 amino acid residues (e.g. the usual size of $V_H$, $V_L$ or $V_{HH}$ domains. For example, $V_{HH}$ domains may comprise between 110 and 140 amino acid residues, depending on the length of the CDR's present therein).

The number of positions that are varied (as defined herein) using the methods described herein may be suitably chosen, and may vary from a single position to ten or more positions, but is usually one, two, three, four, five, six, seven, eight, nine, or ten positions.

Similarly, the number of different amino acid residues that is introduced as a specific mutations (as defined herein) at each position so as to provide an analog as described herein may also be suitably chosen, and may vary from a single amino acid residue up to 20 or even more (for example, for making random collections or libraries of immunoglobulin variable domains, degenerate codons such as NNK or NNS may be introduced at up to 20 different predetermined amino acid positions or more), but is usually one, two, three, four, five, six, seven, eight, nine, or ten amino acid residues. Also, as mentioned above, the specific position or positions to be varied (as defined herein), as well as the specific amino acid residue or residues that are introduced and tested as specific mutations, may be suitably chosen by the skilled person based on the disclosure herein, and may depend on the amino acid residue that is present at the relevant position in the starting sequence, as well as the kind of modification that is intended to be tested (for example, going from a charged amino acid residue to an uncharged amino acid residue, or visa versa).

In practice, it will usually be preferred to choose the specific position or positions to be varied (as defined herein), as well as the specific amino acid residue or residues that are introduced and tested as specific mutations, as well as the number of positions that are varied and the number of different amino acid residues that are introduced at each position is such a way that the analogs and their relevant properties can be compared to each other (and optionally to the starting sequence) in a meaningful way, i.e. so as to choose or design the analog(s) with the optimal desired property or properties, and/or to draw conclusions as to the influence that a specific mutation or combination of specific mutations has on the desired property or properties. All this will be within the skill of the artisan based on the disclosure herein.

Thus, in another specific, but non-limiting aspect, the invention relates to a set, collection or library of nucleotide sequences or nucleic acids that encode amino acid sequences that can be used as (and/or are intended for use as) single antigen-binding domains, which set, collection or library of nucleotide sequences or nucleic acids can be obtained (or has been obtained) by means of PCR assembly, in which the nucleotide sequences or nucleic acids present in the set, collection or library encode amino acid sequences that differ from each other in the presence of one or more specific mutations (as defined herein). Again, such a set, collection or library may encode analogs of a predetermined starting sequence (and optionally a nucleotide sequence or nucleic acid encoding the predetermined starting sequence itself). Also, the amino acid sequences encoded by the nucleotide sequences or nucleic acids may be as further described herein.

In another specific, but non-limiting aspect, the invention relates to a set, collection or library of amino acid sequences that can be used as (and/or are intended for use as) single antigen-binding domains, which set, collection or library of amino acid sequences can be obtained (or has been obtained) by means of PCR assembly of a set, collection or libraries of nucleotide sequences or nucleic acids that encode said amino acid sequences followed by expression of said nucleotide sequences or nucleic acids, in which the amino acid sequences in the set, collection or library differ from each other in the presence of one or more specific mutations (as defined herein). Again, such a set, collection or library may comprise analogs of a predetermined starting sequence, such as—for example and without limitation—a $V_{HH}$ sequence or Nanobody (and optionally the starting sequence itself). Also, the amino acid sequences may be as further described herein.

In another specific, but non-limiting aspect, the invention relates to a set, collection or library of nucleotide sequences or nucleic acids that encode amino acid sequences that can be used as (and/or are intended for use as) single antigen-binding domains, which a set, collection or library of nucleotide sequences or nucleic acids can be obtained (or has been obtained) by means of PCR assembly, in which the nucleotide sequences or nucleic acids present in the set, collection or library encode amino acid sequences that differ from each other in the presence of one or more specific mutations (as defined herein) that are humanizing substitutions (or camelizing substitutions). Again, such a set, collection or library may encode humanized (or camelized) analogs of a predetermined starting sequence (and optionally a nucleotide sequence or nucleic acid encoding the predetermined starting sequence itself). Also, the amino acid sequences encoded by the nucleotide sequences or nucleic acids may be as further described herein. Thus, the invention also relates to a set, collection or library of nucleotide sequences or nucleic acids that encode amino acid sequences that can be used as (and/or are intended for use as) single antigen-binding domains and that comprise or essentially consist of 4 framework regions and 3 complementarity determining regions, which a set, collection or library of nucleotide sequences or nucleic acids can be obtained (or has been obtained) by means of PCR assembly, in which the nucleotide sequences or nucleic acids present in the set, collection or library encode amino acid sequences that differ from each other in the presence of one or more specific mutations that are humanizing substitutions (or camelizing substitutions), in which said humanizing substitutions are in the framework regions (for example, in one or more of the Hallmark positions and/or in one or more of the other positions).

In another specific, but non-limiting aspect, the invention relates to a set, collection or library of amino acid sequences that can be used as (and/or are intended for use as) single antigen-binding domains, which set, collection or library of amino acid sequences can be obtained (or has been obtained) by means of PCR assembly of a set, collection or libraries of nucleotide sequences or nucleic acids that encode said amino acid sequences followed by expression of said nucleotide sequences or nucleic acids, in which the amino acid sequences differ from each other in the presence of one or more specific mutations (as defined herein) that are humanizing substitutions (or camelizing substitutions). Again, such a set, collection or library may comprise humanized (or camelized) analogs of a predetermined starting sequence, such as—for example and without limitation—a $V_{HH}$ sequence or Nanobody (and optionally the predetermined starting sequence itself). Also, the amino acid sequences may be as further described herein. Thus, the invention also relates to a set, collection or library of amino acid sequences that can be used as (and/or are intended for use as) single antigen-binding domains and that comprise or essentially consist of 4 framework regions and 3 complementarity determining regions, which set, collection or library of amino acid sequences can be obtained (or has been obtained) by means of PCR assembly of a set, collection or libraries of nucleotide sequences or nucleic acids that encode said amino acid sequences followed by expression of said nucleotide sequences or nucleic acids, in which the amino acid sequences present in the set, collection or library differ from each other in the presence of one or more specific mutations that are humanizing substitutions (or camelizing substitutions), in which said humanizing substitutions are in the framework regions (for example, in one or more of the Hallmark positions and/or in one or more of the other positions).

The invention further relates to a set, collection or library of nucleotide sequences or nucleic acids that encode amino acid sequences that can be used as (and/or are intended for use as) single antigen-binding domains and that comprise or essentially consist of 4 framework regions and 3 complementarity determining regions, which a set, collection or library of nucleotide sequences or nucleic acids can be obtained (or has been obtained) by means of PCR assembly, in which the nucleotide sequences or nucleic acids present in the set, collection or library encode amino acid sequences that differ from each other in the presence of one or more specific mutations in one or more of the complementarity determining regions.

The invention also relates to a set, collection or library of amino acid sequences that can be used as (and/or are intended for use as) single antigen-binding domains and that comprise or essentially consist of 4 framework regions and 3 complementarity determining regions, which a set, collection or library of amino acid sequences can be obtained (or has been obtained) by means of PCR assembly of a set, collection or libraries of nucleotide sequences or nucleic acids that encode said amino acid sequences followed by expression of said nucleotide sequences or nucleic acids, in which the amino acid sequences present in the set, collection or library differ from each other in the presence of one or more specific mutations in one or more of the complementarity determining regions.

The invention further relates to a set, collection or library of nucleotide sequences or nucleic acids that encode amino acid sequences that can be used as (and/or are intended for use as) single antigen-binding domains, which set, collection or library of nucleotide sequences or nucleic acids can be obtained (or has been obtained) by means of PCR assembly, in which the nucleotide sequences or nucleic acids present in the set, collection or library encode amino acid sequences that differ from each other in the presence of one or more specific mutations in (and consequently in the presence or absence of) one or more epitopes that can be recognized by the human immune system.

The invention further relates to a set, collection or library of amino acid sequences that can be used as (and/or are intended for use as) single antigen-binding domains, which set, collection or library of amino acid sequences can be obtained (or has been obtained) by means of PCR assembly of a set, collection or libraries of nucleotide sequences or nucleic acids that encode said amino acid sequences followed by expression of said nucleotide sequences or nucleic acids, in which the amino acid sequences that differ from each other in the presence of one or more specific mutations in (and consequently in the presence or absence of) one or more epitopes that can be recognized by the human immune system.

The oligonucleotides that are used in the methods described herein may be any suitable set or series of oligonucleotides, as long as they can be assembled (i.e. by assembly PCR) into a set, collection or library of nucleotide sequences that encodes the desire set, collection or library of amino acid sequences (i.e. the series of analogs, with or without the starting sequence). Based on the disclosure and prior art cited herein, as well as his general knowledge of assembly PCR, the skilled person will be able to suitably choose (i) a series of at least two oligonucleotides that can be assembled into the full-sized nucleotide sequence, and also to suitably choose (ii) the variants of some of said oligonucleotides that encode the specific mutations (as defined herein) that are to be introduced into the analogs.

The size of the oligonucleotides used will depend on the size of the amino acid sequence (2) and variants to be assembled, as well as the number of specific or random mutations to be introduced. Generally, the size of the oligonucleotides (including any overlap between them) may be suitably chosen by the skilled person based on the disclosure herein.

For example, and without limitation, for assembling a set of nucleotide sequences or nucleic acids that encode a $V_H$, $V_L$ or $V_{HH}$ domain, suitable oligonucleotides will have a length of between about 10 and about 200 nucleotides, and in particular between about 20 and about 100 nucleotides, such as about 30, 40, 50, 60 or 70 nucleotides, with suitable overlaps between the oligos of about 10 to about 30 nucleotides, such as about 15 nucleotides; which generally means that for assembling a set of nucleotide sequences or nucleic acids that encode a $V_{11}$, $V_L$ or $V_{HH}$ domain, between about 4 to about 40, such as between about 5 and about 20, such as about 6, 8, 10, 12 or 16 different oligos can be used. Oligos of similar size, and/or a similar number of different oligos, may be used for producing other proteins or polypeptide. It will also be clear to the skilled person that not all the oligonucleotides used in step a) will need to have exactly the same length, nor for example that the oligonucleotides will need to correspond exactly to the framework sequences or CDR's, respectively. However, it will be clear to the skilled person that in order to allow the oligonucleotides to be assembled, the oligonucleotides must suitably have short overlapping segments of nucleotides and also suitably alternate between sense and antisense directions (see for example Stemmer et al., supra, and some of the further prior art cited herein), and that the variants of an oligonucleotide will generally have the same length as the oligonucleotide (unless, for example, the variant contains one or more insertions or deletions as specific mutations). Also, most preferably, the oligonucleotides are preferably chosen and designed such that the specific mutations are not part of the short overlapping segments.

The oligonucleotides used may be obtained in any manner known per se, for example using methods for (automated) DNA synthesis known per se.

Each of the oligonucleotides and variants thereof that are used in the methods described herein may be added to the PCR assembly reaction in any amount(s) suitable to provide the desired amino acid sequence (2) and the desired analogs thereof. In doing so, and without limitation, the oligonucleotides and their variants may be added in equimolar amounts or in non-equimolar amounts. In case it is desired to generate an amino acid sequence (2) and analogs thereof that have an equal distribution of specific mutations on a given position, equimolar amounts of the oligonucleotide and the variant(s) thereof that encompass said position and encode the desired amino acid residue and specific mutation(s) will be added to the reaction mixture. In case an uneven distribution of specific mutations is desired, the ratio of the encoding oligonucleotide and its variants can be adjusted accordingly (e.g. if the original, natural or wild-type amino acid is preferred on a given position the concentration of the encoding oligonucleotide may be increased relative to the analogous oligonucleotides).

The PCR assembly reaction may be performed in any suitable manner known per se, for which again reference is made to Stemmer et al., supra, and to some of the further prior art cited herein.

Conveniently, the PCR assembly reaction may be performed as a single-step PCR reaction. The assembly reaction may either be performed in a single reaction mixture that comprises a "pool" of all oligonucleotides, or may be performed by means of parallel reactions using a series of reaction mixtures in which the oligonucleotides present in each reaction mixture are such that, upon assembly, each reaction mixture affords a different analog. The latter may for example be performed in a suitable multi-well format, and may also be suitably automated.

Furthermore, after assembly, the nucleotide sequences that encode the full-length amino acid sequence/variants may be generated (i.e. "rescued") by a (final) amplification using forward and reverse primers that anneal to the 3'-end and the 5' end, respectively, of the nucleotide sequence(s) that encode the desired amino acid sequence/variants.

After the PCR assembly, the nucleotide sequences encoding the analogs may be suitably isolated, purified, cloned and/or expressed using any suitable technique or combination of techniques known per se. Upon expression, the analogs thus obtained may then be tested or screened for the one or more desired properties or combination of properties, using any suitable method, technique or assay or combination of techniques known per se, as further described herein.

Suitable techniques for isolating, purifying, cloning and/or expressing the nucleotide sequences will be clear to the skilled person based on the disclosure and prior art cited herein. Similarly, suitable techniques for testing or screening the analogs for the one or more desired properties or combination of properties will also be clear to the skilled person based on the disclosure and prior art cited herein.

As also mentioned above, the sequences that can be generated using the methods described herein can be (or can encode) immunoglobulin sequences, i.e. sequences that contain an immunoglobulin fold or that are capable of forming, i.e. by folding under appropriate circumstances, an immunoglobulin fold. Similarly, the methods described herein can be used to generate a series of analogs of a starting sequence that comprises an immunoglobulin fold or that is capable of forming an immunoglobulin fold.

More in particular, the sequences that can be generated using the methods described herein can comprise or essentially consist of (or can encode) an immunoglobulin variable domain sequence or a suitable fragment thereof, such as light chain variable domain sequence (e.g. a $V_L$-Sequence) or a suitable fragment thereof; or a heavy chain variable domain sequence (e.g. a $V_H$-sequence) or a suitable fragment thereof (in the context of the present invention, a "suitable fragment" of a variable domain sequence is a fragment that is suitable for use as a single antigen-binding domain, that is (still) capable of specific binding (as defined herein) to the intended antigen, and that preferably also still contains an immunoglobulin fold or is capable of forming an immunoglobulin fold. Such suitable fragments will be clear to the skilled person based on the disclosure herein, and may for example also comprise two or more smaller fragments that are suitably linked to each other to form a larger fragment).

When the sequence that is generated using the methods described herein is (or encodes) a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein), or a suitable fragment thereof.

Similarly, the methods described herein can be used to generate a series of analogs of a $V_L$ sequence, a $V_H$ sequence or a $V_{HH}$ sequence that is used as a starting sequence.

In particular, but without limitation, the sequences that can be generated using the methods described herein may be (or may encode) sequences that essentially consist of 4 framework regions (FR1 to FR4 respectively) and 3 complementarity determining regions (CDR1 to CDR3 respectively); or any suitable fragment of such a sequence (which fragments will then usually contain at least some of the amino acid residues that form at least one of the CDR's, as further described herein). Similarly, the methods described herein can be used to generate a series of analogs such a sequence that is used as a starting sequence.

For example, the sequences that can be generated using the methods of the invention may comprise (or may encode) a domain antibody or an amino acid sequence that is suitable for use as a domain antibody, a single domain antibody or an amino acid sequence that is suitable for use as a single domain antibody, a "dAb'" or an amino acid sequence that is suitable for use as a dAb, or (preferably) a Nanobody™, or any suitable fragment thereof. Similarly, the methods described herein can be used to generate a series of analogs of a domain antibody, of a single domain antibody, of a "dAb'" or of a Nanobody™ that is used as a starting sequence.

As mentioned herein, the methods described herein can be in particular be used to provide (improved) amino acid sequences that can be used as single antigen-binding domains.

As such, the amino acid sequences that are provided by the methods described herein may be directed against (as defined herein) any suitable or desired antigen, target or protein. As will be clear to the skilled person, this will usually be determined by the CDR's or other antigen-binding sites or residues that are present in the amino acid sequence, which in turn will usually be determined by the choice of the starting sequence. Generally, the amino acid sequences that are provided by the methods described herein will be capable of specific binding (as defined herein) to the intended or desired antigen, target or protein.

More in particular, an amino acid sequence that can be generated using the methods described herein may be such that it:

i) binds to the intended or desired target with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that it:

ii) binds to the intended or desired target with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^3$ $M^{-1}$ $s^{-1}$, more preferably between $10^4$ $M^{-1}$ $s^{-1}$ and $10^7$ $M^{-1}$ $s^{-1}$, such as between 10 $M^{-1}$ $s^{-1}$ and $10^7$ $M^{-1}$ $s^{-1}$;

and/or such that it:

iii) binds to the intended or desired target with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-6}$ $s^{-1}$ and $10^{-6}$ $s^{-1}$, such as between $10^{-4}$ $s^{-1}$ and 10 $s^{-1}$.

For example, a monovalent amino acid sequence that can be generated using the methods may be such that it will bind to the intended or desired target with an affinity less than 500 nM, preferably less than 200 nM, more preferably less than 10 nM, such as less than 500 pM.

In one particularly preferred, but non-limiting aspect, the methods described herein may be used to provide a set, collection or library of Nanobody sequences, starting from a naturally occurring or wildtype $V_{HH}$ sequence (i.e. obtained in a manner known per se, for which reference is for example made to the prior art on Nanobodies and $V_{HH}$ sequences cited herein). This set, collection or library of Nanobody sequences (or individual Nanobody sequences from said set, collection or library) may then be screened or tested in order to provide Nanobody sequences that have one or more desired or improved properties, compared to the wildtype $V_{HH}$ sequence that is used as the predetermined starting sequence.

In particular, according to this aspect, the methods described herein may be used to provide a set, collection or library of humanized Nanobodies, starting from a naturally occurring or wildtype $V_{HH}$ sequence. Individual humanized Nanobody sequences from said set, collection or library) may then be tested in order to determine the influence of the one or more humanizing substitutions on the properties of the Nanobody (and in particular whether, upon introducing the one or more humanizing substitutions, the sequences obtained retain the favourable properties of a Nanobody), and/or this set, collection or library of humanized Nanobody sequences may be screened for Nanobody sequences that have one or more desired or improved properties, compared to the naïve $V_{HH}$ sequence that is used as the predetermined starting sequence. Suitable humanizing substitutions that can be tested/introduced as specific mutations using the methods described herein will also be clear from the further description herein (see for example Tables A-3 to A-8) below, and may include one or more humanizing substitutions at one or more of the Hallmark residues and/or one or more humanizing substitutions at other positions in the Nanobody sequence.

In another particularly preferred, but non-limiting aspect, the methods described herein may be used to provide a set, collection or library of Nanobody sequences that have one or more specific mutations in one or more of the CDR's, starting from a naturally occurring or naïve $V_{HH}$ sequence. This set, collection or library of Nanobody sequences (or individual Nanobody sequences from said set, collection or library) may then be screened or tested in order to provide Nanobody sequences that have improved affinity and/or specificity for a desired antigen, compared to the naïve $V_{HH}$ sequence or another Nanobody sequence that is used as the predetermined starting sequence. As will be clear to the skilled person, according to this aspect, the invention allows for affinity maturation of a naïve $V_{HH}$ sequence or another Nanobody sequence.

In yet another particularly preferred, but non-limiting aspect, the methods described herein may be used to provide a set, collection or library of camelized $V_H$ sequences, starting from a naturally occurring or naïve $V_H$ sequence (i.e. obtained in a manner known per se). This set, collection or library of camelized $V_H$ sequences (or individual camelized $V_H$ sequences from said set, collection or library) may then be screened or tested in order to provide sequences that have one or more desired or improved properties, compared to the naïve $V_{HH}$ sequence that is used as the predetermined starting sequence. In particular, individual camelized $V_H$ sequences from said set, collection or library may then be tested in order to determine the influence of the one or more camelizing substitutions on the properties of the $V_H$ sequence (and in particular whether such camelizing substitutions confer upon the $V_H$ sequence one or more of the favourable properties that are characteristic of a Nanobody), and/or this set, collection or library of camelized $V_H$ sequences may be screened for sequences that have one or more of the favourable properties that are characteristic of a Nanobody. Suitable camelizing substitutions that can be tested/introduced as specific mutations using the methods described herein will also be clear from the further description herein (see for example Tables A-3 to A-8 below, and may include one or more camelizing substitutions at one or more of the Hallmark residues (which will usually be preferred) and/or one or more humanizing camelizing at other positions in the Nanobody sequence.

In a further aspect, the invention relates to a protein or polypeptide that comprises or essentially consists of at least one amino acid sequence that has been generated using the methods described herein (or the amino acid sequence of which or the nucleotide sequence of which has been generated using the methods described herein, whereupon the actual amino acid sequence, nucleotide sequence, protein or polypeptide has been prepared using any suitable technique known per se), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence of the invention (and/or to the compound or construct in which it is present) and may or may not modify the properties of the amino acid sequence of the invention.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more amino acid sequences of the invention so as to provide a "derivative" of an amino acid sequence or polypeptide of the invention, as further described herein.

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are amino acid sequences.

In the compounds or constructs described above, the one or more amino acid sequences of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion (protein) or fusion (polypeptide).

The compounds or polypeptides of the invention can generally be prepared by a method which comprises at least one step of suitably linking the one or more amino acid sequences of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted amino acid sequences form a further aspect of the invention.

In one specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein.

In another aspect, the invention relates to a nucleic acid that encodes an amino acid sequence of the invention or a polypeptide of the invention (or a suitable fragment thereof). Such a nucleic acid will also be referred to herein as a "nucleic acid of the invention" and may for example be in the form of a genetic construct, as further described herein.

In another aspect, the invention relates to a host or host cell that expresses (or that under suitable circumstances is capable of expressing) an amino acid sequence of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention, at least one polypeptide of the invention (or a suitable fragment thereof) and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

In the further description below, the invention will be explained and illustrated in more detail by reference to one of its preferred but non-limiting aspects, i.e. in which the amino acid sequences provides by the methods described herein are Nanobodies and/or in which the methods described herein are used to provide improved Nanobodies, taking a $V_{HH}$ sequence and/or the sequence of another Nanobody as a starting point.

It should however be noted that the present invention can similarly be used to provide any other amino acid sequences that can be used as single antigen binding domains (and which amino acid sequences are as further defined herein) and/or to improve any other amino acid sequences that can be used as single antigen binding domains, such as a domain antibody, single domain antibody or dAb. This will also be clear to the skilled person based on the disclosure herein.

For a general description of Nanobodies, reference is made to the further description herein as well as to the prior art cited herein. In this respect, it should however be noted that this description and the prior art mainly described Nanobodies of the so-called "$V_{H3}$ class" (i.e. Nanobodies with a high degree of sequence homology to human germline sequences of the $V_H3$ class such as DP-47, DP-51 or DP-29). It should however be noted that the invention in its broadest sense generally covers any type of Nanobody that can be generated using the methods described herein and for example also covers the Nanobodies belonging to the so-called "$V_H4$ class" (i.e. Nanobodies with a high degree of sequence homology to human germline sequences of the $V_{11}4$ class such as DP-78), as for example described in the U.S. provisional application 60/792,279 by Ablynx N.V. entitled "DP-78-like Nanobodies" filed on Apr. 14, 2006.

Generally, Nanobodies (in particular $V_{HH}$ sequences and partially humanized Nanobodies) can in particular be characterized by the presence of one or more "Hallmark residues" (as described herein) in one or more of the framework sequences (again as further described herein).

Thus, generally, a Nanobody can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein, and in which the framework sequences are further as defined herein.

More in particular, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 45 according to the Kabat numbering is a charged amino acid (as defined herein) or a cysteine residue, and position 44 is preferably an E;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q; and/or in which:
b) the amino acid residue at position 45 according to the Kabat numbering is a charged amino acid or a cysteine and the amino acid residue at position 44 according to the Kabat numbering is preferably E;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are such that the Nanobody binds to its intended or desired target with:
   i) a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
   ii) and/or
   iii) a $k_{on}$-rate of between $10^2$ M$^{-1}$ s$^{-1}$ to about $10^7$ M$^{-1}$ s$^{-1}$ preferably between $10^3$ M$^{-1}$ s$^{-1}$ and $10^7$ M$^{-1}$ s$^{-1}$, more preferably between $10$ M$^{-1}$ s$^{-1}$ and $10^7$ M$^{-1}$ s$^{-1}$, such as between $10^8$ M$^{-1}$ s$^{-1}$ and $10^7$ M$^{-1}$ s$^{-1}$;
   iv) and/or:
   v) with a $k_{off}$ rate between $1$ s$^{-1}$ ($t_{1/2}$=0.69 s) and $10^{-6}$ s$^{-1}$ (providing a near irreversible complex with a $t_{1/2}$ of multiple days), preferably between $10^{-2}$ s$^{-1}$ and $10^{-6}$ s$^{-1}$, more preferably between $10^{-3}$ s$^{-1}$ and $10^{-6}$ s$^{-1}$, such as between $10^{-4}$ s$^{-1}$ and $10^{-6}$ s$^{-1}$.

In particular, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or
b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, according to a preferred, but non-limiting aspect, a Nanobody may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q; and/or in which:
b) the amino acid residue at position 44 according to the Kabat numbering is E and in which the amino acid residue at position 45 according to the Kabat numbering is an R; and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein.

In particular, a Nanobody may have the structure:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q; and/or in which:
b) the amino acid residue at position 44 according to the Kabat numbering is E and in which the amino acid residue at position 45 according to the Kabat numbering is an R; and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein.

In particular, according to one preferred, but non-limiting aspect of the invention, a Nanobody can generally be defined as a polypeptide comprising an amino acid sequence that is comprised of four framework regions/sequences interrupted by three complementarity determining regions/sequences, in which;
a-1) the amino acid residue at position 44 according to the Kabat numbering is chosen from the group consisting of A, G, E, D, G, Q, R, S, L; and is preferably chosen from the group consisting of G, E or Q; and
a-2) the amino acid residue at position 45 according to the Kabat numbering is chosen from the group consisting of L, R or C; and is preferably chosen from the group consisting of L or R; and
a-3) the amino acid residue at position 103 according to the Kabat numbering is chosen from the group consisting of W, R or S; and is preferably W or R, and is most preferably W;
a-4) the amino acid residue at position 108 according to the Kabat numbering is Q; or in which:
b-1) the amino acid residue at position 44 according to the Kabat numbering is chosen from the group consisting of E and Q; and b-2) the amino acid residue at position 45 according to the Kabat numbering is R; and
b-3) the amino acid residue at position 103 according to the Kabat numbering is chosen from the group consisting of W, R and S; and is preferably W;
b-4) the amino acid residue at position 108 according to the Kabat numbering is chosen from the group consisting of Q and L; and is preferably Q;
or in which:
c-1) the amino acid residue at position 44 according to the Kabat numbering is chosen from the group consisting of A, G, E, D, Q, R, S and L; and is preferably chosen from the group consisting of G, E and Q; and
c-2) the amino acid residue at position 45 according to the Kabat numbering is chosen from the group consisting of L, R and C; and is preferably chosen from the group consisting of L and R; and
c-3) the amino acid residue at position 103 according to the Kabat numbering is chosen from the group consisting of P, R and S; and is in particular chosen from the group consisting of R and S; and
c-4) the amino acid residue at position 108 according to the Kabat numbering is chosen from the group consisting of Q and L; is preferably Q;
and in which
d) CDR1, CDR2 and CDR3 are as defined herein.

Thus, in another preferred, but non-limiting aspect, a Nanobody may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
a-1) the amino acid residue at position 44 according to the Kabat numbering is chosen from the group consisting of A, G, E, D, G, Q, R, S, L; and is preferably chosen from the group consisting of G, E or Q;
and in which:
a-2) the amino acid residue at position 45 according to the Kabat numbering is chosen from the group consisting of L, R or C; and is preferably chosen from the group consisting of L or R;
and in which:
a-3) the amino acid residue at position 103 according to the Kabat numbering is chosen from the group consisting of W, R or S; and is preferably W or R, and is most preferably W;
and in which
a-4) the amino acid residue at position 108 according to the Kabat numbering is Q; and in which:
d) CDR1, CDR2 and CDR3 are as defined herein.

In another preferred, but non-limiting aspect, a Nanobody may have the structure

FR1-CDR1-FR2-CDR2-FR3-CDR3-FR4 in which FR to FR4 refer to framework regions 1 to 4, respectively, and in which CDR1 to CDR3 refer to the complementarity determining regions 1 to 3, respectively, and in which:
b-1) the amino acid residue at position 44 according to the Kabat numbering is chosen from the group consisting of E and Q;
and in which:
b-2) the amino acid residue at position 45 according to the Kabat numbering is R; and in which:

b-3) the amino acid residue at position 103 according to the Kabat numbering is chosen from the group consisting of W, R and S; and is preferably W;

and in which:

b-4) the amino acid residue at position 108 according to the Kabat numbering is chosen from the group consisting of Q and L; and is preferably Q;

and in which:

d) CDR1, CDR2 and CDR3 are as defined herein.

In another preferred, but non-limiting aspect, a Nanobody may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

c-1) the amino acid residue at position 44 according to the Kabat numbering is chosen from the group consisting of A, G, E, D, Q, R, S and L; and is preferably chosen from the group consisting of G, E and Q;

and in which:

c-2) the amino acid residue at position 45 according to the Kabat numbering is chosen from the group consisting of L, R and C; and is preferably chosen from the group consisting of L and R;

and in which:

c-3) the amino acid residue at position 103 according to the Kabat numbering is chosen from the group consisting of P, R and S; and is in particular chosen from the group consisting of R and S;

and in which:

c-4) the amino acid residue at position 108 according to the Kabat numbering is chosen from the group consisting of Q and L; is preferably Q;

and in which:

d) CDR1, CDR2 and CDR3 are as defined herein.

Two particularly preferred, but non-limiting groups of the Nanobodies are those according to a) above; according to (a-1) to (a-4) above; according to b) above; according to (b-1) to (b-4) above; according to (c) above; and/or according to (c-1) to (c-4) above, in which either:

i) the amino acid residues at positions 44-47 according to the Kabat numbering form the sequence GLEW (SEQ ID NO: 177) (or a GLEW-like sequence as described herein) and the amino acid residue at position 108 is Q;

or in which:

ii) the amino acid residues at positions 43-46 according to the Kabat numbering form the sequence KERE (SEQ ID NO: 178) or KQRE (SEQ ID NO: 179) (or a KERE-like sequence as described) and the amino acid residue at position 108 is Q or L, and is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 44-47 according to the Kabat numbering form the sequence GLEW (SEQ ID NO: 177) (or a GLEW-like sequence as defined herein) and the amino acid residue at position 108 is Q;

and in which:

ii) CDR1, CDR2 and CDR3 are as defined herein.

In another preferred, but non-limiting aspect, a Nanobody may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 43-46 according to the Kabat numbering form the sequence KERE (SEQ ID NO: 178) or KQRE (SEQ ID NO: 179) (or a KERE-like sequence) and the amino acid residue at position 108 is Q or L, and is preferably Q; and in which:

ii) CDR1, CDR2 and CDR3 are as defined herein.

In the Nanobodies in which the amino acid residues at positions 43-46 according to the Kabat numbering form the sequence KERE (SEQ ID NO: 178) or KQRE (SEQ ID NO: 179), the amino acid residue at position 37 is most preferably F. In the Nanobodies of the invention in which the amino acid residues at positions 44-47 according to the Kabat numbering form the sequence GLEW (SEQ ID NO: 177), the amino acid residue at position 37 is chosen from the group consisting of Y, H, I, L, V or F, and is most preferably V.

Thus, without being limited hereto in any way, on the basis of the amino acid residues present on the positions mentioned above, Nanobodies can generally be classified on the basis of the following three groups:

i) The "GLEW-group": Nanobodies with the amino acid sequence GLEW (SEQ ID NO: 177) at positions 44-47 according to the Kabat numbering and Q at position 108 according to the Kabat numbering. As further described herein. Nanobodies within this group usually have a V at position 37, and can have a W, P, R or S at position 103, and preferably have a W at position 103. The GLEW group also comprises some GLEW-like sequences such as those mentioned in Table A-3 below. More generally, and without limitation, Nanobodies belonging to the GLEW-group can be defined as Nanobodies with a G at position 44 and/or with a W at position 47, in which position 46 is usually E and in which preferably position 45 is not a charged amino acid residue and not cysteine:

ii) The "KERE-group": Nanobodies with the amino acid sequence KERE (SEQ ID NO: 178) or KQRE (SEQ ID NO: 179) (or another KERE-like sequence) at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103. More generally, and without limitation, Nanobodies belonging to the KERE-group can be defined as Nanobodies with a K, Q or R at position 44 (usually K) in which position 45 is a charged amino acid residue or cysteine, and position 47 is as further defined herein;

iii) The "103 P, R, S-group": Nanobodies with a P, R or S at position 103. These Nanobodies can have either the amino acid sequence GLEW (SEQ ID NO: 177) at positions 44-47 according to the Kabat numbering or the amino acid sequence KERE (SEQ ID NO: 178) or KQRE (SEQ ID NO: 179) at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Also, where appropriate, Nanobodies may belong to (i.e. have characteristics of) two or more of these classes. For example, one specifically preferred group of Nanobodies has GLEW (SEQ ID NO: 177) or a GLEW-like sequence at positions 44-47; P, R or S (and in particular R) at position 103; and Q at position 108 (which may be humanized to L).

More generally, it should be noted that the definitions referred to above describe and apply to Nanobodies in the form of a native (i.e. non-humanized) $V_{HH}$ sequence, and that humanized variants of these Nanobodies may contain other amino acid residues than those indicated above (i.e. one or more humanizing substitutions as defined herein). For example, and without limitation, in some humanized Nanobodies of the GLEW-group or the 103 P, R, S-group, Q at position 108 may be humanized to 108L As already mentioned herein, other humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ an sequence with the corresponding framework sequence of one or more closely related human $V_H$ sequences, after which one or more of the potentially useful humanizing substitutions (or combinations thereof) thus determined can be introduced into said $V_{HH}$ sequence (i.e. using one of the methods described herein) and the resulting humanized $V_{HH}$ sequences can be tested for affinity for the target, for stability, for ease and level of expression, and/or for one or more of the other desired properties mentioned herein. In this way, the methods described herein will allow the skilled person, by means of a limited degree of trial and error, to determine other suitable humanizing substitutions (or suitable combinations thereof) for a specific Nanobody. Also, based on the foregoing, (the framework regions of) a Nanobody may be partially humanized or fully humanized using the methods described herein.

Thus, in another preferred, but non-limiting aspect, a Nanobody may belong to the GLEW-group (as defined herein).

In another preferred, but non-limiting aspect, a Nanobody of the invention may be a Nanobody belonging to the KERE-group (as defined herein), and CDR1, CDR2 and CDR3 are as defined herein.

Thus, in another preferred, but non-limiting aspect, a Nanobody of the invention may be a Nanobody belonging to the 103 P. R. S-group (as defined herein), and in which CDR1, CDR2 and CDR3 are as defined herein.

Also, more generally and in addition to the 108Q, 43E/44R and 103 P, R, S residues mentioned above, the Nanobodies of the invention can contain, at one or more positions that in a conventional V domain would form (part of) the $V_H/V_L$ interface, one or more amino acid residues that are more highly charged than the amino acid residues that naturally occur at the same position(s) in the corresponding naturally occurring $V_H$ sequence, and in particular one or more charged amino acid residues (as mentioned in Table A-2). Such substitutions include, but are not limited to, the GLEW-like sequences mentioned in Table A-3 below; as well as the substitutions that are described in the International Application WO 00/29004 for so-called "microbodies", e.g. so as to obtain a Nanobody with Q at position 108 in combination with KLEW (SEQ ID NO: 210) at positions 44-47. Other possible substitutions at these positions will be clear to the skilled person based upon the disclosure herein, and/or may be determined by the skilled person using the methods described herein.

In one aspect, the amino acid residue at position 83 of a Nanobody may be chosen from the group consisting of L, M, S, V and W; and is preferably L.

Also, in one aspect, the amino acid residue at position 83 of a Nanobody may be chosen from the group consisting of R, K, N, E, G, I, T and Q; and is most preferably either K or E (for Nanobodies corresponding to naturally occurring $V_{HH}$ domains) or R (for "humanized" Nanobodies, as described herein). The amino acid residue at position 84 is chosen from the group consisting of P, A, R, S, D T, and V in one aspect, and is most preferably P (for Nanobodies corresponding to naturally occurring $V_{HH}$ domains) or R (for "humanized" Nanobodies, as described herein).

Furthermore, in one aspect, the amino acid residue at position 104 of a Nanobody may be chosen from the group consisting of G and D; and is most preferably G.

It will also be clear to the skilled person that the specific substitutions mentioned herein (and in particular the humanizing substitutions mentioned herein) may also be used/introduced as "specific mutations" in the methods described herein.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human $V_{11}$ domain, $V_{11}3$, are summarized in Table A-3.

Some especially preferred but non-limiting combinations of these Hallmark Residues as occur in naturally occurring $V_{HH}$ domains are mentioned in Table A-4. For comparison, the corresponding amino acid residues of the human $V_H3$ called DP-47 have been indicated in italics.

From the Tables A-3 to A-8 below, some suitable (but non-limiting) humanizing substitution (or combinations of humanizing substitutions) or camelizing substitutions (or combination of camelizing substitutions) that may be introduced and tested as specific mutations using the methods described herein will also become clear to the skilled person.

Some other substitutions that may be may be introduced and tested as specific mutations using the methods described herein (optionally in combination with one or more humanizing substitutions and/or with one or more specific mutations that are meant to improve the affinity) for example include one or more conservative substitutions (as described herein) and/or substitutions in which an amino acid residue is replaced by another amino acid residue that naturally occurs at the same position in another $V_{HH}$ domain (see Tables A-5 to A-8 for some non-limiting examples of such substitutions). More generally, any one or more substitutions, deletions or insertions, or any combination thereof, that is meant to improve the properties of the Nanobody or the balance or combination of desired properties of the Nanobody can be introduced and tested using the methods described herein, and based on the disclosure herein, the skilled person will generally be able to select such specific mutations and to design oligonucleotides to be used in step a) that will afford, upon PCR assembly and optionally expression, a sequence or analog that contains the desired specific mutation(s).

As can also be seen from the data on the $V_{HH}$ entropy and $V_{HH}$ variability given in Tables A-5 to A-8 above, some amino acid residues in the framework regions are more conserved than others. Generally, although the invention in its broadest sense is not limited thereto, the methods of the invention are preferably used to introduce specific mutations at positions that are less conserved. Also, generally, amino acid substitutions are preferred over amino acid deletions or insertions.

TABLE A-3

Hallmark Residues in Nanobodies

| Position | Human $V_H3$ | Hallmark Residues |
|---|---|---|
| 11 | L, V; predominantly L | L, M, S, V, W; preferably L |
| 37 | V, I, F; usually V | $F^{(1)}$, Y, H, I, L or V, preferably $F^{(1)}$ or Y |
| $44^{(8)}$ | G | $G^{(2)}$, $E^{(3)}$, A, D, Q, R, S, L; preferably $G^{(2)}$, $E^{(3)}$ or Q; most preferably $G^{(2)}$ or $E^{(3)}$. |
| $45^{(8)}$ | L | $L^{(2)}$, $R^{(3)}$, C, I, L, P, Q, V; preferably $L^{(2)}$ or $R^{(3)}$ |
| $47^{(8)}$ | W, Y | $W^{(2)}$, $L^{(1)}$ or $F^{(1)}$, A, G, I, M, R, S, V or Y; preferably $W^{(2)}$, $L^{(1)}$, $F^{(1)}$ or R |
| 83 | R or K; usually R | R, $K^{(5)}$, N, $E^{(5)}$, G, I, M, Q or T; preferably K or R; most preferably K |
| 84 | A, T, D; predominantly A | $P^{(5)}$, A, L, R, S, T, D, V; preferably P |
| 103 | W | $W^{(4)}$, $P^{(6)}$, $R^{(6)}$, S; preferably W |
| 104 | G | G or D; preferably G |
| 108 | L, M or T; predominantly L | Q, $L^{(7)}$ or R; preferably Q or $L^{(7)}$ |

Notes:
$^{(1)}$In particular, but not exclusively, in combination with KERE (SEQ ID NO: 178) or KQRE (SEQ ID NO: 179) at positions 43-46.
$^{(2)}$Usually as GLEW (SEQ ID NO: 177) at positions 44-47.
$^{(3)}$Usually as KERE (SEQ ID NO: 178) or KQRE (SEQ ID NO: 179) at positions 43-46, e.g. as KEREL (SEQ ID NO: 180), KEREF (SEQ ID NO: 181), KQREL (SEQ ID NO: 182), KQREF (SEQ ID NO: 183) or KEREG (SEQ ID NO: 184) at positions 43-47. Alternatively, also sequences such as TERE (SEQ ID NO: 185) (for example TEREL (SEQ ID NO: 186)), KECE (SEQ ID NO: 187) (for example KECEL (SEQ ID NO: 188) or KECER (SEQ ID NO: 189)), RERE (SEQ ID NO: 190) (for example REREG (SEQ ID NO: 191)), QERE (SEQ ID NO: 192) (for example QEREG (SEQ ID NO: 193)), KGRE (SEQ ID NO: 194) (for example KGREG (SEQ ID NO: 195)), KDRE (SEQ ID NO: 196) (for example KDREV (SEQ ID NO: 197)) are possible. Some other possible, but less preferred sequences include for example DECKL (SEQ ID NO: 198) and NVCEL (SEQ ID NO: 199).
$^{(4)}$With both GLEW (SEQ ID NO: 177) at positions 44-47 and KERE (SEQ ID NO: 178) or KQRE (SEQ ID NO: 179) at positions 43-46.
$^{(5)}$Often as KP or EP at positions 83-84 of naturally occurring $V_{HH}$ domains.
$^{(6)}$In particular, but not exclusively, in combination with GLEW (SEQ ID NO: 177) at positions 44-47.
$^{(7)}$With the proviso that when positions 44-47 are GLEW (SEQ ID NO: 177), position 108 is always Q in (non-humanized) $V_{HH}$ sequences that also contain a W at position 103.
$^{(8)}$The GLEW group also contains GLEW-like sequences at positions 44-47, such as for example GVEW (SEQ ID NO: 200), EPEW (SEQ ID NO: 201), GLER (SEQ ID NO: 202), DQEW (SEQ ID NO: 203), DLEW (SEQ ID NO: 204), GIEW (SEQ ID NO: 205), ELEW (SEQ ID NO: 206), GPEW (SEQ ID NO: 207), EWLP (SEQ ID NO: 208), and GPER (SEQ ID NO: 209).

TABLE A-4

Some preferred but non-limiting combinations of Hallmark Residues in naturally occurring Nanobodies. For humanization of these combinations, reference is made to the specification.

| | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
| | L | F | E | R | F | E | P | W | G | Q |
| | L | F | E | R | F | K | P | W | G | Q |
| | L | Y | Q | R | L | K | P | W | G | Q |
| | L | F | L | R | V | K | P | Q | G | Q |
| | L | F | Q | R | L | K | P | W | G | Q |
| | L | F | E | R | F | K | P | W | G | Q |
| "GLEW" group | L | V | G | L | W | K | S | W | G | Q |
| | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables A-5 to A-8 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering by Chothia (supra) that the residues at these positions already form part of CDR1.)

In Tables A-5-A-8, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

For reference only, Tables A-5-A-8 also contain data on the $V_{HH}$ entropy ("$V_{HH}$ Ent.") and $V_{HH}$ variability ("$V_{HH}$ Var.") at each amino acid position for a representative sample of 1118 $V_{HH}$ sequences (data kindly provided by David Lutje Hulsing and Prof. Theo Verrips of Utrecht University). The values for the $V_{HH}$ entropy and the $V_{HH}$ variability provide a measure for the variability and degree of conservation of amino acid residues between the 1118 $V_{HH}$ sequences analyzed: low values (i.e. <1, such as <0.5) indicate that an amino acid residue is highly conserved between the $V_{HH}$ sequences (i.e. little variability). For example, the G at position 8 and the G at position 9 have values for the $V_{HH}$ entropy of 0.1 and 0 respectively, indicating that these residues are highly conserved and have little variability (and in case of position 9 is G in all 1118 sequences analysed), whereas for residues that form part of the CDR's generally values of 1.5 or more are found (data not shown). Note that (1) the amino acid residues listed in the second column of Tables A-5-A-8 are based on a bigger sample than the 1118 $V_{HH}$ sequences that were analysed for determining the $V_{HH}$ entropy and $V_{HH}$ variability referred to in the last two columns; and (2) the data represented below support the hypothesis that the amino acid residues at positions 27-30 and maybe even also at positions 93 and 94 already form part of the CDR's (although the invention is not limited to any specific hypothesis or explanation, and as mentioned above, herein the numbering according to Kabat is used). For a general explanation of sequence entropy, sequence variability and the methodology for determining the same, see Oliveira et al., PROTEINS: Structure, Function and Genetics, 52: 544-552 (2003).

TABLE A-5

Non-limiting examples of amino acid residues in FR1 (for the footnotes, see the footnotes to Table A-3)

| | Amino acid residue(s): | | $V_{HH}$ | $V_{HH}$ |
|---|---|---|---|---|
| Pos. | Human $V_H3$ | Camelid $V_{HH}$'s | Ent. | Var. |
| 1 | E, Q | Q, A, E | — | — |
| 2 | V | V | 0.2 | 1 |
| 3 | Q | Q, K | 0.3 | 2 |
| 4 | L | L | 0.1 | 1 |

TABLE A-5-continued

Non-limiting examples of amino acid residues in FR1 (for the footnotes, see the footnotes to Table A-3)

| Pos. | Human V$_H$3 | Camelid V$_{HH}$'S | Amino acid residue(s): V$_{HH}$ Ent. | V$_{HH}$ Var. |
|---|---|---|---|---|
| 5 | V, L | Q, E, L, V | 0.8 | 3 |
| 6 | E | E, D, Q, A | 0.8 | 4 |
| 7 | S, T | S, F | 0.3 | 2 |
| 8 | G, R | G | 0.1 | 1 |
| 9 | G | G | 0 | 1 |
| 10 | G, V | G, D, R | 0.3 | 2 |
| 11 | | Hallmark residue: L, M, S, V, W; preferably L | 0.8 | 2 |
| 12 | V, I | V, A | 0.2 | 2 |
| 13 | Q, K, R | Q, E, K, P, R | 0.4 | 4 |
| 14 | P | A, Q, A, G, P, S, T, V | 1 | 5 |
| 15 | G | G | 0 | 1 |
| 16 | G, R | G, A, E, D | 0.4 | 3 |
| 17 | S | S, F | 0.5 | 2 |
| 18 | L | L, V | 0.1 | 1 |
| 19 | R, K | R, K, L, N, S, T | 0.6 | 4 |
| 20 | L | L, F, I, V | 0.5 | 4 |
| 21 | S | S, A, F, T | 0.2 | 3 |
| 22 | C | C | 0 | 1 |
| 23 | A, T | A, D, E, P, S, T, V | 1.3 | 5 |
| 24 | A | A, I, L, S, T, V | 1 | 6 |
| 25 | S | S, A, F, P, T | 0.5 | 5 |
| 26 | G | G, A, D, E, R, S, T, V | 0.7 | 7 |
| 27 | F | S, F, R, L, P, G, N, | 2.3 | 13 |
| 28 | T | N, T, E, D, S, I, R, A, G, R, F, Y | 1.7 | 11 |
| 29 | F, V | F, L, D, S, I, G, V, A | 1.9 | 11 |
| 30 | S, D, G | N, S, E, G, A, D, M, T | 1.8 | 11 |

TABLE A-6

Non-limiting examples of amino acid residues in FR2 (for the footnotes, see the footnotes to Table A-3)

| Pos. | Human V$_H$3 | Camelid V$_{HH}$'s | Amino acid residue(s): V$_{HH}$ Ent. | V$_{HH}$ Var. |
|---|---|---|---|---|
| 36 | W | W | 0.1 | 1 |
| 37 | | Hallmark residue: F$^{(1)}$, H, I, L, Y or V, preferably F$^{(1)}$ or Y | 1.1 | 6 |
| 38 | R | R | 0.2 | 1 |
| 39 | Q | Q, H, P, R | 0.3 | 2 |
| 40 | A | A, F, G, L, P, T, V | 0.9 | 7 |
| 41 | P, S, T | P, A, L, S | 0.4 | 3 |
| 42 | G | G, E | 0.2 | 2 |
| 43 | K | K, D, E, N, Q, R, T, V | 0.7 | 6 |
| 44 | | Hallmark residue: G$^{(2)}$, E$^{(3)}$, A, D, Q, R, S, L; preferably G$^{(2)}$, E$^{(3)}$ or Q; most preferably G$^{(2)}$ or E$^{(3)}$ | 1.3 | 5 |
| 45 | | Hallmark residue: L$^{(2)}$, R$^{(3)}$, C, I, L, P, Q, V; preferably L$^{(2)}$ or R$^{(3)}$ | 0.6 | 4 |
| 46 | E, V | E, D, K, Q, V | 0.4 | 2 |
| 47 | | Hallmark residue: W$^{(2)}$, L$^{(1)}$ or F$^{(1)}$, A, G, I, M, R, S, V or Y; preferably W$^{(2)}$, L$^{(1)}$, F$^{(1)}$ or R | 1.9 | 9 |
| 48 | V | V, I, L | 0.4 | 3 |
| 49 | S, A, G | A, S, G, T, V | 0.8 | 3 |

TABLE A-7

Non-limiting examples of amino acid residues in FR3 (for the footnotes, see the footnotes to Table A-3)

| Pos. | Human V$_H$3 | Camelid V$_{HH}$'s | Amino acid residue(s): V$_{HH}$ Ent. | V$_{HH}$ Var. |
|---|---|---|---|---|
| 66 | R | R | 0.1 | 1 |
| 67 | F | F, L, V | 0.1 | 1 |
| 68 | T | T, A, N, S | 0.5 | 4 |
| 69 | I | I, L, M, V | 0.4 | 4 |
| 70 | S | S, A, F, T | 0.3 | 4 |
| 71 | R | R, G, H, I, L, K, Q, S, T, W | 1.2 | 8 |
| 72 | D, E | D, E, G, N, V | 0.5 | 4 |
| 73 | N, D, G | N, A, D, F, I, K, L, R, S, T, V, Y | 1.2 | 9 |
| 74 | A, S | A, D, G, N, P, S, T, V | 1 | 7 |
| 75 | K | K, A, E, K, L, N, Q, R | 0.9 | 6 |
| 76 | N, S | N, D, K, R, S, Y | 0.9 | 6 |
| 77 | S, T, I | T, A, E, I, M, P, S | 0.8 | 5 |

TABLE A-7-continued

Non-limiting examples of amino acid residues in FR3 (for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 78 | L, A | V, L, A, F, G, I, M | 1.2 | 5 |
| 79 | Y, H | Y, A, D, F, H, N, S, T | 1 | 7 |
| 80 | L | L, F, V | 0.1 | 1 |
| 81 | Q | Q, E, I, L, R, T | 0.6 | 5 |
| 82 | M | M, I, L, V | 0.2 | 2 |
| 82a | N, G | N, D, G, H, S, T | 0.8 | 4 |
| 82b | S | S, N, D, G, R, T | 1 | 6 |
| 82c | L | L, P, V | 0.1 | 2 |
| 83 | | Hallmark residue: R, K$^{(5)}$, N, E$^{(5)}$, G, I, M, Q or T; preferably K or R; most preferably K | 0.9 | 7 |
| 84 | | Hallmark residue: P$^{(5)}$, A, D, L, R, S, T, V; preferably P | 0.7 | 6 |
| 85 | E, G | E, D, G, Q | 0.5 | 3 |
| 86 | D | D | 0 | 1 |
| 87 | T, M | T, A, S | 0.2 | 3 |
| 88 | A | A, G, S | 0.3 | 2 |
| 89 | V, L | V, A, D, I, L, M, N, R, T | 1.4 | 6 |
| 90 | Y | Y, F | 0 | 1 |
| 91 | Y, H | Y, D, F, H, L, S, T, V | 0.6 | 4 |
| 92 | C | C | 0 | 1 |
| 93 | A, K, T | A, N, G, H, K, N, R, S, T, V, Y | 1.4 | 10 |
| 94 | K, R, T | A, V, C, F, G, I, K, L, R, S or T | 1.6 | 9 |

TABLE A-8

Non-limiting examples of amino acid residues in FR4 (for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 103 | | Hallmark residue: W$^{(4)}$, P$^{(6)}$, R$^{(6)}$, S; preferably W | 0.4 | 2 |
| 104 | | Hallmark residue: G or D; preferably G | 0.1 | 1 |
| 105 | Q, R | Q, E, K, P, R | 0.6 | 4 |
| 106 | G | G | 0.1 | 1 |
| 107 | T | T, A, I | 0.3 | 2 |
| 108 | | Hallmark residue: Q, L$^{(7)}$ or R; preferably Q or L$^{(7)}$ | 0.4 | 3 |
| 109 | V | V | 0.1 | 1 |
| 110 | T | T, I, A | 0.2 | 1 |
| 111 | V | V, A, I | 0.3 | 2 |
| 112 | S | S, F | 0.3 | 1 |
| 113 | S | S, A, L, P, T | 0.4 | 3 |

Thus, in another preferred, but not limiting aspect, a Nanobody of the invention can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) one or more of the amino acid residues at positions 11, 37, 44, 45, 47, 83, 84, 103, 104 and 108 according to the Kabat numbering are chosen from the Hallmark residues mentioned in Table A-3;

and in which:

ii) CDR1, CDR2 and CDR3 are as defined herein.

Even more in particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR to CDR3 refer to the complementarity determining regions 1 to 3, respectively, and in which:

i) preferably one or more of the amino acid residues at positions 11, 37, 44, 45, 47, 83, 84, 103, 104 and 108 according to the Kabat numbering am chosen from the Hallmark residues mentioned in Table A-3 below;

and in which:

ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded;

and in which:

iii) CDR1, CDR2 and CDR3 are as defined herein.

TABLE A-9

Representative amino acid sequences for Nanobodies of the KERE, GLEW and P, R, S 103 group.

| | | |
|---|---|---|
| KERE sequence no. 1 | SEQ ID NO: 1 | EVQLVESGGGLVQPGGSLRLSCAASGIPFSXXXXXXWFRQAPGKQRDSVAXXXXXXRFTISRDNAKNTVYLQMNSLKPEDTAVYRCYFXXXXXXWGQGTQVTVSS |
| KERE sequence no. 2 | SEQ ID NO: 2 | QVKLEESGGGLVQAGGSLRLSCVGSGRTFSXXXXXXWFRLAPGKEREFVAXXXXXXRFTISRDTASNRGYLHMNNLTPEDTAVYYCAAXXXXXXWGQGTQVTVSS |
| KERE sequence no. 3 | SEQ ID NO: 3 | AVQLVDSGGGLVQAGDSLKLSCALTGGAFTXXXXXXWFRQTPGREREFVAXXXXXXRFTISRDNAKNMVYLRMNSLIPEDAAVYSCAAXXXXXXWGQGTLVTVSS |
| KERE sequence no. 4 | SEQ ID NO: 4 | QVQLVESGGGLVEAGGSLRLSCTASESPFRXXXXXXWFRQTSGQEREFVAXXXXXXRFTISRDDAKNTVWLHGSTLKPEDTAVYYCAAXXXXXXWGQGTQVTVSS |
| KERE sequence no. 5 | SEQ ID NO: 5 | AVQLVESGGGLVQGGGSLRLACAASERIFDXXXXXXWYRQGPGNERELVAXXXXXXRFTISMDYTKQTVYLHMNSLRPEDTGLYYCKIXXXXXXWGQGTQVTVSS |
| KERE sequence no. 6 | SEQ ID NO: 6 | DVKFVESGGGLVQAGGSLRLSCVASGFNFDXXXXXXWFRQAPGKEREEVAXXXXXXRFTISSEKDKNSVYLQMNSLKPEDTALYICAGXXXXXWGRGTQVTVSS |
| KERE sequence no. 7 | SEQ ID NO: 7 | QVRLAESGGGLVQSGGSLRLSCVASGSTYTXXXXXXWYRQYPGKQRALVAXXXXXXRFTIARDSTKDTFCLQMNNLKPEDTAVYYCYAXXXXXXWGQGTQVTVSS |
| KERE sequence no. 8 | SEQ ID NO: 8 | EVQLVESGGGLVQAGGSLRLSCAASGFTSDXXXXXXWFRQAPGKPREGVSXXXXXXRFTISTDNAKNTVHLLMNRVNAEDTALYYCAVXXXXXXWGRGTRVTVSS |
| KERE sequence no. 9 | SEQ ID NO: 9 | QVQLVESGGGLVQPGGSLRLSCQASGDISTXXXXXXWYRQVPGKLREFVAXXXXXXRFTISGDNAKRAIYLQMNNLKPDDTAVYYCNRXXXXXXWGQGTQVTVSP |
| KERE sequence no. 10 | SEQ ID NO: 10 | QVPVVESGGGLVQAGDSLRLFCAVPSFTSTXXXXXXWFRQAPGKEREFVAXXXXXXRFTISRNATKNTLTLRMDSLKPEDTAVYYCAAXXXXXXWGQGTQVTVSS |
| KERE sequence no. 11 | SEQ ID NO: 11 | EVQLVESGGGLVQAGDSLRLFCTVSGGTASXXXXXXWFRQAPGEKREFVAXXXXXXRFTIARENAGNMVYLQMNNLKPDDTALYTCAAXXXXXXWGRGTQVTVSS |
| KERE sequence no. 12 | SEQ ID NO: 12 | AVQLVESGGDSVQPGDSQTLSCAASGRTNSXXXXXXWFRQAPGKERVFLAXXXXXXRFTISRDSAKNMMYLQMNNLKPQDTAVYYCAAXXXXXXWGQGTQVTVSS |
| KERE sequence no. 13 | SEQ ID NO: 13 | AVQLVESGGGLVQAGGSLRLSCVVSGLTSSXXXXXXWFRQTPWQERDFVAXXXXXXRFTISRDNYKDTVLLEMNFLKPEDTAIYYCAAXXXXXXWGQGTQVTVSS |
| KERE sequence no. 14 | SEQ ID NO: 14 | AVQLVESGGGLVQAGASLRLSCATSTRTLDXXXXXXWFRQAPGRDREFVAXXXXXXRFTVSRDSAENTVALQMNSLKPEDTAVYYCAAXXXXXXWGQGTRVTVSS |
| KERE sequence no. 15 | SEQ ID NO: 15 | QVQLVESGGGLVQPGGSLRLSCTVSRLTAHXXXXXXWFRQAPGKEREAVSXXXXXXRFTISRDYAGNTAFLQMDSLKPEDTGVYYCATXXXXXXWGQGTQVTVSS |
| KERE sequence no. 16 | SEQ ID NO: 16 | EVQLVESGGELVQAGGSLKLSCTASGRNFVXXXXXXWFRRAPGKEREFVAXXXXXXRFTVSRDNGKNTAYLRMNSLKPEDTADYYCAVXXXXXXLGSGTQVTVSS |
| GLEW sequence no. 1 | SEQ ID NO: 17 | AVQLVESGGGLVQPGGSLRLSCAASGFTFSXXXXXXWVRQAPGKVLEWVSXXXXXXRFTISRDNAKNTLYLQMNSLKPEDTAVYYCVKXXXXXXGSQGTQVTVSS |
| GLEW sequence no. 2 | SEQ ID NO: 18 | EVQLVESGGGLVQPGGSLRLSCVCVSSGCTXXXXXXWVRQAPGKAEEWVSXXXXXXRFKISRDNAKKTLYLQMNSLGPEDTAMYYCQRXXXXXXRGQGTQVTVSS |
| GLEW sequence no. 3 | SEQ ID NO: 19 | EVQLVESGGGLALPGGSLTLSCVFSGSTFSXXXXXXWVRHTPGKAEEWVSXXXXXXRFTISRDNAKNTLYLEMNSLSPEDTAMYYCGRXXXXXXRSKGIQVTVSS |
| P, R, S 103 sequence no. 1 | SEQ ID NO: 20 | AVQLVESGGGLVQAGGSLRLSCAASGRTFSXXXXXXWFRQAPGKEREFVAXXXXXXRFTISRDNAKNTVYLQMNSLKPEDTAVYYCAAXXXXXXRGQGTQVTVSS |
| P, R, S 103 sequence no. 2 | SEQ ID NO: 21 | DVQLVESGGDLVQPGGSLRLSCAASGFSFDXXXXXXWLRQTPGKGLEWVGXXXXXXRFTISRDNAKNMLYLHLNNLKSEDTAVYYCRRXXXXXXLGQGTQVTVSS |
| P, R, S 103 sequence no. 3 | SEQ ID NO: 22 | EVQLVESGGGLVQPGGSLRLSCVCVSSGCTXXXXXXWVRQAPGKAEEWVSXXXXXXRFKISRDNAKKTLYLQMNSLGPEDTAMYYCQRXXXXXXRGQGTQVTVSS |

The CDR's are indicated with XXXX

As will also be clear from the disclosure herein that the methods of the invention may also be used to provide parts to fragments of a $V_{HH}$ sequence or Nanobody (or of another amino acid sequence as described herein), and that such fragments may also be suitably combined to form sequences that comprise a combination of two or more such parts or fragments. Also, when the methods of the invention have been used to provide a $V_{HH}$ sequence or Nanobody (or another amino acid sequence as described herein), the invention also comprises suitable parts or fragments thereof. Generally, such parts or fragments may have amino acid sequences in which, compared to the corresponding full length sequence, one or more of the amino acid residues at the N-terminal end, one or more amino acid residues at the C-terminal end, one or more contiguous internal amino acid residues, or any combination thereof, have been deleted and/or removed. For example, such parts or fragments may be as described in WO 06/122825 for the parts or fragments of the Nanobodies described therein.

The invention in its broadest sense also comprises derivatives of the amino acid sequences obtained using the methods described herein. Such derivatives may for example be as described in WO 06/122825 (i.e. for the derivatives of the Nanobodies described therein).

The proteins or polypeptides that comprise at least one Nanobody (or other amino acid sequence) that has been generated using the methods described herein may generally comprise such a Nanobody (or other amino acid sequence), which is fused at its amino terminal end, at its carboxy terminal end, or both at its amino terminal end and at its carboxy terminal end to at least one further amino acid sequence, i.e. so as to provide a fusion protein comprising said Nanobody (or other amino acid sequence) and the one or more further amino acid sequences.

The one or more further amino acid sequence may be any suitable and/or desired amino acid sequences. The further amino acid sequences may or may not change, alter or otherwise influence the (biological) properties of the Nanobody obtained using the methods described herein, and may or may not add further functionality to the Nanobody or the polypeptide of the invention. Preferably, the further amino acid sequence is such that it confers one or more desired properties or functionalities to the Nanobody or the polypeptide of the invention.

For example, the further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the Nanobody of the invention is directed, or a different protein, polypeptide, antigen, antigenic determinant or epitope).

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the Nanobody of the invention per se. Some non-limiting examples of such amino acid sequences are those described in WO 06/122825 (i.e. for polypeptides containing one or more of the Nanobodies described therein), and include other amino acid sequences or Nanobodies that can bind to serum proteins such as serum albumin. Reference is for example also made to WO 91/01743, WO 01/45746, WO 02/076489. WO 03/002609, WO 04/003019, EP 0 368 684, as well as to the U.S. provisional applications 60/843,349, 60/850,774, 60/850,775 by Ablynx N.V. mentioned herein and US provisional application of Ablynx N.V. entitled "Peptides capable of binding to serum proteins" filed on Dec. 5, 2006 (also mentioned herein).

According to another aspect, the one or more further amino acid sequences may comprise one or more parts, fragments or domains of conventional 4-chain antibodies (and in particular human antibodies) and/or of heavy chain antibodies. Reference is again made to the disclosure in WO 06/1228 and the further applications by Ablynx N.V. mentioned herein.

According to one specific aspect of a polypeptide of the invention, one or more Nanobodies of the invention may be linked to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG, from IgE or from another human Ig. For example, WO 94/04678 describes heavy chain antibodies comprising a Camelid $V_{HH}$ domain or a humanized derivative thereof (i.e. a Nanobody), in which the Camelidae $C_{H2}$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the Nanobodies of the invention so as to provide an effector function will be clear to the skilled person, and may be chosen on the basis of the desired effector function(s). Reference is for example made to WO 04/058820, WO 99/42077 and WO 05/017148, as well as the review by Holliger and Hudson, supra. Coupling of a Nanobody of the invention to an Fc portion may also lead to an increased half-life, compared to the corresponding Nanoboxxy of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more Nanobodies and one or more constant domains with increased half-life in vivo will be clear to the skilled person, and may for example comprise two Nanobodies linked to a $C_H3$ domain, optionally via a linker sequence. Generally, any fusion protein or derivatives with increased half-life will preferably have a molecular weight of more than 50 kD, the cut-off value for renal absorption.

The further amino acid sequences may also form a signal sequence or leader sequence that directs secretion of the Nanobody or the polypeptide of the invention from a host cell upon synthesis (for example to provide a pre-, pro- or prepro-form of the polypeptide of the invention, depending on the host cell used to express the polypeptide of the invention). Reference is again made to the general disclosure in WO 06/122825 and the further applications by Ablynx N.V. mentioned herein.

The further amino acid sequence may also form a sequence or signal that allows the Nanobody or polypeptide of the invention to be directed towards and/or to penetrate or enter into specific organs, tissues, cells, or parts or compartments of cells, and/or that allows the Nanobody or polypeptide of the invention to penetrate or cross a biological barrier such as a cell membrane, a cell layer such as a layer of epithelial cells, a tumor including solid tumors, or the blood-brain-barrier. Reference is again made to the disclosure in WO 06/1228 and the further applications by Ablynx N.V. mentioned herein.

For some applications, in particular for those applications in which it is intended to kill a cell that expresses the target against which the Nanobodies of the invention are directed (e.g. in the treatment of cancer), or to reduce or slow the growth and/or proliferation of such a cell, the Nanobodies of the invention may also be linked to a (cyto)toxic protein or polypeptide. Examples of such toxic proteins and polypeptides which can be linked to a Nanobody of the invention to provide—for example—a cytotoxic polypeptide of the invention will be clear to the skilled person and can for example be found in the prior art cited above and/or in the further description herein. One example is the so-called ADEPT™ technology described in WO 03/055527.

According to one preferred, but non-limiting aspect, said one or more further amino acid sequences comprise at least one further Nanobody, so as to provide a polypeptide of the invention that comprises at least two, such as three, four, five or more Nanobodies, in which said Nanobodies may optionally be linked via one or more linker sequences (as defined herein). Polypeptides of the invention that comprise two or more Nanobodies, of which at least one is a Nanobody of the invention, will also be referred to herein as "multivalent" polypeptides of the invention, and the Nanobodies present in such polypeptides will also be referred to herein as being in a "multivalent format". For example a "bivalent" polypeptide of the invention comprises two Nanobodies, optionally linked via a linker sequence, whereas a "trivalent" polypeptide of the invention comprises three Nanobodies, optionally linked via two linker sequences; etc.; in which at least one of the Nanobodies present in the polypeptide, and up to all of the Nanobodies present in the polypeptide, is/are a Nanobody of the invention.

In a multivalent polypeptide of the invention, the two or more Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical Nanobodies; (b) a first Nanobody directed against a first antigenic determinant of a protein or antigen and a second Nanobody directed against the same antigenic determinant of said protein or antigen which is different from the first Nanobody; (c) a first Nanobody directed against a first antigenic determinant of a protein or antigen and a second Nanobody directed against another antigenic determinant of said protein or antigen; or (d) a first Nanobody directed against a first protein or antigen and a second Nanobody directed against a second protein or antigen (i.e. different from said first antigen). Similarly, a trivalent polypeptide of the invention may, for example and without being limited thereto, comprise (a) three identical Nanobodies; (b) two identical Nanobody against a first antigenic determinant of an antigen and a third Nanobody directed against a different antigenic determinant of the same antigen; (c) two identical Nanobody against a first antigenic determinant of an antigen and a third Nanobody directed against a second antigen different from said first antigen; (d) a first Nanobody directed against a first antigenic determinant of a first antigen, a second Nanobody directed against a second antigenic determinant of said first antigen and a third Nanobody directed against a second antigen different from said first antigen; or (e) a first Nanobody directed against a first antigen, a second Nanobody directed against a second antigen different from said first antigen, and a third Nanobody directed against a third antigen different from said first and second antigen. Reference is again made to the disclosure in WO 06/122825 and the further applications by Ablynx N.V. mentioned herein.

Polypeptides of the invention that contain at least two Nanobodies, in which at least one Nanobody is directed against a first antigen, and at least one Nanobody is directed against a second antigen, will also be referred to as "multispecific" polypeptides of the invention, and the Nanobodies present in such polypeptides will also be referred to herein as being in a "multispecific format".

For a general description of multivalent and multispecific constructs, reference is again made to the disclosure in WO 06/1228 and the further applications by Ablynx N.V. mentioned herein, as well as to Conrath et al., J. Biol. Chem., Vol. 276, 10, 7346-7350, 2001; Muyldermans, Reviews in Molecular Biotechnology 74 (2001), 277-302; as well as to for example WO 96/34103 and WO 99/23221. As mentioned above, one preferred, but non-limiting example of a multispecific polypeptide of the invention comprises at least one Nanobody of the invention and at least one Nanobody that provides for an increased half-life. Reference is again made to the general disclosure in WO 06/1228 and the further applications by Ablynx N.V. mentioned herein.

Another preferred, but non-limiting example of a multispecific polypeptide of the invention comprises at least one Nanobody of the invention and at least one Nanobody that directs the polypeptide of the invention towards, and/or that allows the polypeptide of the invention to penetrate or to enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Reference is again made to the general disclosure in WO 06/1228 and the further applications by Ablynx N.V. mentioned herein In the polypeptides of the invention, the one or more Nanobodies and the one or more polypeptides may be directly linked to each other (as for example described in WO 99/23221) and/or may be linked to each other via one or more suitable spacers or linkers, or any combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Reference is again made to the general disclosure in WO 06/1228 and the further applications by Ablynx N.V. mentioned herein The invention also comprises proteins or polypeptides that "essentially consist" of a polypeptide of the invention (in which the wording "essentially consist of" has essentially the same meaning as indicated hereinabove).

According to one aspect of the invention, the polypeptide of the invention is in essentially isolated from, as defined herein.

The amino acid sequences, Nanobodies, polypeptides and nucleic acids of the invention can be prepared in a manner known per se, as will be clear to the skilled person from the further description herein. For example, the Nanobodies and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, polypeptides and nucleic acids include the methods and techniques described herein.

As will be clear to the skilled person, one particularly useful method for preparing an amino acid sequence, Nanobody and/or a polypeptide of the invention generally comprises the steps of:

i) the expression, in a suitable host cell or host organism (also referred to herein as a "host of the invention") or in another suitable expression system of a nucleic acid that encodes said amino acid sequence, Nanobody or polypeptide of the invention (also referred to herein as a "nucleic acid of the invention"), optionally followed by:

ii) isolating and/or purifying the amino acid sequence, Nanobody or polypeptide of the invention thus obtained.

In particular, such a method may comprise the steps of:

i) cultivating and/or maintaining a host of the invention under conditions that are such that said host of the invention expresses and/or produces at least one amino acid sequence, Nanobody and/or polypeptide of the invention; optionally followed by:

ii) isolating and/or purifying the amino acid sequence, Nanobody or polypeptide of the invention thus obtained.

For a further description of methods, techniques, host cells, expression systems, purification techniques, etc. for preparing and expressing Nanobodies, reference is again made to the disclosure in WO 06/122825 and the further applications by Ablynx N.V. mentioned herein.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form. The nucleic acid of the invention may also be in the form of a genetic construct, which may for example contain one or more suitable regulatory elements. Reference is again made to the disclosure in WO 06/122825 and the further applications by Ablynx N.V. mentioned herein.

The nucleic acids of the invention can be prepared using the methods described herein, or may alternatively be obtained in a manner known per se, starting from a sequence and/or based on sequence information obtained using the methods described herein. For such methods and techniques, reference is again made to the disclosure in WO 06/122825 and the further applications by Ablynx N.V. mentioned herein.

The invention also relates to uses of the amino acid sequences and polypeptides described herein. Such uses may for example depend upon the antigen(s) against which the amino acid sequences and polypeptides are directed. For example, amino acid sequences and polypeptides that are directed against a therapeutically relevant target or antigen may be used for therapeutic purposes, i.e. for the prevention and/or treatment of a disease or disorder of a subject in need thereof.

The invention also relates to compositions that comprise at least one amino acid sequence or polypeptide as described herein, and optionally one or more further components of such compositions known per se. For therapeutic use, such a composition may be a pharmaceutical formulation or preparation, comprising at least one amino acid sequence or polypeptide as described herein that is directed against a therapeutically relevant target or antigen, and optionally at least one pharmaceutically acceptable carrier, diluent or excipient and/or adjuvant, and optionally one or more further pharmaceutically active polypeptides and/or compounds. Reference is again made to the general disclosure in WO 06/1228 and the further applications by Ablynx N.V. mentioned herein.

The invention will now be further described by means of the following non-limiting examples and figures, in which:

FIGS. 1-A to 1-C schematically illustrate the methods described herein.

FIG. 2 gives the sequences of a set of 26 overlapping oligonucleotides (SEQ ID NO's: 23 to 48) used to assemble a collection of 71 humanized variants (SEQ ID NO's: 50 to 212) of the Nanobody 32C9 (SEQ ID No: 49).

Figure 3:
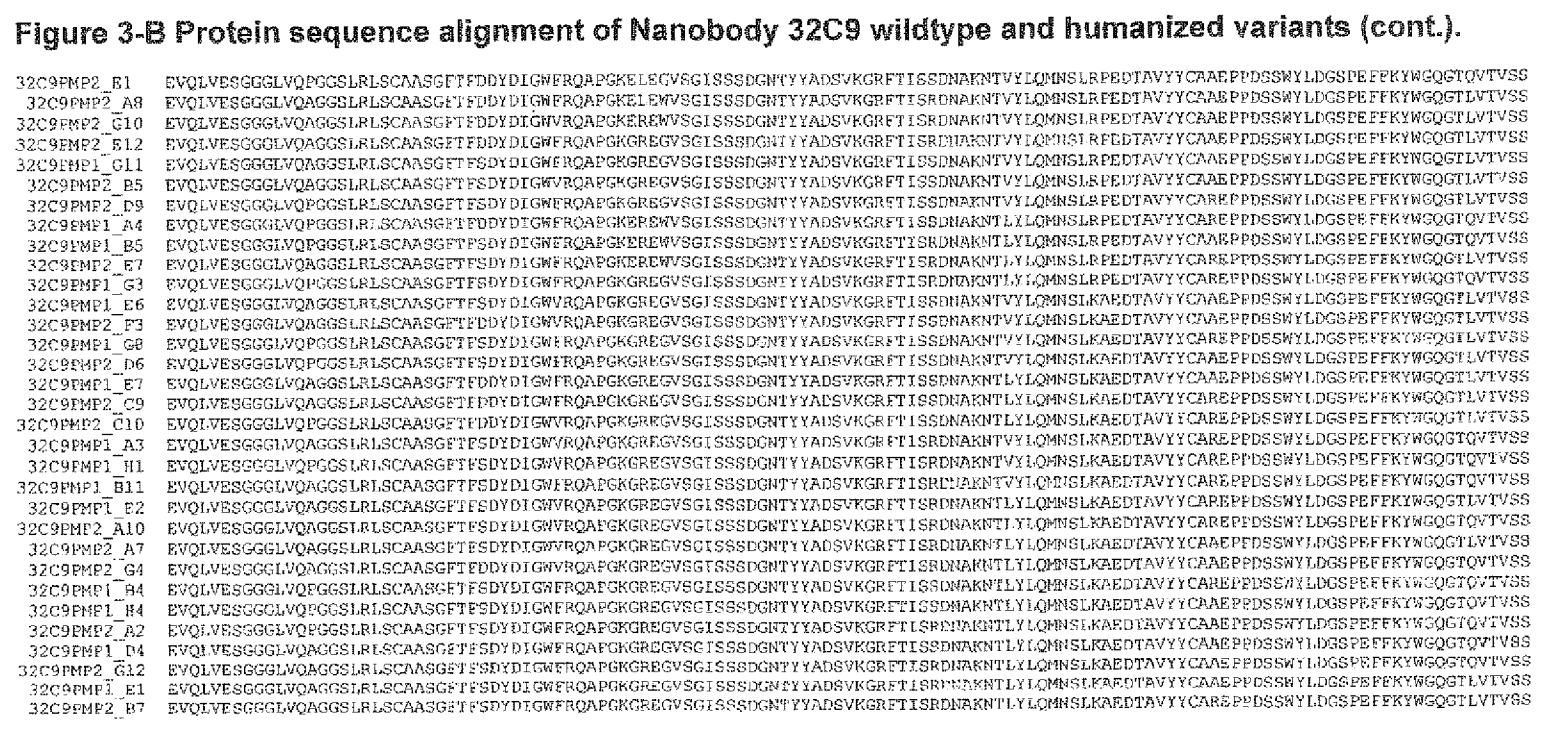

FIGS. 3-A and 3-B give a sequence alignment of 71 humanized variants (SEQ ID NO's: 50 to 212) of the Nanobody 32C9 (SEQ ID No: 49) obtained by PCR assembly using the set of 26 overlapping oligonucleotides (SEQ ID NO's: 23 to 48) shown in FIG. 2.

FIG. 4: Amino acid composition of the CDR1/2 libraries (library a and b) and CDR3 library (library c) of Nanobody IL6R65. A few additional substitutions were introduced in CDR3 (library c) to increase the diversity to 1×10e6. CDR regions are underlined.

FIG. 5: Evaluation of IL6R65 and 5 affinity matured variants in a cyno plasma potency assay.

Figure 6:
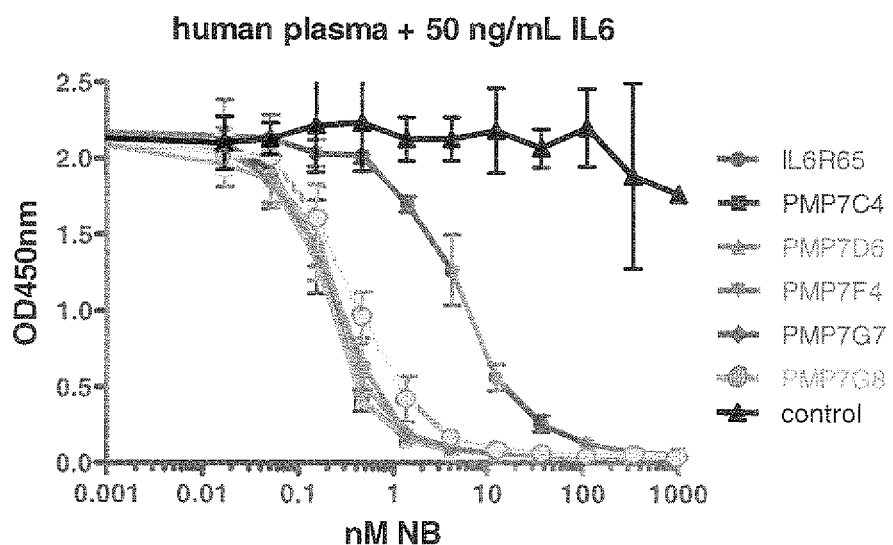

FIG. 6: Evaluation of IL6R65 and 5 affinity matured variants in a human plasma potency assay.

Figure 7:
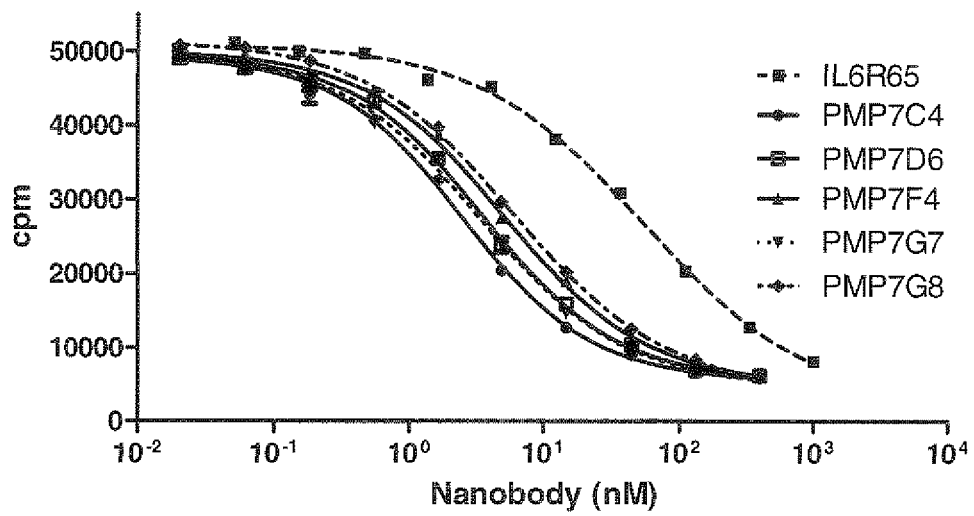

FIG. 7: Inhibition of IL6-dependent proliferation of TF-1 cells. Cells were grown in the presence of 2 ng/ml human IL6 and various concentrations of Nanobody. Proliferation was measured by 3H-thymidine incorporation.

PREFERRED ASPECTS

1. Method for providing a set, collection or library of nucleotide sequences or nucleic acids that encode amino acid sequences that can be used as (and/or are intended for use as) single antigen-binding domains, which method at least comprises the steps of:
    a) providing a pool of oligonucleotides that comprises (i) a series of at least two oligonucleotides that can be assembled, by means of PCR assembly, into a nucleotide sequence or nucleic acid that encodes an amino acid sequence that can be used as a single antigen-binding domain, and in addition comprises (ii) at least one variant of at least one of the at least two oligonucleotides that form part of the series, in which said at least one variant differs from said oligonucleotide (and also from the other variants of said oligonucleotide present in the pool, if any) in that it encodes an amino acid sequence that differs in the presence of one or more specific mutations; and
    b) subjecting the pool of oligonucleotides to PCR assembly.
2. Method according to aspect 1, in which the set, collection or library of nucleotide sequences or nucleic acids provided is a set, collection or library of nucleotide sequences that each encode an amino acid sequence that is an analog of a predetermined amino acid sequence (and in which the set, collection or library may optionally also contain a nucleotide sequence that encodes the predetermined amino acid sequence).

3. Method according to aspect 1 or 2, in which the oligonucleotides and variants thereof used in step a) are such that the nucleotide sequences obtained as a result of the PCR assembly in step b) encode amino acid sequences that contain an immunoglobulin fold or that are capable of forming an immunoglobulin fold.

4. Method according to aspect 1 or 2, in which the oligonucleotides and variants thereof used in step a) are such that the nucleotide sequences obtained as a result of the PCR assembly in step b) encode amino acid sequences that comprise or essentially consist of 4 framework regions and 3 complementarity determining regions.

5. Method according to aspect 4, in which the oligonucleotides and variants thereof used in step a) are such that the nucleotide sequences obtained as a result of the PCR assembly in step b) encode amino acid sequences that comprise or essentially consist of 4 framework regions and 3 complementarity determining regions that differ from each other in the presence of one or more specific mutations in the framework regions.

6. Method according to aspect 4,
   in which the oligonucleotides and variants thereof used in step a) are such that the nucleotide sequences obtained as a result of the PCR assembly in step b) encode amino acid sequences that comprise or essentially consist of 4 framework regions and 3 complementarity determining regions that differ from each other in the presence of one or more specific mutations in or close to the complementarity determining regions (preferably all oligonucleotides and variants thereof encoding amino acids in or close to CDR1 CDR2 and/or CDR3 are mutated); and wherein
   c) optionally in which the oligonucleotides and variants thereof used in step a) are such that the nucleotide sequences obtained as a result of the PCR assembly in step b) encode amino acid sequences that comprise or essentially consist of at least one specific mutation, more preferably 90% of specific mutations, or most preferred all of the one or more specific mutations in or close to the complementarity determining regions that are generated following the rules described in i) or ii), wherein for
   i) the one or more specific mutations in or close to the complementarity determining regions (CDRs) are generated by substituting the original nucleotide sequence such that amino acid residue with the following predetermined amino acid residue(s) are generated:
      if original amino acid residue is K, substitute with R;
      if original amino acid residue is R, substitute with K;
      if original amino acid residue is A, substitute with S or T or both,
      if original amino acid residue is S, substitute with A or T or both,
      if original amino acid residue is T, substitute with A or S or both,
      if original amino acid residue is I, substitute with L or V or both;
      if original amino acid residue is L, substitute with I or V or both;
      if original amino acid residue is V, substitute with I or L or both;
      if original amino acid residue is F, substitute with Y;
      if original amino acid residue is Y, substitute with F;
      if original amino acid residue is N, substitute with D;
      if original amino acid residue is D, substitute with N;
      if original amino acid residue is Q, substitute with E;
      if original amino acid residue is E, substitute with Q;
      if original amino acid residue is G, substitute with A;
      if original amino acid residue is M, substitute with L; or
      if original amino acid residue is H, C, W or P, do not substitute original amino acid residue; and wherein for
   ii) the one or more specific mutations in CDR3 are generated using the rules as above in i) and the one or more specific mutations in or close to CDR1 and 2 are generated by substituting the original nucleotide sequence such that amino acid residue with the following predetermined amino acid residue(s) are generated:
      if original amino acid residue in position 27 is to be mutated, substitute it with any of F, G, R, and S;
      if original amino acid residue in position 28 is to be mutated, substitute it with any of A, I, S, T;
      if original amino acid residue in position 29 is to be mutated, substitute it with any of F, G, L, S;
      if original amino acid residue in position 30 is to be mutated, substitute it with any of D, G, S, T;
      if original amino acid residue in position 31 is to be mutated, substitute it with any of D, I, N, S, T;
      if original amino acid residue in position 32 is to be mutated, substitute it with any of D, N, Y;
      if original amino acid residue in position 33 is to be mutated, substitute it with any of A, G, T, V;
      if original amino acid residue in position 34 is to be mutated, substitute it with any of I, M;
      if original amino acid residue in position 35 is to be mutated, substitute it with any of A, G, S;
      and if original amino acid sequence has an amino acid sequence in position 52a in CDR2, use the following rules:
         if original amino acid residue in position 50 is to be mutated, substitute it with any of A, C, G, S, T;
         if original amino acid residue in position 51 is to be mutated, substitute it with I;
         if original amino acid residue in position 52 is to be mutated, substitute it with any of N, R, S, T;
         if original amino acid residue in position 52a is to be mutated, substitute it with any of R, S, T, W;
         if original amino acid residue in position 53 is to be mutated, substitute it with any of D, G, N, S, T;
         if original amino acid residue in position 54 is to be mutated, substitute it with any of D, G;
         if original amino acid residue in position 55 is to be mutated, substitute it with any of D, G. S;
         if original amino acid residue in position 56 is to be mutated, substitute it with any of I, N, R, S, T;
         if original amino acid residue in position 57 is to be mutated, substitute it with T;
         if original amino acid residue in position 58 is to be mutated, substitute it with any of D, H, N, S, Y; or
      if original amino acid sequence has not an amino acid sequence in position 52a in CDR2, use the following rules:
         if original amino acid residue in position 50 is to be mutated, substitute it with any of A, G, R, S, T;
         if original amino acid residue in position 51 is to be mutated, substitute it with I;
         if original amino acid residue in position 52 is to be mutated, substitute it with any of N, S, T;
         if original amino acid residue in position 53 is to be mutated, substitute it with any of N, R, S, T, Y;

if original amino acid residue in position 54 is to be mutated, substitute it with any of D, G, R, S;
if original amino acid residue in position 55 is to be mutated, substitute it with any of G;
if original amino acid residue in position 56 is to be mutated, substitute it with any of G, N, R, S, T;
if original amino acid residue in position 57 is to be mutated, substitute it with T;
if original amino acid residue in position 58 is to be mutated, substitute it with any of D, N, T, Y.

7. Method according to aspect 4, in which the oligonucleotides and variants thereof used in step a) are such that the nucleotide sequences obtained as a result of the PCR assembly in step b) encode amino acid sequences that comprise or essentially consist of 4 framework regions and 3 complementarity determining regions that differ from each other in the presence of one or more specific mutations in the framework regions as well as one or more specific mutations in the complementarity determining regions; and wherein c) optionally in which the oligonucleotides and variants thereof used in step a) are such that the nucleotide sequences obtained as a result of the PCR assembly in step b) encode amino acid sequences that comprise or essentially consist of at least one specific mutation, more preferably 90% of specific mutations, or most preferred all of the one or more specific mutations in the complementarity determining regions that are generated following the rules described in i) or ii), wherein for i) the one or more specific mutations in the complementarity determining regions (CDRs) are generated by substituting the original nucleotide sequence such that amino acid residue with the following predetermined amino acid residue(s) are generated:
if original amino acid residue is K, substitute with R;
if original amino acid residue is R, substitute with K;
if original amino acid residue is A, substitute with S or T or both,
if original amino acid residue is S, substitute with A or T or both,
if original amino acid residue is T, substitute with A or S or both,
if original amino acid residue is I, substitute with L or V or both;
if original amino acid residue is L, substitute with I or V or both;
if original amino acid residue is V, substitute with I or L or both;
if original amino acid residue is F, substitute with Y;
if original amino acid residue is Y, substitute with F;
if original amino acid residue is N, substitute with D;
if original amino acid residue is D, substitute with N;
if original amino acid residue is Q, substitute with E;
if original amino acid residue is E, substitute with Q;
if original amino acid residue is G, substitute with A;
if original amino acid residue is M, substitute with L; or
if original amino acid residue is H, C, W or P, do not substitute original amino acid residue; and wherein for ii) the one or more specific mutations in CDR3 are generated using the rules as above in i) and the one or more specific mutations in CDR1 and 2 are generated by substituting the original nucleotide sequence such that amino acid residue with the following predetermined amino acid residue(s) are generated:

if original amino acid residue in position 27 is to be mutated, substitute it with any of F, G, R, and S;
if original amino acid residue in position 28 is to be mutated, substitute it with any of A, I, S, T;
if original amino acid residue in position 29 is to be mutated, substitute it with any of F, G, L, S;
if original amino acid residue in position 30 is to be mutated, substitute it with any of D, G, S, T;
if original amino acid residue in position 31 is to be mutated, substitute it with any of D, I, N, S, T;
if original amino acid residue in position 32 is to be mutated, substitute it with any of D, N, Y;
if original amino acid residue in position 33 is to be mutated, substitute it with any of A, G, T, V;
if original amino acid residue in position 34 is to be mutated, substitute it with any of I, M;
if original amino acid residue in position 35 is to be mutated, substitute it with any of A, G, S;

and if original amino acid sequence has an amino acid sequence in position 52a in CDR2, use the following rules:
if original amino acid residue in position 50 is to be mutated, substitute it with any of A, C, G, S, T;
if original amino acid residue in position 51 is to be mutated, substitute it with I;
if original amino acid residue in position 52 is to be mutated, substitute it with any of N, R, S, T;
if original amino acid residue in position 52a is to be mutated, substitute it with any of R, S, T, W;
if original amino acid residue in position 53 is to be mutated, substitute it with any of D, G, N, S, T;
if original amino acid residue in position 54 is to be mutated, substitute it with any of D, G;
if original amino acid residue in position 55 is to be mutated, substitute it with any of D, G, S;
if original amino acid residue in position 56 is to be mutated, substitute it with any of I, N, R, S, T;
if original amino acid residue in position 57 is to be mutated, substitute it with T;
if original amino acid residue in position 58 is to be mutated, substitute it with any of D, H, N, S, Y; or if original amino acid sequence has not an amino acid sequence in position 52a in CDR2, use the following rules:
if original amino acid residue in position 50 is to be mutated, substitute it with any of A, G, R, S, T;
if original amino acid residue in position 51 is to be mutated, substitute it with I:
if original amino acid residue in position 52 is to be mutated, substitute it with any of N, S, T;
if original amino acid residue in position 53 is to be mutated, substitute it with any of N, R, S, T, Y;
if original amino acid residue in position 54 is to be mutated, substitute it with any of D, G, R, S;
if original amino acid residue in position 55 is to be mutated, substitute it with any of G;
if original amino acid residue in position 56 is to be mutated, substitute it with any of G, N, R, S, T;
if original amino acid residue in position 57 is to be mutated, substitute it with T;
if original amino acid residue in position 58 is to be mutated, substitute it with any of D, N, T, Y.

8. Method according to any of aspects 4 to 7, in which the oligonucleotides and variants thereof used in step a) are such that the nucleotide sequences obtained as a result of the PCR assembly in step b) encode amino acid sequences that comprise or essentially consist of an immunoglobulin variable domain sequence or a suitable fragment thereof.
9. Method according to aspect 8, in which the oligonucleotides and variants thereof used in step a) are such that the nucleotide sequences obtained as a result of the PCR assembly in step b) encode amino acid sequences that comprise or essentially consist of a domain antibody or an amino acid sequence that is suitable for use as a domain antibody, a single domain antibody or an amino acid sequence that is suitable for use as a single domain antibody, a "dAb" or an amino acid sequence that is suitable for use as a dAb, or a Nanobody™, or any suitable fragment thereof.
10. Method according to aspect 9, in which the oligonucleotides and variants thereof used in step a) are such that the nucleotide sequences obtained as a result of the PCR assembly in step b) encode amino acid sequences that comprise or essentially consist of a Nanobody™.
11. Set, collection or library of nucleotide sequences or nucleic acids that can be obtained using a method according to any of aspects 1 to 10.
12. Method for generating a set, collection or library of amino acid sequences that can be used as (and/or are intended for use as) single antigen-binding domains, which method comprises subjecting a set, collection or library of nucleotide sequences or nucleic acids according to aspect 11 and/or obtained using a method according to any of aspects 1 to 10 to translation and/or expression.
13. Set, collection or library of amino acid sequences that can be obtained using the method of aspect 12.
14. Nucleotide sequence or nucleic acid that can be obtained using a method according to any of aspects 1 to 10 and/or from the set, collection or library according to aspect 11.
15. Amino acid sequence that can be obtained by expressing a nucleotide sequence or nucleic acid according to aspect 14.
16. Method according to any of aspects 1 to 10, which further comprises the step of:
  c) screening the set, collection or library of nucleotide sequences or nucleic acids obtained through steps a) and b) for nucleotide sequences or nucleic acids that encode amino acid sequences that have one or more desired properties (or combination of desired properties), and optionally isolating one or more nucleotide sequences or nucleic acids that encode amino acid sequences that have said one or more desired properties.
17. Method according to aspect 16, in which the set, collection or library of nucleotide sequences or nucleic acids that is screened encodes a set, collection or library of amino acid sequences that are analogs of a predetermined amino acid sequence, in which said set, collection or library of nucleotide sequences or nucleic acids optionally also includes a nucleotide sequence or nucleic acid that encodes the predetermined amino acid sequence.
18. Method according to aspect 17, in which the set, collection or library of nucleotide sequences that is screened is screened for nucleotide sequences or nucleic acids that encode analogs with one or more improved properties compared to the predetermined amino acid sequence.
19. Method according to any of aspects 1 to 10, which further comprises the step of:
  c) testing one or more nucleotide sequences or nucleic acids from the set, collection or library of nucleotide sequences or nucleic acids obtained through steps a) and b) as to whether they encode an amino acid sequence that has one or more desired properties (or combination of desired properties).
20. Method according to aspect 19, in which the one or more nucleotide sequences or nucleic acids that are tested encode amino acid sequences that are analogs of a predetermined amino acid sequence, and optionally also encode the predetermined amino acid sequence.
21. Method according to aspect 20, in which the one or more nucleotide sequences or nucleic acids that are tested are tested in order to identify and/or provide nucleotide sequences or nucleic acids that encode analogs with one or more improved properties compared to the predetermined amino acid sequence.
22. Method according to aspects 16 to 21, in which the one or more properties are one or more of the following properties of the amino acid sequence encoded by the nucleotide sequence(s) or nucleic acid(s) that are screened or tested: the affinity or specificity for an intended antigen, the potency or activity, the selectivity, the solubility, the stability, the tendency to aggregate, the "stickyness", the folding of the amino acid sequence, the degree of sequence identity with the closest human germline sequence, the presence of epitopes that might be recognized by the human immune system, the potential immunogenicity, the presence of one or more amino acid residues or of a stretch of amino acid residues that allow(s) the amino acid sequence to undergo one or more interactions other than the interaction with the intended antigen, the expression levels in a desired host or host cell, the half-life, the presence or absence of sites that can be modified, the presence or absence of sites or amino acid residues that can be subject to oxidation, the presence or absence of cysteine residues that can form disulphide bridges, and/or the ability to cross biological membranes or barriers; or any desired combination of any of the foregoing.
23. Method according to aspect 22, in which the one or more properties are one or more of the following properties of the amino acid sequence(s) encoded by the nucleotide sequence(s) or nucleic acid(s) that are screened or tested: the affinity or specificity for an intended antigen, the potency or activity and/or the selectivity.
24. Method according to aspect 23, in which the one or more properties at least comprise the affinity or specificity for an intended antigen of the amino acid sequence(s) encoded by the nucleotide sequence(s) or nucleic acid(s) that are screened or tested.
25. Method according to aspect 22 or 23, in which the oligonucleotides and variants thereof used in step a) are such that the nucleotide sequences or nucleic acids obtained as a result of the PCR assembly in step b) encode amino acid sequences that comprise or essentially consist of 4 framework regions and 3 complementarity determining regions that differ from each other in the presence of one or more specific mutations in the complementarity determining regions.
26. Method according to aspect 22, in which the one or more properties are one or more of the following properties of the amino acid sequence(s) encoded by the nucleotide sequence(s) or nucleic acid(s) that are screened or tested: the stability, the tendency to aggregate, the "stickyness", the folding of the amino acid sequence and/or the expression levels in a desired host or host cell
27. Method according to aspect 27, in which the one or more properties at least comprise the stability, the tendency to aggregate and/or the "stickyness" of the amino acid sequence encoded by the nucleotide sequence or nucleic acid.
28. Method according to aspect 26 or 27, in which the oligonucleotides and variants thereof used in step a) are such that the nucleotide sequences or nucleic acids obtained as a result of the PCR assembly in step b) encode amino acid sequences that comprise or essentially consist of 4 framework regions and 3 complementarity determining regions that differ from each other in the presence of one or more specific mutations in the framework regions.
29. Method according to aspect 22, in which the one or more properties at least comprise the degree of sequence identity with the closest human germline sequence of the amino acid sequence(s) encoded by the nucleotide sequence(s) or nucleic acid(s) that are screened or tested.
30. Method according to aspect 29, in which the oligonucleotides and variants thereof used in step a) are such that the nucleotide sequences or nucleic acids obtained as a result of the PCR assembly in step b) encode amino acid sequences that comprise or essentially consist of 4 framework regions and 3 complementarity determining regions that differ from each other in the presence of one or more specific mutations in the framework regions.
31. Method according to aspect 22, in which the one or more properties at least comprise the presence of epitopes that might be recognized by the human immune system in the amino acid sequence(s) encoded by the nucleotide sequence(s) or nucleic acid(s) that are screened or tested and/or at least comprise the potential immunogenicity (if any) of the amino acid sequence(s) encoded by the nucleotide sequence(s) or nucleic acid(s) that are screened or tested.
32. Method according to aspect 31, in which the oligonucleotides and variants thereof used in step a) are such that the nucleotide sequences or nucleic acids obtained as a result of the PCR assembly in step b) encode amino acid sequences that differ from each other in the presence of one or more specific mutations in the amino acid residues that correspond to epitopes that might be recognized by the human immune system
33. Nucleotide sequence or nucleic acid that can be obtained via a method according to any of aspects 16 to 32.
34. Amino acid sequence that can be obtained by expressing a nucleotide sequence or nucleic acid according to aspect 33.
35. Method for providing one or more nucleotide sequences or nucleic acids that encode amino acid sequences that can be used as (and/or are intended for use as) single antigen-binding domains and that have one or more desired properties (or a combination of desired properties), which method comprises screening a set, collection or library of nucleotide sequences or nucleic acids according to aspect 11 for nucleotide sequences that encode amino acid sequences that have said one or more desired properties (or combination or desired properties), and optionally isolating one or more nucleotide sequences that encode amino acid sequences with said one or more desired properties.
36. Method according to aspect 35, in which the set, collection or library of nucleotide sequences or nucleic acids that is screened encodes a set, collection or library of amino acid sequences that are analogs of a predetermined amino acid sequence, in which said set, collection or library of nucleotide sequences or nucleic acids optionally also includes a nucleotide sequence or nucleic acid that encodes the predetermined amino acid sequence.
37. Method according to aspect 36, in which the set, collection or library of nucleotide sequences that is screened is screened for nucleotide sequences or nucleic acids that encode analogs with one or more improved properties compared to the predetermined amino acid sequence.
38. Method for providing one or more nucleotide sequences or nucleic acids that encode amino acid sequences that can be used as (and/or are intended for use as) single antigen-binding domains and that have with one or more desired properties (or a combination of desired properties), which method comprises testing whether one or more of the nucleotide sequences or nucleic acids from the set, collection or library of nucleotide sequences according to aspect 11 and/or one or more nucleotide sequences or nucleic acids according to aspect 12 encode an amino acid sequence that has said one or more desired properties.
39. Method according to aspect 38, in which the one or more nucleotide sequences or nucleic acids that are tested encode amino acid sequences that are analogs of a predetermined amino acid sequence, and optionally also encode the predetermined amino acid sequence.
40. Method according to aspect 39, in which the one or more nucleotide sequences or nucleic acids that are tested are tested in order to identify and/or provide nucleotide sequences or nucleic acids that encode analogs with one or more improved properties compared to the predetermined amino acid sequence.
41. Method according to aspect any of aspects 35 to 40, in which the one or more properties are one or more of the following properties of the amino acid sequence(s) encoded by the nucleotide sequence(s) or nucleic acid(s) that are screened or tested: the affinity or specificity for an intended antigen, the potency or activity, the selectivity, the solubility, the stability, the tendency to aggregate, the "stickyness", the folding of the amino acid sequence, the degree of sequence identity with the closest human germline sequence, the presence of epitopes that might be recognized by the human immune system, the potential immunogenicity, the presence of one or more amino acid residues or of a stretch of amino acid residues that allow(s) the amino acid sequence to undergo one or more interactions other than the interaction with the intended antigen, the expression levels in a desired host or host cell, the half-life, the presence or absence of sites that can be modified, the presence or absence of sites or amino acid residues that can be subject to oxidation, the presence or absence of cysteine residues that can form disulphide bridges, and/or the ability to cross biological membranes or barriers; or any desired combination of any of the foregoing.
42. Method according to aspect 41, in which the one or more properties are one or more of the following properties of the amino acid sequence(s) encoded by the nucleotide sequence(s) or nucleic acid(s) that are screened or tested: the affinity or specificity for an intended antigen, the potency or activity and/or the selectivity.
43. Method according to aspect 42, in which the one or more properties at least comprise the affinity or specificity for an intended antigen of the amino acid sequence(s) encoded by the nucleotide sequence(s) or nucleic acid(s) that are screened or tested.
44. Method according to aspect 42 or 43, in which the set, collection or library of nucleotide sequences or nucleic acids that is screened encodes amino acid sequences that comprise or essentially consist of 4 framework regions and 3 complementarity determining regions and that differ from each other in the presence of one or more specific mutations in the complementarity determining regions; and/or in which the nucleotide sequences or nucleic acids that are tested encode amino acid sequences that comprise or essentially consist of 4 framework regions and 3 complementarity determining regions and that differ from each other in the presence of one or more specific mutations in the complementarity determining regions.

45. Method according to aspect 41, in which the one or more properties are one or more of the following properties of the amino acid sequence(s) encoded by the nucleotide sequence(s) or nucleic acid(s) that are screened or tested: the stability, the tendency to aggregate, the "stickyness", the folding of the amino acid sequence and/or the expression levels in a desired host or host cell 46. Method according to aspect 45, in which the one or more properties at least comprise the stability, the tendency to aggregate and/or the "stickyness" of the amino acid sequence(s) encoded by the nucleotide sequence(s) or nucleic acid(s) that are screened or tested.

47. Method according to aspect 45 or 46, in which the set, collection or library of nucleotide sequences or nucleic acids that is screened encode amino acid sequences that comprise or essentially consist of 4 framework regions and 3 complementarity determining regions and that differ from each other in the presence of one or more specific mutations in the framework regions; and/or in which the nucleotide sequences or nucleic acids that are tested encode amino acid sequences that comprise or essentially consist of 4 framework regions and 3 complementarity determining regions and that differ from each other in the presence of one or more specific mutations in the framework regions.

48. Method according to aspect 41, in which the one or more properties at least comprise the degree of sequence identity with the closest human germline sequence of the amino acid sequence(s) encoded by the nucleotide sequence(s) or nucleic acid(s) that are screened or tested.

49. Method according to aspect 48, in which the set, collection or library of nucleotide sequences or nucleic acids that is screened encode amino acid sequences that comprise or essentially consist of 4 framework regions and 3 complementarity determining regions and that differ from each other in the presence of one or more specific mutations in the framework regions; and/or in which the nucleotide sequences or nucleic acids that are tested encode amino acid sequences that comprise or essentially consist of 4 framework regions and 3 complementarity determining regions and that differ from each other in the presence of one or more specific mutations in the framework regions.

50. Method according to aspect 41, in which the one or more properties at least comprise the presence of epitopes that might be recognized by the human immune system and/or the potential immunogenicity (if any) of the amino acid sequence(s) encoded by the nucleotide sequence(s) or nucleic acid(s) that are screened or tested.

51. Method according to aspect 48, in which the set, collection or library of nucleotide sequences or nucleic acids that is screened encode amino acid sequences that comprise or essentially consist of 4 framework regions and 3 complementarity determining regions and that differ from each other in the presence of one or more specific mutations in the amino acid residues that correspond to epitopes that might be recognized by the human immune system; and/or in which the nucleotide sequences or nucleic acids that are tested encode amino acid sequences that comprise or essentially consist of 4 framework regions and 3 complementarity determining regions and that differ from each other in the presence of one or more specific mutations in the amino acid residues that correspond to epitopes that might be recognized by the human immune system.

52. Nucleotide sequence or nucleic acid that can be obtained using a method according to any of aspects 35 to 51.

53. Amino acid sequence that can be obtained by expressing a nucleotide sequence or nucleic acid according to aspect 52.

54. Method for providing a set, collection or library of amino acid sequences that can be used as (and/or are intended for use as) single antigen-binding domains, which method at least comprises the steps of:
  a) providing a pool of oligonucleotides that comprises (i) a series of at least two oligonucleotides that can be assembled, by means of PCR assembly, into a nucleotide sequence that encodes an amino acid sequence that can be used as (or is intended for use as) a single antigen-binding domain, and in addition comprises (ii) at least one variant of at least one of the at least two oligonucleotides that form part of the series, in which said at least one variant differs from said oligonucleotide (and also from the other variants of said oligonucleotide present in the pool, if any) in that it encodes an amino acid sequence that differs in the presence of one or more specific mutations;
  b) subjecting the pool of oligonucleotides to PCR assembly;
  and
  c) subjecting (two or more of) the assembled oligonucleotide sequences thus obtained to translation and/or expression in a suitable manner known per se.

55. Method according to aspect 54, in which the set, collection or library of amino acid sequences provided after step c) is a set, collection or library of analogs of a predetermined amino acid sequence (which set, collection or library may optionally also contain the predetermined amino acid sequence).

56. Method according to aspect 1 or 2, in which the oligonucleotides and variants thereof used in step a) are such that the amino acid sequences provided after step c) contain an immunoglobulin fold or that are capable of forming an immunoglobulin fold.

57. Method according to aspect 1 or 2, in which the oligonucleotides and variants thereof used in step a) are such that the amino acid sequences provided after step c) comprise or essentially consist of 4 framework regions and 3 complementarity determining regions.

58. Method according to aspect 4, in which the oligonucleotides and variants thereof used in step a) are such that the amino acid sequences provided after step c) comprise or essentially consist of 4 framework regions and 3 complementarity determining regions and differ from each other in the presence of one or more specific mutations in the framework regions.

59. Method according to aspect 4, in which the oligonucleotides and variants thereof used in step a) are such that the amino acid sequences provided after step c) comprise or essentially consist of 4 framework regions and 3 complementarity determining regions and differ from each other in the presence of one or more specific mutations in the complementarity determining regions.

60. Method according to aspect 4, in which the oligonucleotides and variants thereof used in step a) are such that the amino acid sequences provided after step c) comprise or essentially consist of 4 framework regions and 3 complementarity determining regions and differ from each other in the presence of one or more specific mutations in the framework regions as well as one or more specific mutations in the complementarity determining regions.
61. Method according to any of aspects 4 to 7, in which the oligonucleotides and variants thereof used in step a) are such that the amino acid sequences provided after step c) comprise or essentially consist of an immunoglobulin variable domain sequence or a suitable fragment thereof.
62. Method according to aspect 8, in which the oligonucleotides and variants thereof used in step a) are such that the amino acid sequences provided after step c) comprise or essentially consist of a domain antibody or an amino acid sequence that is suitable for use as a domain antibody, a single domain antibody or an amino acid sequence that is suitable for use as a single domain antibody, a "dAb" or an amino acid sequence that is suitable for use as a dAb, or a Nanobody™ or any suitable fragment thereof.
63. Method according to aspect 9, in which the oligonucleotides and variants thereof used in step a) are such that the amino acid sequences provided after step c) comprise or essentially consist of a Nanobody™.
64. Set, collection or library of amino acid sequences that can be obtained using a method according to any of aspects 54 to 63.
65. Amino acid sequences that can be obtained using a method according to any of aspects 54 to 63 and/or from the set, collection or library according to aspect 64.
66. Method according to any of aspects 54 to 63, which further comprises the step of:
   d) screening the set, collection or library of amino acid sequences obtained through steps a) to c) for amino acid sequences that have one or more desired properties (or combination of desired properties), and optionally isolating one or more amino acid sequences that have said one or more desired properties.
67. Method according to aspect 66, in which the set, collection or library of amino acid sequences that is screened is a set, collection or library of amino acid sequences that are analogs of a predetermined amino acid sequence, in which said set, collection or library optionally also includes the predetermined amino acid sequence.
68. Method according to aspect 67, in which the set, collection or library of amino acid sequences that is screened is screened for analogs with one or more improved properties compared to the predetermined amino acid sequence.
69. Method according to any of aspects 54 to 63, which further comprises the step of:
   d) testing one or more amino acid sequences from the set, collection or library of amino acid sequences obtained through steps a) to c) as to whether they have one or more desired properties (or combination of desired properties).
70. Method according to aspect 69, in which the one or more amino acid sequences that are tested are amino acid sequences that are analogs of a predetermined amino acid sequence, optionally together with the predetermined amino acid sequence.
71. Method according to aspect 70, in which the one or more amino acid sequences that are tested are tested in order to identify and/or provide analogs with one or more improved properties compared to the predetermined amino acid sequence.
72. Method according to aspect any of aspects 66 to 71, in which the one or more properties are one or more of the following properties of the amino acid sequence(s) that are screened or tested: the affinity or specificity for an intended antigen, the potency or activity, the selectivity, the solubility, the stability, the tendency to aggregate, the "stickyness", the folding of the amino acid sequence, the degree of sequence identity with the closest human germline sequence, the presence of epitopes that might be recognized by the human immune system, the potential immunogenicity, the presence of one or more amino acid residues or of a stretch of amino acid residues that allow(s) the amino acid sequence to undergo one or more interactions other than the interaction with the intended antigen, the expression levels in a desired host or host cell, the half-life, the presence or absence of sites that can be modified, the presence or absence of sites or amino acid residues that can be subject to oxidation, the presence or absence of cysteine residues that can form disulphide bridges, and/or the ability to cross biological membranes or barriers; or any desired combination of any of the foregoing.
73. Method according to aspect 72, in which the one or more properties are one or more of the following properties of the amino acid sequence(s) that are screened or tested: the affinity or specificity for an intended antigen, the potency or activity and/or the selectivity.
74. Method according to aspect 73, in which the one or more properties at least comprise the affinity or specificity for an intended antigen of the amino acid sequence(s) that are screened or tested.
75. Method according to aspect 72 or 73, in which the oligonucleotides and variants thereof used in step a) are such that the amino acid sequences obtained after step c) comprise or essentially consist of 4 framework regions and 3 complementarity determining regions and differ from each other in the presence of one or more specific mutations in the complementarity determining regions.
76. Method according to aspect 72, in which the one or more properties are one or more of the following properties of the amino acid sequence(s) encoded by the nucleotide sequence(s) or nucleic acid(s) that are screened or tested: the stability, the tendency to aggregate, the "stickyness", the folding of the amino acid sequence and/or the expression levels in a desired host or host cell
77. Method according to aspect 27, in which the one or more properties at least comprise the stability, the tendency to aggregate and/or the "stickyness" of the amino acid sequence encoded by the nucleotide sequence or nucleic acid.
78. Method according to aspect 26 or 27, in which the oligonucleotides and variants thereof used in step a) are such that the amino acid sequences obtained after step c) comprise or essentially consist of 4 framework regions and 3 complementarity determining regions and differ from each other in the presence of one or more specific mutations in the framework regions.
79. Method according to aspect 72, in which the one or more properties at least comprise the degree of sequence identity with the closest human germline sequence of the amino acid sequence(s) that are screened or tested.
80. Method according to aspect 79, in which the oligonucleotides and variants thereof used in step a) are such that the amino acid sequences obtained after step c) comprise or essentially consist of 4 framework regions and 3 complementarity determining regions and differ from each other in the presence of one or more specific mutations in the framework regions.
81. Method according to aspect 72, in which the one or more properties at least comprise the presence of epitopes that might be recognized by the human immune system in the amino acid sequence(s) are screened or tested and/or at least comprise the potential immunogenicity (if any) of the amino acid sequence(s) are screened or tested.
82. Method according to aspect 81, in which the oligonucleotides and variants thereof used in step a) are such that the amino acid sequences obtained after step c) differ from each other in the presence of one or more specific mutations in the amino acid residues that correspond to epitopes that might be recognized by the human immune system
83. Amino acid sequence that can be obtained via a method according to any of aspects 66 to 82.
84. Method for providing one or more amino acid sequences that can be used as (and/or are intended for use as) single antigen-binding domains and that have one or more desired properties (or a combination of desired properties), which method comprises screening a set, collection or library of amino acid sequences according to aspect 64 for nucleotide sequences that encode amino acid sequences that have said one or more desired properties (or combination or desired properties), and optionally isolating one or more nucleotide sequences that encode amino acid sequences with said one or more desired properties.
85. Method according to aspect 84, in which the set, collection or library of amino acid sequences that is screened is set, collection or library of amino acid sequences that are analogs of a predetermined amino acid sequence, in which said set, collection or library optionally also includes the predetermined amino acid sequence.
86. Method according to aspect 85, in which the set, collection or library of amino acid sequences that is screened is screened for analogs with one or more improved properties compared to the predetermined amino acid sequence.
87. Method for providing one or more amino acid sequences that can be used as (and/or are intended for use as) single antigen-binding domains and that have with one or more desired properties (or a combination of desired properties), which method comprises testing whether one or more of the amino acid sequences from the set, collection or library of nucleotide sequences according to aspect 64 and/or one or amino acid sequences according to aspect 65 have said one or more desired properties.
88. Method according to aspect 87, in which the one or more amino acid sequences are tested are analogs of a predetermined amino acid sequence, and optionally also include the predetermined amino acid sequence.
89. Method according to aspect 88, in which the one or more amino acid sequences that are tested are tested in order to identify and/or provide analogs with one or more improved properties compared to the predetermined amino acid sequence.
90. Method according to aspect any of aspects 84 to 89, in which the one or more properties are one or more of the following properties of the amino acid sequence(s) that are screened or tested: the affinity or specificity for an intended antigen, the potency or activity, the selectivity, the solubility, the stability, the tendency to aggregate, the "stickyness", the folding of the amino acid sequence, the degree of sequence identity with the closest human germline sequence, the presence of epitopes that might be recognized by the human immune system, the potential immunogenicity, the presence of one or more amino acid residues or of a stretch of amino acid residues that allow(s) the amino acid sequence to undergo one or more interactions other than the interaction with the intended antigen, the expression levels in a desired host or host cell, the half-life, the presence or absence of sites that can be modified, the presence or absence of sites or amino acid residues that can be subject to oxidation, the presence or absence of cysteine residues that can form disulphide bridges, and/or the ability to cross biological membranes or barriers; or any desired combination of any of the foregoing.
91. Method according to aspect 90, in which the one or more properties are one or more of the following properties of the amino acid sequence(s) that are screened or tested: the affinity or specificity for an intended antigen, the potency or activity and/or the selectivity.
92. Method according to aspect 91, in which the one or more properties at least comprise the affinity or specificity for an intended antigen of the amino acid sequence(s) that are screened or tested.
93. Method according to aspect 91 or 92, in which the set, collection or library of amino acid sequences that is screened is a set, collection or library of amino acid sequences that comprise or essentially consist of 4 framework regions and 3 complementarity determining regions and that differ from each other in the presence of one or more specific mutations in the complementarity determining regions; and/or in which the amino acid sequences that are tested are amino acid sequences that comprise or essentially consist of 4 framework regions and 3 complementarity determining regions and that differ from each other in the presence of one or more specific mutations in the complementarity determining regions.
94. Method according to aspect 90, in which the one or more properties are one or more of the following properties of the amino acid sequence(s) that are screened or tested: the stability, the tendency to aggregate, the "stickyness", the folding of the amino acid sequence and/or the expression levels in a desired host or host cell
95. Method according to aspect 94, in which the one or more properties at least comprise the stability, the tendency to aggregate and/or the "stickyness" of the amino acid sequence(s) that are screened or tested.
96. Method according to aspect 94 or 95, in which the set, collection or library of amino acid sequences that is screened is a set, collection or library of amino acid sequences that comprise or essentially consist of 4 framework regions and 3 complementarity determining regions and that differ from each other in the presence of one or more specific mutations in the framework regions; and/or in which the amino acid sequences that are tested encode amino acid sequences are comprise or essentially consist of 4 framework regions and 3 complementarity determining regions and differ from each other in the presence of one or more specific mutations in the framework regions.
97. Method according to aspect 90, in which the one or more properties at least comprise the degree of sequence identity with the closest human germline sequence of the amino acid sequence(s) that are screened or tested.
98. Method according to aspect 91, in which the set, collection or library of nucleotide sequences or nucleic acids that is screened is a set, collection or library of amino acid sequences that comprise or essentially consist of 4 framework regions and 3 complementarity determining regions and that differ from each other in the presence of one or more specific mutations in the framework regions; and/or in which the amino acid sequences are tested encode amino acid sequences that comprise or essentially consist of 4 framework regions and 3 complementarity determining regions and differ from each other in the presence of one or more specific mutations in the framework regions.

99. Method according to aspect 90, in which the one or more properties at least comprise the presence of epitopes that might be recognized by the human immune system in the amino acid sequence(s) that are screened or tested and/or the potential immunogenicity (if any) of the amino acid sequence(s) that are screened or tested.

100. Method according to aspect 48, in which the set, collection or library of nucleotide sequences or nucleic acids that is screened is a set, collection or library of amino acid sequences that comprise or essentially consist of 4 framework regions and 3 complementarity determining regions and that differ from each other in the presence of one or more specific mutations in the amino acid residues that correspond to epitopes that might be recognized by the human immune system; and/or in which the amino acid sequences that are tested comprise or essentially consist of 4 framework regions and 3 complementarity determining regions and differ from each other in the presence of one or more specific mutations in the amino acid residues that correspond to epitopes that might be recognized by the human immune system.

101. Amino acid sequence that can be obtained using a method according to any of aspects 84 to 100.

102. Amino acid sequence selected from the group consisting of amino acid sequences having a sequence as shown in SEQ ID NO: 50 to 121, and amino acid sequences having a sequence as shown in SEQ ID NO: 123 to 176.

103. Amino acid sequence selected from the group consisting of amino acid sequences having a sequence as shown in SEQ ID NO: 50 to 121.

104. Amino acid sequence selected from the group consisting of amino acid sequences having a sequence as shown in SEQ ID NO: 74. SEQ ID NO: 93, SEQ ID NO: 94, SEQ ID NO: 104, SEQ ID NO: 105, SEQ ID NO: 116 to 120.

105. Amino acid sequence selected from the group consisting of amino acid sequences having a sequence as shown in SEQ ID NO: 123 to 176.

106. Amino acid sequence selected from the group consisting of amino acid sequences having a sequence as shown in SEQ ID NO: 123, SEQ ID NO: 149, SEQ ID NO: 152, SEQ ID NO: 156, SEQ ID NO: 169.

EXPERIMENTAL PART

Example 1: Library Based Humanization of Nanobody 32C9 (Also Referred to as IL6R04 and SEQ ID NO: 440 in WO2008020079A1)

A set of 26 overlapping oligonucleotides (shown in FIG. 2 and SEQ ID NO's: 23 to 48) was used for the assembly of a library of humanized variants of Nanobody 32C9 (IL6R04, SEQ ID NO: 49):

The oligos were dissolved in $H_2O$ and subsequently pooled at a final concentration of 0.4 uM for each oligo, and 1 ul of this mixture was used for assembly PCR in a 50 ul reaction volume. Full-length product was purified using the Qiagen PCR purification kit. The purified PCR product was then digested with SfiI and BsteETI and ligated into the corresponding sites of expression vector pAX51. E, coli TG 1 cells were transformed with 2 ul of ligation mixture and plated on LB agar+100 ug/ml ampicillin+2% glucose. Plates were incubated overnight at 37° C. Individual colonies were picked and grown overnight in 2×YT+100 ug/ml ampicillin+2% glucose. Cloned Nanobody genes were amplified directly from these cultures with M13 forward and reverse primers. PCR products were purified and subsequently sequenced. In parallel the same panel of Nanobodies was expressed at 1 ml scale for 4 hours at 37° C. Periplasmic extracts were prepared and without further purification analyzed on Biacore for their ability to bind human IL6R. Sequencing results for 71 IL6R04 variants obtained in this manner are shown in the FIGS. 3-A and 3-B and SEQ ID NO's: 50 to 121. The off-rates for these 71 variants are given in Table B-1 below. Based on these results it was concluded that residues 14, 30, 44, 71, 78, 83, 84 and 108 can be humanized without a significant effect (<2-fold) on the off-rate of Nanobody 32C9. In contrast, humanization of residue 94 completely abolishes the binding to IL6R while humanization of residues 37, 45 and 47 is associated with a 5-, 10- and 12-fold reduction in off-rate, respectively.

TABLE B-1

Off-rates and amino acid composition on the positions that were selected for humanization of Nanobody 32C9 wildtype and its humanized variants.

|  | 14 | 30 | 37 | 44 | 45 | 47 | 71 | 78 | 83 | 84 | 94 | 108 | OFF-RATE ($s^{-1}$) |
|---|---|---|---|---|---|---|---|---|---|---|---|---|---|
| 32C9 WT | A | D | F | E | R | G | S | V | K | P | A | Q | 1.62E-04 |
| 32C9PMP1_G5 | P | D | F | E | L | G | R | L | R | P | A | L | 1.16E-03 |
| 32C9PMP2_E2 | P | S | F | E | L | G | S | L | K | A | A | Q | 1.21E-03 |
| 32C9PMP2_E1 | P | D | F | E | L | G | S | V | R | P | A | Q | 1.66E-03 |
| 32C9PMP2_A12 | A | D | F | E | L | G | S | V | K | A | A | Q | 2.90E-03 |
| 32C9PMP1_B3 | P | D | V | E | L | G | S | L | R | P | A | L | 3.46E-03 |
| 32C9PMP1_C5 | A | D | V | E | L | G | S | V | R | P | A | L | 5.20E-03 |
| 32C9PMP2_D10 | P | S | V | E | L | G | S | V | R | P | A | L | 7.07E-03 |
| 32C9PMP1_F3 | A | S | V | E | L | G | S | V | K | A | A | Q | N.d. |
| 32C9PMP2_H6 | P | D | V | E | L | G | S | L | K | A | A | L | N.d. |
| 32C9PMP1_E7 | A | D | F | G | R | G | S | L | K | A | A | L | 1.87E-04 |
| 32C9PMP1_H4 | P | S | F | G | R | G | S | L | K | A | A | Q | 1.87E-04 |
| 32C9PMP2_A2 | P | S | F | G | R | G | R | L | K | A | A | Q | 1.92E-04 |
| 32C9PMP1_D4 | A | S | F | G | R | G | S | L | K | A | A | Q | 1.96E-04 |
| 32C9PMP2_G12 | A | S | F | G | R | G | R | L | K | A | A | Q | 1.97E-04 |

TABLE B-1-continued

Off-rates and amino acid composition on the positions that were selected for humanization of Nanobody 32C9 wildtype and its humanized variants.

| | 14 | 30 | 37 | 44 | 45 | 47 | 71 | 78 | 83 | 84 | 94 | 108 | OFF-RATE ($s^{-1}$) |
|---|---|---|---|---|---|---|---|---|---|---|---|---|---|
| 32C9PMP1_G11 | A | S | F | G | R | G | S | V | R | P | A | L | 2.04E-04 |
| 32C9PMP1_E1 | A | S | F | G | R | G | R | L | K | A | A | L | 2.05E-04 |
| P32C9PMP2_E12 | A | D | F | G | R | G | R | V | R | P | A | L | 2.47E-04 |
| 32C9PMP2_B3 | A | S | F | E | R | G | R | V | K | A | A | L | 3.08E-04 |
| 32C9PMP2_D6 | P | S | F | G | R | G | S | V | R | P | A | L | n.d. |
| 32C9PMP2_F12 | A | D | V | G | R | G | S | L | R | P | A | L | 5.84E-04 |
| 32C9PMP2_G4 | A | D | V | G | R | G | R | L | K | A | A | Q | 7.00E-04 |
| 32C9PMP2_A7 | A | S | V | G | R | G | R | L | K | A | A | L | 7.92E-04 |
| 32C9PMP2_B5 | A | S | V | G | R | G | S | V | R | P | A | L | 8.03E-04 |
| 32C9PMP2_F3 | A | D | V | G | R | G | S | V | K | A | A | L | 8.04E-04 |
| 32C9PMP1_E6 | A | S | V | G | R | G | S | V | K | A | A | L | 9.82E-04 |
| 32C9PMP2_A8 | A | D | F | E | L | W | R | V | R | P | A | L | n.d. |
| 32C9PMP1_H12 | A | S | V | E | L | W | S | L | K | A | A | L | n.d. |
| 32C9PMP1_F8 | A | S | F | E | R | W | S | L | K | A | A | L | 1.89E-03 |
| 32C9PMP1_B5 | P | S | F | E | R | W | R | L | R | P | A | Q | 1.96E-03 |
| 32C9PMP2_B12 | P | S | F | E | R | W | S | V | K | A | A | Q | 5.64E-03 |
| 32C9PMP2_C6 | A | S | V | G | R | W | S | L | R | P | A | Q | 4.26E-03 |
| 32C9PMP1_A1 | A | S | V | E | R | W | S | L | R | P | A | L | 5.15E-03 |
| 32C9PMP2_B11 | A | D | V | E | R | W | S | L | R | P | A | Q | 7.68E-03 |
| 32C9PMP2_C3 | A | S | V | E | R | W | S | L | K | A | A | Q | 1.38E-02 |
| 32C9PMP1_B7 | A | D | V | E | R | W | S | L | K | A | A | L | n.d. |
| 32C9PMP1_F10 | P | S | V | E | R | W | S | L | K | A | A | Q | n.d. |
| 32C9PMP1_F5 | P | S | V | E | R | W | S | L | K | A | A | Q | n.d. |
| 32C9PMP1_F7 | A | S | V | E | R | W | S | L | R | P | A | L | n.d. |
| 32C9PMP1_H5 | P | D | V | E | R | W | S | L | R | P | A | L | n.d. |
| 32C9PMP2_C8 | A | D | V | E | R | W | S | V | K | A | A | Q | n.d. |
| 32C9PMP2_G10 | A | D | V | E | R | W | R | V | R | P | A | L | n.d. |
| 32C9PMP1_A3 | A | S | V | G | R | G | R | V | K | A | R | Q | n.d. |
| 32C9PMP1_B11 | A | S | F | G | R | G | R | V | K | A | R | Q | n.d. |
| 32C9PMP1_B4 | P | S | F | G | R | G | S | L | K | A | R | Q | n.d. |
| 32C9PMP1_D5 | P | D | V | G | R | G | S | L | R | P | R | L | n.d. |
| 32C9PMP1_E2 | A | S | V | G | R | G | R | L | K | A | R | L | n.d. |
| 32C9PMP1_G3 | P | S | F | G | R | G | R | L | R | P | R | Q | n.d. |
| 32C9PMP1_G8 | P | S | F | G | R | G | S | V | K | A | R | L | n.d. |
| 32C9PMP1_G9 | P | D | V | E | L | G | S | V | K | A | R | L | n.d. |
| 32C9PMP1_H1 | P | S | V | G | R | G | R | V | K | A | R | Q | n.d. |
| 32C9PMP1_H6 | P | D | F | E | L | G | R | L | K | A | R | Q | n.d. |
| 32C9PMP1_H8 | A | D | V | G | R | G | R | L | R | P | R | L | n.d. |
| 32C9PMP2_A10 | A | S | V | G | R | G | R | L | K | A | R | Q | n.d. |
| 32C9PMP2_A5 | P | D | V | G | R | G | S | V | R | P | R | L | n.d. |
| 32C9PMP2_B4 | P | D | F | E | L | G | S | V | R | P | R | Q | n.d. |
| 32C9PMP2_B7 | A | S | F | G | R | G | R | L | K | A | R | L | n.d. |
| 32C9PMP2_C10 | P | D | V | G | R | G | S | L | K | A | R | L | n.d. |
| 32C9PMP2_C9 | A | D | F | G | R | G | S | L | K | A | R | L | n.d. |
| 32C9PMP2_D5 | P | D | V | E | L | G | R | V | K | A | R | L | n.d. |
| 32C9PMP2_D8 | P | S | F | E | R | G | R | V | K | A | R | Q | n.d. |
| 32C9PMP2_D9 | P | S | F | G | R | G | S | V | R | P | R | L | n.d. |
| 32C9PMP2_E6 | P | S | F | E | R | G | R | V | K | A | R | L | n.d. |
| 32C9PMP1_A11 | P | S | V | E | R | W | S | V | K | A | R | L | n.d. |
| 32C9PMP1_A2 | P | D | V | E | R | W | S | V | K | A | R | L | n.d. |
| 32C9PMP1_A4 | P | D | F | E | R | W | S | L | R | P | R | Q | n.d. |
| 32C9PMP1_D7 | P | D | V | E | R | W | R | L | K | A | R | L | n.d. |
| 32C9PMP1_F9 | P | S | F | E | R | W | R | V | K | A | R | L | n.d. |
| 32C9PMP2_C12 | A | D | V | E | R | W | S | L | K | A | R | L | n.d. |
| 32C9PMP2_C4 | A | D | F | E | R | W | S | V | K | A | R | L | n.d. |
| 32C9PMP2_E7 | A | S | F | E | R | W | R | L | R | P | R | L | n.d. |
| 32C9PMP2_F2 | A | D | V | E | R | W | S | L | R | P | R | L | n.d. |
| 32C9PMP2_F5 | P | D | F | E | R | W | S | L | K | A | R | L | n.d. |

Numbering indicated at the top is according to Kabat.
Nanobody 32C9 wildtype is shown in bold.
"N.d" indicates that the off-rate was not determined Example 2: Affinity Maturation of Anti-Human IL6R Nanobody IL6R65 (Also Referred to as SEQ ID NO: 613 in WO2008020079A1)

Library Design

In order to improve the affinity of Nanobody IL6R65 (SEQ ID NO: 121) for its target human IL6R, libraries were made of IL6R65 variants containing one or more substitutions in the antigen binding CDR regions. Two different strategies were used for the diversification of the CDRs:

i. Substitution of each CDR residue by amino acids with similar side-chain chemistries according to the following scheme:

a. K↔R
b. A↔S↔T c. I↔L↔V
d. F↔Y
e. N↔D
f. Q↔E
g. G↔A
h. M↔L
i. H, C, W, P are kept constant ii. Substitution of each CDR residue by a panel of amino acids which naturally occur on the given position. Most frequently occurring amino acids on Nanobody positions 27-35 (CDR1) and 50-58 (CDR2) are listed in Table B-2 (numbering according to Kabat). Actual composition at each position may deviate due to the type of residues that can be encoded by a single degenerate codon. Number of different amino acids per position may be reduced to limit the total diversity of the library.

TABLE B-2

Most frequently occurring amino acids in CDR1 and CDR2 based on analysis of >350 unique Nanobodies. CDR2 sequences with and without an insertion at position 52a were analyzed separately:

| 27 | 28 | 29 | 30 | 31 | 32 | 33 | 34 | 35 |
|----|----|----|----|----|----|----|----|----|
| F  | A  | F  | D  | D  | D  | A  | I  | A  |
| G  | I  | G  | G  | I  | N  | G  | M  | G  |
| R  | S  | L  | S  | N  | Y  | T  |    | S  |
| S  | T  | S  | T  | S  |    | V  |    |    |
|    |    |    |    | T  |    |    |    |    |

| 50 | 51 | 52 | 52a | 53 | 54 | 55 | 56 | 57 | 58 |
|----|----|----|-----|----|----|----|----|----|----|
| A  | I  | N  | R   | D  | D  | D  | I  | T  | D  |
| C  |    | R  | S   | G  | G  | G  | N  |    | H  |
| G  |    | S  | T   | N  |    | S  | R  |    | N  |
| S  |    | T  | W   | S  |    |    | S  |    | S  |
| T  |    |    |     | T  |    |    | T  |    | Y  |

| 50 | 51 | 52 | 53 | 54 | 55 | 56 | 57 | 58 |
|----|----|----|----|----|----|----|----|----|
| A  | I  | N  | N  | D  | G  | G  | T  | D  |
| G  |    | S  | R  | G  |    | N  |    | N  |
| R  |    | T  | S  | R  |    | R  |    | T  |
| S  |    |    | T  | S  |    | S  |    | Y  |
| T  |    |    | Y  |    |    | T  |    |    |

CDR1 and CDR2 were mutagenized together using the 2 strategies described above whereas CDR3 was mutagenized separately using strategy 1 only resulting in a total of 3 libraries. An overview of the library compositions are shown in FIG. 4. The theoretical diversity for each of the libraries was approximately 1×10e6.

Library Construction

DNA fragments encoding the mutagenized CDR regions were generated by PCR overlap extension using degenerate oligos. After digestion with either XmaI/XbaI (libraries a and b) or BspeI/NotI (library c) (enzymes from New England Biolabs) the fragments were cloned into the corresponding restriction sites of tailored pAX50 phage display vectors. These vectors already contained a partial and frameshifted gene fragment of IL6R65 and were designed such that upon cloning the reading frame was restored and a full-length IL6R65 gene was generated. The actual size of all 3 libraries was around 1×10e8 (100× the theoretical diversity).

Selections

Phage libraries were panned for a maximum number of 3 rounds using decreasing concentrations of biotinylated IL6R (Peprotech) in solution (10 nM-1 pM). Complexes between phage and bio-IL6R were captured on magnetic streptavidin beads (Invitrogen) for 1 min and subsequently washed 5× with PBS-Tween. Bound phage were eluted by incubation for 30 min with 1 mg/ml trypsin at 37 C. Phage titers were determined by infection of E, coli TG1 cells (log-phase) (TG1 Electroporation-Competent Cells: cells from Stratagene, catalog number: 200123, 5×0.1-ml) with different dilutions of eluted phage. Selection conditions yielding phage titers higher than the control samples (without biotinylated IL6R) were selected for further analysis.

Analysis of Selection Outputs

Selection outputs were analyzed by picking individual colonies and growing them overnight in 1 ml 2×YT (Yeast Tryptone) medium+100 ug/ml Carbenicillin at 37 C. Nanobody containing periplasmic extracts were prepared, diluted 1/10 in PBS and subsequently tested for antigen binding in ELISA. Clones with the highest ELISA signals were sequenced and analyzed on Biacore. The top 50 clones in ELISA displayed off-rates between 1.4×10e-3 and 1.2×10e-4 s-1. The off-rate of the best clone from the CDR3 library was 7×10e-4 s-1. Nanobody sequences and off-rates are listed in Table B-3.

TABLE B-3

Amino acid sequences and off-rates of 50 Nanobodies displaying the highest ELISA signals. Top 50 clones of CDR3 library are also shown.

| Nanobody ID | protein sequence | SEQ ID NO: | off-rate (s-1) |
|---|---|---|---|
| ILR65 | EVQLVESGGGLVQPGGSLRLSCAASGSIFKVNAMGWYRQAPGKGRELVAGIISGGSTNYADSVKGRFTISRDNAKNTLYLQMNSLRPEDTAVYYCAFVTTNSDYDLGRDYWGQGTLVTVSS | 121 | |
| IL6R65PMP11E4 | EVQLVESGGGLVQPGGSLRLTCAASGTIFKVNVMAWYRQAPGKGRELVAAIITGGSTSYADSVKGRFTISRDNAKNTLYLQMNSLRPEDTAVYYCAFVTTNSDYDLGRDYWGQGTLVTVSS | 122 | 2.3E-04 |
| IL6R65PMP7F4 | EVQLVESGGGLVQPGGSLRLSCAASGTTFKVNVMAWYRQAPGKGRELVAGIINGGSTTYADSVKGRFTISRDNAKNTLYLQMNSLRPEDTAVYYCAFVTTNSDYDLGRDYWGQGTLVTVSS | 123 | 2.6E-04 |

TABLE B-3-continued

Amino acid sequences and off-rates of 50 Nanobodies displaying the highest ELISA signals. Top 50 clones of CDR3 library are also shown.

| Nanobody ID | protein sequence | SEQ ID NO: | off-rate (s-1) |
|---|---|---|---|
| IL6R65PMP 11D3 | EVQLVESGGGLVQPGGSLRLSCAASGSIFKLNVMAWYRQAPGKGRELVAGVITGGNTSYADSVKGRFTISRDNAKNTLYLQMNSLRPEDTAVYYCAFVTTNSDYDLGRDYWGQGTLVTVSS | 124 | 3.1E-04 |
| IL6R65PMP 11B4 | EVQLVESGGGLVQPGGSLRLSCAASGSIFKINVMAWYRQAPGKGRELVAAIINGGTTSYADSVKGRFTISRDNAKNTLYLQMNSLRPEDTAVYYCAFVTTNSDYDLGRDYWGQGTLVTVSS | 125 | 2.8E-04 |
| IL6R65PMP 11G7 | EVQLVESGGGLVQPGGSLRLSCAASGTIFKLNVMAWYRQAPGKGRELVAAIITGGTTTYADSVKGRFTISRDNAKNTLYLQMNSLRPEDTAVYYCAFVTTNSDYDLGRDYWGQGTLVTVSS | 126 | 3.6E-04 |
| IL6R65PMP 11F12 | EVQLVESGGGLVQPGGSLRLSCAASGTTFRVNVMAWYRQAPGKGRELVAAIISGGSTTYADSVKGRFTISRDNAKNTLYLQMNSLRPEDTAVYYCAFVTTNSDYDLGRDYWGQGTLVTVSS | 127 | 6.7E-04 |
| IL6R65PMP 11D12 | EVQLVESGGGLVQPGGSLRLSCAASGTIFKINIMAWYRQAPGKGRELVAAIINSGSTSYADSVKGRFTISRDNAKNTLYLQMNSLRPEDTAVYYCAFVTTNSDYDLGRDYWGQGTLVTVSS | 128 | 5.8E-04 |
| IL6R65PMP 13H4 | EVQLVESGGGLVQPGGSLRLSCAASGSAFKVNVMAWYRQAPGKGRELVAGVITDGSTNYADSVKGRFTISRDNAKNTLYLQMNSLRPEDTAVYYCAFVTTNSDYDLGRDYWGQGTLVTVSS | 129 | 5.2E-04 |
| IL6R65PMP 11G11 | EVQLVESGGGLVQPGGSLRLSCAASGTTFKINVMAWYRQAPGKGRELVAAIITSGTTSYADSVKGRFTISRDNAKNTLYLQMNSLRPEDTAVYYCAFVTTNSDYDLGRDYWGQGTLVTVSS | 130 | 5.0E-04 |
| IL6R65PMP 11E9 | EVQLVESGGGLVQPGGSLRLSCAASGTTFKINVMAWYRQAPGKGRELVAAIITGGTTTYADSVKGRFTISRDNAKNTLYLQMNSLRPEDTAVYYCAFVTTNSDYDLGRDYWGQGTLVTVSS | 131 | 3.5E-04 |
| IL6R65PMP 13F5 | EVQLVESGGGLVQPGGSLRLSCAASGTTFRINVMAWYRQAPGKGRELVAGIITNGSTSYADSVKGRFTISRDNAKNTLYLQMNSLRPEDTAVYYCAFVTTNSDYDLGRDYWGQGTLVTVSS | 132 | 3.7E-04 |
| IL6R65PMP 13D3 | EVQLVESGGGLVQPGGSLRLSCAANGTTFKVNVMAWYRQAPGKGRELVAGVITGGTTNYADSVKGRFTISRDNAKNTLYLQMNSLRPEDTAVYYCAFVTTNSDYDLGRDYWGQGTLVTVSS | 133 | 4.8E-04 |
| IL6R65PMP 11E2 | EVQLVESGGGLVQPGGSLRLSCAASGTTFKVNIMAWYRQAPGKGRELVAAIITGGSTSYADSVKGRFTISRDNAKNTLYLQMNSLRPEDTAVYYCAFVTTNSDYDLGRDYWGQGTLVTVSS | 134 | 6.8E-04 |
| IL6R65PMP 11H4 | EVQLVESGGGLVQPGGSLRLSCAASGSTFRLNVMAWYRQAPGKGRELVAAIITNGTTTYADSVKGRFTISRDNAKNTLYLQMNSLRPEDTAVYYCAFVTTNSDYDLGRDYWGQGTLVTVSS | 135 | 8.0E-04 |
| IL6R65PMP 11D6 | EVQLVESGGGLVQPGGSLRLSCAASGTTFKINVMAWYRQAPGKGRELVAAIISGGSTPYADSVKGRFTISRDNAKNTLYLQMNSLRPEDTAVYYCAFVTTNSDYDLGRDYWGQGTLVTVSS | 136 | 6.8E-04 |
| IL6R65PMP 13F3 | EVQLVESGGGLVQPGGSLRLSCAASGTTFKINVMAWYRQAPGKGRELVAAIITGGTTTYADSVKGRFTISRDNAKNTLYLQMNSLRPEDTAVYYCAFVTTNSDYDLGRDYWGQGTLVTVSS | 137 | 4.6E-04 |

TABLE B-3-continued

Amino acid sequences and off-rates of 50 Nanobodies displaying the highest ELISA signals. Top 50 clones of CDR3 library are also shown.

| Nanobody ID | protein sequence | SEQ ID NO: | off-rate (s-1) |
|---|---|---|---|
| IL6R65PMP 11H10 | EVQLVESGGGLVQPGGSLRLTCAASGTTFKVNVM AWYRQAPGKGRELVAAVINGGTTSYADSVKGRFT ISRDNAKNTLYLQMNSLRPEDTAVYYCAFVTTNS DYDLGRDYWGQGTLVTVSS | 138 | 4.3E-04 |
| IL6R65PMP 11F3 | EVQLVESGGGLVQPGGSLRLSCAASGTIFRINMA WYRQAPGKGRELVAAIISGGTTYADSVKGRFTIS RDNAKNTLYLQMNSLRPEDTAVYYCAFVTTNSDY DLGRDYWGQGTLVTVSS | 139 | 4.8E-04 |
| IL6R65PMP 11E11 | EVQLVESGGGLVQPGGSLRLSCAASGTTFKINVM AWYRQAPGKGRKLVAAIINNGNTTYADSVKGRFT ISRDNAKNTLYLQMNSLRPEDTAVYYCAFVTTNS DYDLGRDYWGQGTLVTVSS | 140 | 4.9E-04 |
| IL6R65PMP 13A11 | EVQLVESGGGLVQPGGSLRLSCAASGTVFKVNAM AWYRQAPGKGRELVAGVISAGSANYADSVKGRF TISRDNAKNTLYLQMNSLRPEDTAVYYCAFVTTN SDYDLGRDYWGQGTLVTVSS | 141 | 8.3E-04 |
| IL6R65PMP 12C7 | EVQLVESGGGLVQPGGSLRLSCAASGSVYRINAM GWYRQAPGKGRELVAGLISAGSTNYADSVKGRFT ISRDNAKNTLYLQMNSLRPEDTAVYYCAFVTTNS DYDLGRDYWGQGTLVTVSS | 142 | 9.1E-04 |
| IL6R65PMP 11E5 | EVQLVESGGGLVQPGGSLRLSCAASGSTFRINIMA WYRQAPGKGRELVAGVITSGNTTYADSVKGRFTI SRDNAKNTLYLQMNSLRPEDTAVYYCAFVTTNSD YDLGRDYWGQGTLVTVSS | 143 | 4.8E-04 |
| IL6R65PMP 11A12 | EVQLVESGGGLVQPGGSLRLSCAASGTIFRVNVM AWYRQAPGKGRELVAGIITNGSTSYADSVKGRFTI SRDNAKNTLYLQMNSLRPEDTAVYYCAFVTTNSD YDLGRDYWGQGTLVTVSS | 144 | 1.2E-04 |
| IL6R65PMP 11C7 | EVQLVESGGGLVQPGGSLRLSCAASGTIFKVNIMA WYRQAPGKGRELVAAIITSGTTTYADSVKGRFTIS RDNAKNTLYLQMNSLRPEDTAVYYCAFVTTNSDY DLGRDYWGQGTLVTVSS | 145 | 8.5E-04 |
| IL6R65PMP 11F1 | EVQLVESGGGLVQPGGTLRLSCAASGSTFKINVM AWYRQAPGKGRELVAGVITNGSTTYADSVKGRFT ISRDNAKNTLYLQMNSLRPEDTAVYYCAFVTTNS DYDLGRDYWGQGTLVTVSS | 146 | 3.7E-04 |
| IL6R65PMP 11F10 | EVQLVESGGGLVQPGGSLRLSCAASGTTFKLNIMA WYRQAPGKGRELVAAVINGGTTTYADSVKGRFTI SRDNAKNTLYLQMNSLRPEDTAVYYCAFVTTNSD YDLGRDYWGQGTLVTVSS | 147 | 1.3E-03 |
| IL6R65PMP 11C4 | EVQLVESGGGLVQPGGSLRLSCAASGTIFKINVMA WYRQAPGKGRELVAGIITNGSTTYADSVKGRFTIS RDNAKNTLYLQMNSLRPEDTAVYYCAFVTTNSDY DLGRDYWGQGTLVTVSS | 148 | 3.1E-04 |
| IL6R65PMP 7C4 | EVQLVESGGGLVQPGGSLRLSCAASGTTFRINVMA WYRQAPGKGRELVAGIITNGSTSYADSVKGRFTIS RDNAKNTLYLQMNSLRPEDTAVYYCAFVTTNSDY DLGRDYWGQGTLVTVSS | 149 | 4.3E-04 |
| IL6R65PMP 11G10 | EVQLVESGGGLVQPGGSLRLSCAASGSTFRINVMA WYRQAPGKGRELVAGIITNGTTTYADSVKGRFTIS RDNAKNTLYLQMNSLRPEDTAVYYCAFVTTNSDY DLGRDYWGQGTLVTVSS | 150 | 2.1E-04 |
| IL6R65PMP 11H2 | EVQLVESGGGLVQPGGSLRLSCAASGSIFKINVMA WYRQAPGKGRELVAAIINGGTTSYADSVKGRFTIS RDNAKNTLYLQMNSLRPEDTAVYYCAFVTTNSDY DLGRDYWGQGTLVTVSS | 151 | 3.0E-04 |

TABLE B-3-continued

Amino acid sequences and off-rates of 50 Nanobodies displaying the highest ELISA signals. Top 50 clones of CDR3 library are also shown.

| Nanobody ID | protein sequence | SEQ ID NO: | off-rate (s-1) |
|---|---|---|---|
| IL6R65PMP 7G8 | EVQLVESGGGLVQPGGSLRLSCAASGSTFRINVMAWYRQAPGKGRELVAGVINDGSTTYADSVKGRFTISRDNAKNTLYLQMNSLRPEDTAVYYCAFVTTNSDYDLGRDYWGQGTLVTVSS | 152 | 4.1E-04 |
| IL6R65PMP 11D4 | EVQLVESGGGLVQPGGSLRLSCAASGTTFKINIMAWYRQAPGKGRELVAGVINSGTTNYADSVKGRFTISRDNAKNTLYLQMNSLRPEDTAVYYCAFVTTNSDYDLGRDYWGQGTLVTVSS | 153 | 1.0E-03 |
| IL6R65PMP 11D11 | EVQLVESGGGLVQPGGSLRLSCAASGSTFKINIMAWYRQAPGKGRELVAGVITGGNTNYADSVKGRFTISRDNAKNTLYLQMNSLRPEDTAVYYCAFVTTNSDYDLGRDYWGQGTLVTVSS | 154 | 3.9E-04 |
| IL6R65PMP 13G5 | EVQLVESGGGLVQPGGSLRLSCAASGTIFKINIMAWYRQAPGKGRELVAAIINSGSTSYADSVKGRFTISRDNAKNTLYLQMNSLRPEDTAVYYCAFVTTNSDYDLGRDYWGQGTLVTVSS | 155 | 6.9E-04 |
| IL6R65PMP 7D6 | EVQLVESGGGLVQPGGSLRLSCAASGSIFRVNVMAWYRQAPGKGRELVAAVINGGTTYADSVKGRFTISRDNAKNTLYLQMNSLRPEDTAVYYCAFVTTNSDYDLGRDYWGQGTLVTVSS | 156 | 4.4E-04 |
| IL6R65PMP 13F10 | EVQLVESGGGLVQPGGSLRLSCAASGSVFKINAMGWYRQAPGKGRELVAGLISAGSTNYADSVKGRFTISRDNAKNTLYLQMNSLRPEDTAVYYCAFVTTNSDYDLGRDYWGQGTLVTVSS | 157 | 1.1E-03 |
| IL6R65PMP 18E11 | EVQLVESGGGLVQPGGSLRLSCAASGTTFRINVMAWYRQAPGKGRELVAGIITNGSTSYADSVKGRFTISRDNAKNTLYLQMNSLRPEDTAVYYCAFVTTNSDYDLGRDYWGQGTLVTVSS | 158 | 2.7E-04 |
| IL6R65PMP 13A4 | EVQLVESGGGLVQPGGSLRLSCAASGTTFRLNVMAWYRQAPGKGRELVAAIITSGTTYADSVKGRFTISRDNAKNTLYLQMNSLRPEDTAVYYCAFVTTNSDYDLGRDYWGQGTLVTVSS | 159 | 7.2E-04 |
| IL6R65PMP 18G11 | EVQLVESGGGLVQPGGSLRLSCAASGSIFKINVMAWYRQAPGKGRELVAAIINGGTTSYADSVKGRFTISRDNAKNTLYLQMNSLRPEDTAVYYCAFVTTNSDYDLGRDYWGQGTLVTVSS | 160 | 3.3E-04 |
| IL6R65PMP 13D2 | EVQLVESGGGLVQPGGSLRLSCAASGTTFKVNVMAWYRQAPGKGRELVAAIINDGSTTYADSVKGRFTISRDNAKNTLYLQMNSLRPEDTAVYYCAFVTTNSDYDLGRDYWGQGTLVTVSS | 161 | 1.1E-03 |
| IL6R65PMP 13A2 | EVQLVESGGGLVQPGGSLRLSCAASGTIFRVNVMAWYRQAPGKGRELVAAIITDGTTTYADSVKGRFTISRDNAKNTLYLQMNSLRPEDTAVYYCAFVTTNSDYDLGRDYWGQGTLVTVSS | 162 | 6.1E-04 |
| IL6R65PMP 13B3 | EVQLVESGGGLVQPGGSLHLSCAASGTIFKINVMAWYRQAPGKGRELVAAIITDGSTTYADSVKGRFTISRDNAKNTLYLQMNSLRPEDTAVYYCAFVTTNSDYDLGRDYWGQGTLVTVSS | 163 | 7.6E-04 |
| IL6R65PMP 13B2 | EVQLVESGGGLVQPGGSLRLSCAASGTTFKVNIMAWYRQAPGKGRELVAAIITNGSTTYADSVKGRFTISRDNAKNTLYLQMNSLRPEDTAVYYCAFVTTNSDYDLGRDYWGQGTLVTVSS | 164 | 1.4E-03 |
| IL6R65PMP 12E1 | EVQLVESGGGLVQPGGSLRLSCAANGSVYKVNAMAWYRQAPGKGRELVAGIVTGGTSNYADSVKGRFTISRDNAKNTLYLQMNSLRPEDTAVYYCAFVTTNSDYDLGRDYWGQGTLVTVSS | 165 | 2.6E-04 |

TABLE B-3-continued

Amino acid sequences and off-rates of 50 Nanobodies displaying the highest ELISA signals. Top 50 clones of CDR3 library are also shown.

| Nanobody ID | protein sequence | SEQ ID NO: | off-rate (s-1) |
|---|---|---|---|
| IL6R65PMP 18G8 | EVQLVESGGGLVQPGGSLRLSCAASGTTFKINVM AWYRQAPGKGRELVAGIITGGTTTYADSVKGRFTI SRDNAKNTLYLQMNSLRPEDTAVYYCAFVTTNSD YDLGRDYWGQGTLVTVSS | 166 | 2.3E-04 |
| IL6R65PMP 16H6 | EVQLVESGGGLVQPGGSLRLSCAASGSVFRINAM AWYRQAPGKGRELVAGFVTGGSSNYADSVKGRF TISRDNAKNTLYLQMNSLRPEDTAVYYCAFVTTN SDYDLGRDYWGQGTLVTVSS | 167 | 3.2E-04 |
| IL6R65PMP 18G12 | EVQLVESGGGLVQPGGSLRLSCAASGSIFKINVMA WYRQAPGKGRELVAAIINSGTTSYADSVKGRFTIS RDNAKNTLYLQMNSLRPEDTAVYYCAFVTTNSDY DLGRDYWGQGTLVTVSS | 168 | 3.4E-04 |
| IL6R65PMP 7G7 | EVQLVESGGGLVQPGGSLRLSCAASGTTFKINIMA WYRQAPGKGRELVAGVITGGNTTYADSVKGRFTI SRDNAKNTLYLQMNSLRPEDTAVYYCAFVTTNSD YDLGRDYWGQGTLVTVSS | 169 | 3.7E-04 |
| IL6R65PMP 18G7 | EVQLVESGGGLVQPGGSLRLSCAASGTTFKVNVM AWYRQAPGKGRELVAGIITGGSTTYADSVKGRFTI SRDNAKNTLYLQMNSLRPEDTAVYYCAFVTTNSD YDLGRDYWGQGTLVTVSS | 170 | 3.0E-04 |
| IL6R65PMP 12C8 | EVQLVESGGGLVQPGGSLRLSCAASGTVFKINAM AWYRQAPGKGRELVAGLVSAGTANYADSVKGRF TISRDNAKNTLYLQMNSLRPEDTAVYYCAFVTTN SDYDLGRDYWGQGTLVTVSS | 171 | 6.6E-04 |
| IL6R65PMP 18B1 | EVQLVESGGGLVQPGGSLRLSCAASGSIFKVNAM GWYRQAPGKGRELVAGIISGGSTNYADSVKGRFTI SRDNAKNTLYLQMNSLRPEDTAVYYCAFITADTD YDLGKRYWGQGTLVTVSS | 172 | 7.2E-04 |
| IL6R65PMP 19H2 | EVQLVESGGGLVQPGGSLRLSCAASGSIFKVNAM GWYRQAPGKGRELVAGIISGGSTNYADSVKGRFTI SRDNAKNTLYLQMNSLRPEDTAVYYCAFITADTD YDLGKRYWGQGTLVTVSS | 173 | 7.4E-04 |
| IL6R65PMP 19A4 | EVQLVESGGGLVQPGGSLRLSCAASGSIFKVNAM GWYRQAPGKGRELVAGIISGGSTNYADSVKGRFTI SRDNAKNTLYLQMNSLRPEDTAVYYCAFITTDTN YDLGKRSWGQGTLVTVSS | 174 | 8.9E-04 |
| IL6R65PMP 10A11 | EVQLVESGGGLVQPGGSLRLSCAASGSIFKVNAM GWYRQAPGKGRELVAGIISGGSTNYADSVKGRFTI SRDNAKNTLYLQMNSLRPEDTAVYYCAFIASNSE YDLGRRFWGQGTLVTVSS | 175 | 1.0E-03 |
| IL6R65PMP 19H7 | EVQLVESGGGLVQPGGSLRLSCAASGSIFKVNAM GWYRQAPGKGRELVAGIISGGSTNYADSVKGRFTI SRDNAKNTLYLQMNSLRPEDTAVYYCAFITADTE YDLGKRFWGQGTLVTVSS | 176 | 1.1E-03 |

Characterization of Selected IL6R65 Variants

Five Nanobodies from library b with improved off-rates ranging from 2.6×10e−4 to 4.4×10e−4 s−1 were expressed in E. coli and purified via IMAC chromatography. Binding curves at different concentrations of purified Nanobody were recorded on Biacore and used to calculate values for ka, kd and Kd (Table B-4). Kd-values for these 5 clones were between 0.34 and 0.95 nM which corresponds to a 13-fold improvement relative to the parent molecule for the best variant.

TABLE B-4

Comparison of kinetic parameters of IL6R65 and 5 affinity matured variants

| | ka (1/Ms) | kd (1/s) | Kd (nM) |
|---|---|---|---|
| IL6R65 | 5.39E+05 | 2.34E-03 | 4.30 |
| IL6R65PMP7G8 | 3.52E+05 | 3.33E-04 | 0.95 |
| IL6R65PMP7F4 | 6.09E+05 | 2.92E-04 | 0.48 |
| IL6R65PMP7D6 | 6.72E+05 | 2.79E-04 | 0.42 |
| IL6R65PMP7G7 | 5.50E+05 | 3.10E-04 | 0.56 |
| IL6R65PMP7C4 | 5.27E+05 | 1.77E-04 | 0.34 |

All 5 Nanobodies and the parent Nanobody were also tested in a plasma potency assay. In this assay different concentrations of Nanobody are mixed with soluble IL6R containing plasma from either human or cynomolgus monkey and a fixed concentration of human IL6. After 1 hour of incubation the mixture is transferred to a Maxisorp plate coated with the anti-IL6R MAb BN-12 (Diaclone). The amount of IL6 bound was determined by subsequent addition of biotinylated anti-IL6 polyclonal antibody (R&D Systems) and streptavidin-HRP. TMB was used as substrate. Substrate conversion was measured at 450 nm.

TABLE B-5

Evaluation of IL6R65 and 5 affinity matured variants in a cyno plasma potency assay (see also FIG. 5).

| Nanobody | IC50 (nM) |
| --- | --- |
| IL6R65 | 2.99 |
| PMP7G8 | 0.14 |
| PMP7G7 | 0.11 |
| PMP7D6 | 0.09 |
| PMP7F4 | 0.09 |
| PMP7C4 | 0.08 |

TABLE B-6

Evaluation of IL6R65 and 5 affinity matured variants in a human plasma potency assay (see also FIG. 6).

| Nanobody | IC50 (nM) |
| --- | --- |
| IL6R65 | 4.93 |
| PMP7G8 | 0.34 |
| PMP7F4 | 0.24 |
| PMP7G7 | 0.22 |
| PMP7C4 | 0.21 |
| PMP7D6 | 0.19 |

The affinity matured Nanobodies were also tested for their ability to inhibit IL6-dependent proliferation of TF-1 cells (ECACC no. 93022307; J Cell Physiol 1989; 140:323; Exp Cell Res 1993:208:35) due to blocking of IL6 binding to IL6R on the cell-surface. To this end, serial dilutions of Nanobody were pre-incubated with a fixed amount of TF-1 cells for 2 hours at 37 C. Subsequently IL6 was added to a final concentration of 2 ng/ml. IL6-dependent cell proliferation was allowed to continue for 72 hours and was measured by the incorporation of tritium labeled thymidine.

TABLE B-7

Inhibition of IL6-dependent proliferation of TF-1 cells.

| Nanobody | IC50 (nM) |
| --- | --- |
| IL6R65 | 55.0 |
| PMP7C4 | 2.5 |
| PMP7D6 | 3.7 |
| PMP7F4 | 5.2 |
| PMP7G7 | 3.5 |
| PMP7G8 | 6.2 |

Cells were grown in the presence of 2 ng/ml human IL6 and various concentrations of Nanobody. Proliferation was measured by 3H-thymidine incorporation (see also FIG. 7).

The invention claimed is:

1. Method for providing a library of nucleotide sequences that encode amino acid sequences that comprise or essentially consist of an immunoglobulin single variable domain that is a heavy chain variable domain and that forms a single functional antigen-binding unit, which method at least comprises the steps of:
   a) providing a pool of oligonucleotides that consists of (i) a series of at least two oligonucleotides that can be assembled, by means of PCR assembly, into a nucleotide sequence that encodes an amino acid sequence that comprises or essentially consists of an immunoglobulin single variable domain that is a heavy chain variable domain and that forms a single functional antigen-binding unit, and in addition (ii) at least one variant of at least one oligonucleotide of the at least two oligonucleotides that form part of the series, in which said at least one variant differs from said at least one oligonucleotide (and also from the other variants of said at least one oligonucleotide present in the pool, if any) in that it encodes an amino acid sequence that differs from the amino acid sequence encoded by said at least one oligonucleotide in the presence of one or more specific mutations;
   b) subjecting the pool of oligonucleotides to PCR assembly; and
   c) screening the library of nucleotide sequences obtained through steps a) and b) for nucleotide sequences that encode amino acid sequences that have one or more specific mutations,
      or
      testing one or more nucleotide sequences from the library of nucleotide sequences obtained through steps a) and b) as to whether they encode an amino acid sequence that has one or more specific mutations;
wherein the oligonucleotides and the variants of said oligonucleotides used in step a) are such that each of the nucleotide sequences obtained as a result of the PCR assembly with a variant oligonucleotide in step b) encode an amino acid sequence that only contains one or more specific mutations in the amino acid residues at positions 27 to 35, 50 to 65 or 95 to 102 according to Kabat numbering that are generated following the rules described in i) or ii), wherein for
   i) the one or more specific mutations in the amino acid residues at positions 27 to 35, 50 to 65 or 95 to 102 according to Kabat numbering are generated by substituting the nucleotide sequences such that amino acid sequences with the following predetermined amino acid residue(s) are generated:

if the nucleotide sequence encodes K, substitute the nucleotide sequence such that an amino acid sequence with R is generated;
if the nucleotide sequence encodes R, substitute the nucleotide sequence such that an amino acid sequence with K is generated;
if the nucleotide sequence encodes A, substitute the nucleotide sequence such that an amino acid sequence with S or T or both is generated,
if the nucleotide sequence encodes S, substitute the nucleotide sequence such that an amino acid sequence with A or T or both is generated,
if the nucleotide sequence encodes T, substitute the nucleotide sequence such that an amino acid sequence with A or S or both is generated,
if the nucleotide sequence encodes I, substitute the nucleotide sequence such that an amino acid sequence with L or V or both is generated;
if the nucleotide sequence encodes L, substitute the nucleotide sequence such that an amino acid sequence with I or V or both is generated;
if the nucleotide sequence encodes V, substitute the nucleotide sequence such that an amino acid sequence with I or L or both is generated;
if the nucleotide sequence encodes F, substitute the nucleotide sequence such that an amino acid sequence with Y is generated;
if the nucleotide sequence encodes Y, substitute the nucleotide sequence such that an amino acid sequence with F is generated;
if the nucleotide sequence encodes N, substitute the nucleotide sequence such that an amino acid sequence with D is generated;
if the nucleotide sequence encodes D, substitute the nucleotide sequence such that an amino acid sequence with N is generated;
if the nucleotide sequence encodes Q, substitute the nucleotide sequence such that an amino acid sequence with E is generated;
if the nucleotide sequence encodes E, substitute the nucleotide sequence such that an amino acid sequence with Q is generated;
if the nucleotide sequence encodes G, substitute the nucleotide sequence such that an amino acid sequence with A is generated; or
if the nucleotide sequence encodes M, substitute the nucleotide sequence such that an amino acid sequence with L is generated; and wherein for
ii) the one or more specific mutations at positions 95 to 102 according to Kabat numbering are generated using the rules as above in i) and the one or more specific mutations at positions 27 to 35 or 50 to 65 according to Kabat numbering are generated by substituting the nucleotide sequences such that amino acid sequences with the following predetermined amino acid residue are generated:

any of F, G, R, and S in position 27;
any of A, I, S, and T in position 28;
any of F, G, L, and S in position 29;
any of D, G, S, and T in position 30;
any of D, I, N, S, and T in position 31;
any of D, N, and Y in position 32;
any of A, G, T, and V in position 33;
any of I, and M in position 34;
any of A, G, and S in position 35;
if amino acid sequence has an amino acid residue in position 52a in CDR2,
any of A, C, G, S, and T in position 50;
I in position 51;
any of N, R, S, and T in position 52;
any of R, S, T, and W in position 52a;
any of D, G, N, S, and T in position 53;
any of D, and G in position 54;
any of D, G, and S in position 55;
any of I, N, R, S, and T in position 56;
T in position 57;
any of D, H, N, S, and Y in position 58; or
if amino acid sequence has no amino acid residue in position 52a in CDR2,
any of A, G, R, S, and T in position 50;
I in position 51;
any of N, S, and T in position 52;
any of N, R, S, T, and Y in position 53;
any of D, G, R, and S in position 54;
any of G in position 55;
any of G, N, R, S, and T in position 56;
T in position 57;
any position of D, N, T, and Y in position 58.

2. Method according to claim 1, in which the oligonucleotides and variants thereof used in step a) are such that the nucleotide sequences obtained as a result of the PCR assembly in step b) encode amino acid sequences that comprise or essentially consist of 4 framework regions and 3 complementarity determining regions that differ from each other in the presence of one or more specific mutations in the framework regions.

3. Method according to claim 1, in which said pool of oligonucleotides used in step a) are such that the nucleotide sequences obtained as a result of the PCR assembly in step b) encode amino acid sequences that comprise or essentially consist of 4 framework regions and 3 complementarity determining regions that differ from each other in the presence of one or more specific mutations in the complementarity determining regions.

4. Method according to claim 1, in which the oligonucleotides and variants thereof used in step a) are such that the nucleotide sequences obtained as a result of the PCR assembly in step b) encode amino acid sequences that comprise or essentially consist of 4 framework regions and 3 complementarity determining regions that differ from each other in the presence of one or more specific mutations in the amino acid residues at positions 27 to 35, 50 to 65 or 95 to 102 according to Kabat numbering.

5. Method according to claim 1, in which the oligonucleotides and variants thereof used in step a) are such that the nucleotide sequences obtained as a result of the PCR assembly in step b) encode amino acid sequences that comprise or essentially consist of a Nanobody.

* * * * *